US012577302B2

(12) United States Patent (10) Patent No.: US 12,577,302 B2
Lindsted et al. (45) Date of Patent: Mar. 17, 2026

(54) ANTI-TIM-3 ANTIBODIES AND COMPOSITIONS

(71) Applicant: LES LABORATOIRES SERVIER, Suresnes Cedex (FR)

(72) Inventors: Trine Lindsted, Farum (DK); Torben Gjetting, Jyllinge (DK); Gunther Roland Galler, Jyllinge (DK); Monika Gad, Alleroed (DK); Michael Monrad Grandal, Ballerup (DK); Klaus Koefoed, Copenhagen V (DK); Michael Kragh, Copenhagen N (DK); Ivan David Horak, West Orange, NJ (US); Thomas Bouquin, Alleroed (DK); Mikkel Wandahl Pedersen, Alleroed (DK)

(73) Assignee: LES LABORATOIRES SERVIER, Suresnes Cedex (FR)

( * ) Notice: Subject to any disclaimer, the term of this patent is extended or adjusted under 35 U.S.C. 154(b) by 126 days.

(21) Appl. No.: 17/741,967

(22) Filed: May 11, 2022

(65) Prior Publication Data

US 2023/0105714 A1 Apr. 6, 2023

Related U.S. Application Data

(62) Division of application No. 16/093,024, filed as application No. PCT/EP2017/058696 on Apr. 11, 2017, now Pat. No. 11,390,674.

(60) Provisional application No. 62/321,476, filed on Apr. 12, 2016.

(51) Int. Cl.
| | |
|---|---|
| *C07K 16/00* | (2006.01) |
| *A61K 39/395* | (2006.01) |
| *A61K 45/06* | (2006.01) |
| *C07K 16/28* | (2006.01) |
| *C07K 16/46* | (2006.01) |
| *A61K 39/00* | (2006.01) |

(52) U.S. Cl.
CPC .... *C07K 16/2803* (2013.01); *A61K 39/39566* (2013.01); *A61K 45/06* (2013.01); *C07K 16/468* (2013.01); *A61K 2039/505* (2013.01); *C07K 2317/21* (2013.01); *C07K 2317/31* (2013.01); *C07K 2317/33* (2013.01); *C07K 2317/34* (2013.01); *C07K 2317/51* (2013.01); *C07K 2317/52* (2013.01); *C07K 2317/75* (2013.01); *C07K 2317/76* (2013.01); *C07K 2317/92* (2013.01)

(58) Field of Classification Search
CPC ................................................. C07K 16/2803
See application file for complete search history.

(56) References Cited

U.S. PATENT DOCUMENTS

| | | | |
|---|---|---|---|
| 10,550,181 | B2 | 2/2020 | Takayanagi et al. |
| 11,939,380 | B2 | 3/2024 | Lindsted et al. |
| 2011/0059106 | A1 | 3/2011 | Kuchroo et al. |
| 2012/0100131 | A1 | 4/2012 | Takayanagi et al. |
| 2013/0022623 | A1 | 1/2013 | Karsunky et al. |
| 2015/0218274 | A1 | 8/2015 | Sabatos-Peyton et al. |
| 2022/0380470 | A1 | 12/2022 | Lindsted et al. |

FOREIGN PATENT DOCUMENTS

| | | |
|---|---|---|
| CN | 103936853 | 5/2013 |
| EP | 2581113 A1 | 4/2013 |
| WO | WO 2010/084999 | 7/2010 |
| WO | WO 2011/159877 A2 | 12/2011 |
| WO | WO 2013/006490 A2 | 1/2013 |
| WO | WO 2014/121221 | 8/2014 |
| WO | WO 2015/048312 | 4/2015 |
| WO | WO 2015/117002 A1 | 8/2015 |
| WO | WO 2015/136541 | 9/2015 |
| WO | WO 2015/175340 A1 | 11/2015 |
| WO | WO 2016/111947 A2 | 7/2016 |
| WO | WO 2016/144803 A2 | 9/2016 |
| WO | WO 2017/019897 A1 | 2/2017 |
| WO | WO 2017/031242 A1 | 2/2017 |
| WO | WO 2017/055404 | 4/2017 |
| WO | WO2018/013818 | 1/2018 |
| WO | WO2018/039020 | 3/2018 |
| WO | WO2018/106588 A2 | 6/2018 |
| WO | WO 2018/185232 | 10/2018 |
| WO | WO2018/191074 | 10/2018 |

OTHER PUBLICATIONS

MacCallum et al, J. Mol. Biol., 262, 732-745, 1996.*
Pascalis et al, Journal of Immunology, 2002, vol. 169, pp. 3076-3084.*
Casset et al, Biochemical and Biophysical Research Communications, 2003, vol. 307, pp. 198-205.*
Holm et al, Molecular Immunology, 2007, vol. 44, pp. 1075-1084.*
Du et al., "TIM-3 as a Target for Cancer Immunotherapy and Mechanisms of Action," Int J Mol Sci. 18(3):645 (2017).
Friedlaender et al., "New emerging targets in cancer immunotherapy: the role of TIM3," ESMO Open.4(Suppl 3): e000497 (2019).
Guo et al., "Combined TIM-3 blockade and CD137 activation affords the long-term protection in a murine model of ovarian cancer," J Transl Med. 11:215 (2013).
Jin et al., "Cooperation of TIM-3 and PD-1 in CD8 T-cell exhaustion during chronic viral infection," Proc Natl Acad Sci U S A. 107(33):14733-8 (2010).
Jun et al., "Generation of antagonistic anti-TIM-3 and anti-LAG-3 monoclonal antibodies for potential novel immunotherapy combinations," Cancer Res 74 (19 Supplement): LB-266 (2014).
Kuchroo et al., "New roles for TIM family members in immune regulation," Nat Rev Immunol 8:577-80 (2008).

(Continued)

*Primary Examiner* — Mark Halvorson

(74) *Attorney, Agent, or Firm* — Steptoe LLP; Z. Ying Li; Carolyn A. Breckel

(57) ABSTRACT

This invention relates to anti-TIM-3 antibodies and antibody compositions and their use in enhancing immunity in a patient, e.g., to treat cancer.

19 Claims, 13 Drawing Sheets

Specification includes a Sequence Listing.

(56) References Cited

OTHER PUBLICATIONS

Pascalis et al., "Grafting of 'abbreviated' complementarity-determining regions containing specificity-determining residues essential for ligand contact to engineer a less immunogenic humanized monoclonal antibody," J Immunol. 169(6):3076-84 (2002).

Sakuishi et al., "Targeting Tim-3 and PD-1 pathways to reverse T cell exhaustion and restore anti-tumor immunity," J Exp Med. 207(10):2187-94 (2010).

U.S. Appl. No. 18/444,187, filed Feb. 16, 2024.

U.S. Pat. No. 11,939,380, Oct. 4, 2019/Mar. 26, 2024, Lindsted et al.

U.S. Appl. No. 18/444,187, filed Feb. 16, 2024, Lindsted et al.

U.S. Appl. No. 17/834,554, filed Jun. 7, 2022, Lindsted et al.

Anonymous, "NCT02608268: Phase I-Ib/II Open-label Multi-center Study of the Safety and Efficacy of MBG453 [TIM-3] as Single Agent and in Combination with PDR001 [PD-1]in Adult Patients with Advanced Malignancies," ClinicalTrials.gov (2017).

Anonymous, "NCT02817633: A Phase 1 Dose Escalation and Cohort Expansion Study of TSR-022, an Anti-TIM-3 Monoclonal Antibody, in Patients with Advanced Solid Tumors," ClinicalTrials. gov (2017).

Anderson et al., "Promotion of tissue inflammation by the immune receptor Tim-3 expressed on innate immune cells," Science 318:1141-1143 (2007).

Casset et al., "A peptide mimetic of an anti-CD4 monoclonal antibody by rational design," Biochem Biophys Res Commun. 307(1):198-205 (2003).

Chiba et al., "Tumor-infiltrating DCs suppress nucleic acid-mediated innate immune responses through interactions between the receptor TIM-3 and the alarmin HMGB1," Nat. Immunology 13(9):832-42 (2012).

Colman, "Effects of amino acid sequence changes on antibody-antigen interactions," Res Immunol 145:33-36 (1994).

Das et al., "Tim-3 and its role in regulating anti-tumor immunity," Immunol Rev. 276(1):97-111 (2017).

Da Silva et al., "Reversal of NK-cell exhaustion in advanced melanoma by Tim-3 blockade," Cancer Immunol Res 2:410-422 (2014).

DeKruyff et al., "T cell/transmembrane, Ig, and mucin-3 allelic variants differentially recognize phosphatidylserine and mediate phagocytosis of apoptotic cells," J Immunology 184(4):1918-30 (2010).

Freeman et al., "TIM genes: a family of cell surface phosphatidylserine receptors that regulate innate and adaptive immunity," Immunol Rev 235:172-89 (2010).

Jing et al., "Combined immune checkpoint protein blockade and low dose whole body irradiation as immunotherapy for myeloma," J Immunother Cancer 3(1):2 (2015).

Kehry, "Targeting PD-1, TIM-3 and LAG-3 in combination for improved Immunotherapy Combinations," Journal for immunotherapy of cancer, 1 page (2015).

Kikushige et al., "TIM-3 as a novel therapeutic target for eradicating acute myelogenous leukemia stem cells," Int J Hematol 98(6):627-33 (2013).

Li et al., "Tim-3/galectin-9 signaling pathway mediates T-cell dysfunction and predicts poor prognosis in patients with hepatitis B virus-associated hepatocellular carcinoma," Hepatology 56(4):1342-51 (2012).

Liu et al., "Targeting PD-1 and Tim-3 pathways to reverse CD8 T-Cell exhaustion and enhance Ex Vivo T-Cell responses to autologous dendritic/tumor vaccines," J Immunother 39(4):171-80 (2016).

MacCallum et al., "Antibody-antigen interactions: contact analysis and binding site topography," J Mol Biol. 262(5):732-45 (1996).

Moon, "Abstract 1641: Dual antibody blockade of TIM3 and PD1 on NYES01 redirected human T cells leads to augmented control of lung cancer tumors," Cancer Research 77: 1641(2017).

Paul, "Fundamental Immunology," 3rd Edition pp. 292-295 (1993).

Rudikoff et al., "Single amino acid substitution altering antigen-binding specificity," Proc Natl Acad Sci USA 79(6):1979-1983 (1982).

U.S. Appl. No. 18/444,187, filed Feb. 16, 2024, titled "Combination Therapies Targeting PD-1, TIM-3, and LAG-3," 178 pages.

* cited by examiner

A

| | ,003 | ,012 | ,049 | ,195 | ,781 | 3,125 | 12,500 | 50,000 |
|---|---|---|---|---|---|---|---|---|
| mAb-5429 | 7157,3 | 7595,1 | 6892,6 | 6074,7 | 3238,1 | 114,6 | 35,4 | 37,4 |

B

| | ,003 | ,012 | ,049 | ,195 | ,781 | 3,125 | 12,500 | 50,000 |
|---|---|---|---|---|---|---|---|---|
| mAb-6240 | 5956,2 | 4602,0 | 4511,3 | 5212,4 | 5329,8 | 5718,6 | 5553,2 | 6086,7 |

C

| | .003 | .012 | .049 | .195 | .781 | 3.125 | 12.500 | 50.000 |
|---|---|---|---|---|---|---|---|---|
| mAb-5686 | 8704.6 | 8734.8 | 8888.6 | 8797.1 | 4483.3 | 183.6 | 159.6 | 156.9 |

D

| | .003 | .012 | .049 | .195 | .781 | 3.125 | 12.500 | 50.000 |
|---|---|---|---|---|---|---|---|---|
| Keytruda | 5820.2 | 5200.0 | 4392.5 | 5203.8 | 4786.8 | 4253.3 | 3813.5 | 4968.6 |

Bin 1: mAb15
Bin 2: 15105, 15107
Bin 3: AbTIM3, 15260
Bin 4: 20621, 20293, 19568, 20362, 15086, 19416
Bin 5: 20131, 20185
Bin 6: 19324, 20300
Bin 7: 17244
Bin 8: 15174, 15175
Functional mAbs

SEQUENCE LISTING

```
<160> NUMBER OF SEQ ID NOS: 240

<210> SEQ ID NO 1
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
caggtgcagc tacagcagtc gggcccagga ctggtgaagc cttcacagac cctgtccctc      60
acctgcactg tctctggtgg ctccatcagc agtggtggtt actactggag ttggacccgt     120
cagcacccag ggatgggcct ggagtggatt ggatacatct cttacagtgg gagtatctat     180
tacactccgt ccctcaagag tcgacttacc atatcagtgg acacgtctaa gaaccagttc     240
tccctgaagc tgagctctgt gactgccgcg gacacggccg tatattactg tgcgagtttg     300
gattcctggg gatctaaccg tgactactgg ggccagggaa ccctggtcac cgtctcgagt     360

<210> SEQ ID NO 2
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
gaaattgtgt tgacgcagtc tccagccacc ctgtctttgt ctccagggga aagagccacc      60
```

-continued

```
ctctcctgca gggccagtca gagtgttagc agctacttag cctggtacca acagaaacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagcaact ggccgctcac tttcggcgga      300
gggaccaagg tggagattaa g                                                321
```

```
<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Thr Arg Gln His Pro Gly Met Gly Leu Glu
        35                  40                  45

Trp Ile Gly Tyr Ile Ser Tyr Ser Gly Ser Ile Tyr Tyr Thr Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Leu Asp Ser Trp Gly Ser Asn Arg Asp Tyr Trp Gly Gln
            100                 105                 110

Gly Thr Leu Val Thr Val Ser Ser
        115                 120
```

```
<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

```
<210> SEQ ID NO 5
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 107
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Gly Ser Ile Ser Ser Gly Gly Tyr Tyr
1               5                   10

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Ser Tyr Ser Gly Ser Ile
1               5

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Cys Ala Ser Leu Asp Ser Trp Gly Ser Asn Arg Asp Tyr Trp
1               5                   10

<210> SEQ ID NO 10
<211> LENGTH: 6
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 10

Gln Ser Val Ser Ser Tyr
1               5

<210> SEQ ID NO 11
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Asp Ala Ser
1

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Cys Gln Gln Arg Ser Asn Trp Pro Leu Thr Phe
1               5                   10

<210> SEQ ID NO 13
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
caggtgcagc tgcaggagag tggcccccgga ctggtcaagc cttcacagac tctgagcctg      60
acctgcacag tgtctggcgg aagtatcagc tccgggggtt actattggag ctggacccga     120
cagcacccag gaatgggtct ggaatggatc gggtacattt catatagcgg ctccatctac     180
tatacaccct cactgaaaag caggctgacc atttccgtgg acacatctaa gaaccagttc     240
agcctgaaac tgtctagtgt gacagccgct gatactgcag tctactattg tgcctccctg     300
gactcttggg gcagtaatag agattactgg ggccagggaa ctctggtcac cgtctcgagt     360

<210> SEQ ID NO 14
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
gagatcgtgc tgactcagtc cccagccacc ctgtcactga gcccaggaga acgagcaacc      60
ctgtcttgca gggcctccca gtctgtcagc tcctacctgg cttggtatca gcagaagccc     120

```
gggcaggcac ctcgactgct gatctacgac gccagtaaca gagctaccgg tattcccgcc      180
cgcttcagtg gttcaggcag cggaacagac tttaccctga caatctctag tctggagcct      240
gaagatttcg ccgtgtacta ttgtcagcag aggtctaatt ggccactgac atttggcgga      300
gggactaagg tcgagatcaa g                                               321
```

```
<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Thr Arg Gln His Pro Gly Met Gly Leu Glu
        35                  40                  45

Trp Ile Gly Tyr Ile Ser Tyr Ser Gly Ser Ile Tyr Tyr Thr Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Leu Asp Ser Trp Gly Ser Asn Arg Asp Tyr Trp Gly Gln
            100                 105                 110

Gly Thr Leu Val Thr Val Ser Ser
        115                 120
```

```
<210> SEQ ID NO 16
<211> LENGTH: 990
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
gcctccacca agggcccatc ggtcttcccc ctggcaccct cctccaagag cacctctggg       60
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagag agttgagccc      300
aaatcttgtg acaaaactca cacatgccca ccgtgcccag cacctgaagc cgcggggga      360 ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
```

-continued

```
aaagccaaag ggcagccccg agaaccacag gtgtacaccc tgcccccatc ccgggaggag        720
atgaccaaga accaggtcag cctgacctgc ctggtcaaag gcttctatcc cagcgacatc        780
gccgtggagt gggagagcaa tgggcagccg gagaacaact acaagaccac gcctcccgtg        840
ctggactccg acggctcctt cttcctctat agcaagctca ccgtggacaa gagcaggtgg        900
cagcagggga acgtcttctc atgctccgtg atgcatgagg ctctgcacaa ccactacacg        960
cagaagagcc tctccctgtc cccgggtaaa                                         990
```

```
<210> SEQ ID NO 17
<211> LENGTH: 1596
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
```

```
gcctccacca agggcccatc ggtcttcccc ctggcaccct cctccaagag cacctctggg         60
ggcacagcgg ccctgggctg cctggtcaag gactacttcc ccgaaccggt gacggtgtcg        120
tggaactcag gcgccctgac cagcggcgtg cacaccttcc cggctgtcct acagtcctca        180
ggactctact ccctcagcag cgtggtgacc gtgccctcca gcagcttggg cacccagacc        240
tacatctgca acgtgaatca caagcccagc aacaccaagg tggacaagag agttggtgag        300
aggccagcac agggagggag ggtgtctgct ggaagccagg ctcagcgctc ctgcctggac        360
gcatcccggc tatgcagtcc cagtccaggc agcaaggca ggccccgtct gcctcttcac         420
ccggaggcct ctgcccgccc cactcatgct cagggagagg gtcttctggc tttttcccca        480
ggctctgggc aggcacaggc taggtgcccc taacccaggc cctgcacaca aaggggcagg        540
tgctgggctc agacctgcca agagccatat ccgggaggac cctgcccctg acctaagccc        600
accccaaagg ccaaactctc cactccctca gctcggacac cttctctcct cccagattcc        660
agtaactccc aatcttctct ctgcagagcc caaatcttgt gacaaaactc acacatgccc        720
accgtgccca ggtaagccag cccaggcctc gccctccagc tcaaggcggg acaggtgccc        780
tagagtagcc tgcatccagg acaggcccc agccgggtgc tgacacgtcc acctccatct         840
cttcctcagc acctgaagcc gccgggggac cgtcagtctt cctcttcccc ccaaaaccca        900
aggacaccct catgatctcc cggacccctg aggtcacatg cgtggtggtg gacgtgagcc        960
acgaagaccc tgaggtcaag ttcaactggt acgtggacgg cgtggaggtg cataatgcca       1020
agacaaagcc gcgggaggag cagtacaaca gcacgtaccg tgtggtcagc gtcctcaccg       1080
tcctgcacca ggactggctg aatggcaagg agtacaagtg caaggtctcc aacaaagccc       1140
tcccagcccc catcgagaaa accatctcca aagccaaagg tgggacccgt ggggtgcgag       1200
ggccacatgg acagaggccg gctcggccca ccctctgccc tgagagtgac cgctgtacca       1260
acctctgtcc ctacagggca gccccgagaa ccacaggtgt acaccctgcc cccatcccgg       1320
gaggagatga ccaagaacca ggtcagcctg acctgcctgg tcaaaggctt ctatcccagc       1380
gacatcgccg tggagtggga gagcaatggg cagccggaga caactacaa gaccacgcct        1440 cccgtgctgg actccgacgg ctccttcttc ctctatagca agctcaccgt ggacaagagc       1500
aggtggcagc aggggaacgt cttctcatgc tccgtgatgc atgaggctct gcacaaccac       1560
tacacgcaga gagcctctc cctgtccccg ggtaaa                                  1596
```

<210> SEQ ID NO 18
<211> LENGTH: 981
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
gcttccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcacctgagt tcctggggggg accatcagtc     360 ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggctc accgtggaca agagcaggtg gcaggagggg     900
aatgtcttct catgctccgt gatgcatgag gctctgcaca accactacac acagaagagc     960
ctctccctgt ctctgggtaa a                                               981

<210> SEQ ID NO 19
<211> LENGTH: 1588
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
gcttccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttggtgag     300
aggccagcac agggagggag ggtgtctgct ggaagccagg ctcagccctc ctgcctggac     360
gcaccccggc tgtgcagccc cagcccaggg cagcaaggca ggccccatct gtctcctcac     420
ccggaggcct ctgaccaccc cactcatgct caggagagg tcttctgga tttttccacc     480 aggctccggg cagccacagg ctggatgccc ctaccccagg ccctgagcat acaggggcag     540
gtgctgcgct cagacctgcc aagagccata tccggggagga ccctgcccct gacctaagcc     600 cacccccaaag gccaaactct ccactccctc agctcagaca ccttctctcc tcccagatct     660

-continued

```
gagtaactcc caatcttctc tctgcagagt ccaaatatgg tcccccatgc ccaccatgcc        720
caggtaagcc aacccaggcc tcgccctcca gctcaaggcg ggacaggtgc cctagagtag        780
cctgcatcca gggacaggcc ccagccgggt gctgacgcat ccacctccat ctcttcctca        840
gcacctgagt tcctgggggg accatcagtc ttcctgttcc ccccaaaacc caaggacact        900
ctcatgatct cccggacccc tgaggtcacg tgcgtggtgg tggacgtgag ccaggaagac        960
cccgaggtcc agttcaactg gtacgtggat ggcgtggagg tgcataatgc caagacaaag        1020
ccgcgggagg agcagttcaa cagcacgtac cgtgtggtca gcgtcctcac cgtcctgcac        1080
caggactggc tgaacggcaa ggagtacaag tgcaaggtct ccaacaaagg cctcccgtcc        1140
tccatcgaga aaaccatctc caaagccaaa ggtgggaccc acggggtgcg agggccacat        1200
ggacagaggt cagctcggcc caccctctgc cctgggagtg accgctgtgc caacctctgt        1260
ccctacaggg cagccccgag agccacaggt gtacaccctg cccccatccc aggaggagat        1320
gaccaagaac caggtcagcc tgacctgcct ggtcaaaggc ttctacccca gcgacatcgc        1380
cgtggagtgg gagagcaatg ggcagccgga gaacaactac aagaccacgc ctcccgtgct        1440
ggactccgac ggctccttct tcctctacag caggctcacc gtggacaaga gcaggtggca        1500
ggaggggaat gtcttctcat gctccgtgat gcatgaggct ctgcacaacc actacacaca        1560
gaagagcctc tccctgtctc tgggtaaa        1588
```

```
<210> SEQ ID NO 20
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
```

```
gcctccacca agggcccatc ggtcttcccc ctggcgccct gctccaggag cacctccgag        60
agcacagccg ccctgggctg cctggtcaag gactacttcc ccgaaccggt gacggtgtcg        120
tggaactcag gcgctctgac cagcggcgtg cacaccttcc cagctgtcct acagtcctca        180
ggactctact ccctcagcag cgtggtgacc gtgccctcca gcaacttcgg cacccagacc        240
tacacctgca acgtagatca caagcccagc aacaccaagg tggacaagac agttgagcgc        300
aaatgttgtg tcgagtgccc accgtgccca gcaccacctg tggcaggacc gtcagtcttc        360
ctcttccccc caaaacccaa ggacaccctc atgatctccc ggacccctga ggtcacgtgc        420
gtggtggtgg acgtgagcca cgaagacccc gaggtccagt tcaactggta cgtggacggc        480
gtggaggtgc ataatgccaa gacaaagcca cgggaggagc agttcaacag cacgttccgt        540
gtggtcagcg tcctcaccgt tgtgcaccag gactggctga acggcaagga gtacaagtgc        600
aaggtctcca acaaaggcct cccagccccc atcgagaaaa ccatctccaa aaccaaaggg        660
cagccccgag aaccacaggt gtacaccctg cccccatccc gggaggagat gaccaagaac        720
caggtcagcc tgacctgcct ggtcaaaggc ttctacccca gcgacatcgc cgtggagtgg        780
gagagcaatg ggcagccgga gaacaactac aagaccacac ctcccatgct ggactccgac        840
ggctccttct tcctctacag caagctcacc gtggacaaga gcaggtggca gcaggggaac        900
gtcttctcat gctccgtgat gcatgaggct ctgcacaacc actacacgca gaagagcctc        960
tccctgtctc cgggtaaa        978
```

<210> SEQ ID NO 21
<211> LENGTH: 1585
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
gcctccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttggtgag     300
aggccagctc agggagggag ggtgtctgct ggaagccagg ctcagccctc ctgcctggac     360
gcaccccggc tgtgcagccc cagcccaggc agcaaggca ggccccatct gtctcctcac      420
ccggaggcct ctgcccgccc cactcatgct cagggagagg gtcttctggc tttttccacc     480 aggtccagg caggcacagg ctgggtgccc ctaccccagg cccttcacac acaggggcag      540
gtgcttggct cagacctgcc aaaagccata tccgggagga ccctgcccct gacctaagcc     600
gaccccaaag gccaaactgt ccactccctc agctcggaca ccttctctcc tcccagatcc     660
gagtaactcc caatcttctc tctgcagagc gcaaatgttg tgtcgagtgc ccaccgtgcc     720
caggtaagcc agcccaggcc tcgccctcca gctcaaggcg ggacaggtgc cctagagtag     780
cctgcatcca gggacaggcc ccagctgggt gctgacacgt ccacctccat ctcttcctca     840
gcaccacctg tggcaggacc gtcagtcttc ctcttccccc caaaacccaa ggacaccctc     900
atgatctccc ggacccctga ggtcacgtgc gtggtggtgg acgtgagcca cgaagacccc     960
gaggtccagt tcaactggta cgtggacggc gtggaggtgc ataatgccaa gacaaagcca    1020
cgggaggagc agttcaacag cacgttccgt gtggtcagcg tcctcaccgt tgtgcaccag    1080
gactggctga cggcaagga gtacaagtgc aaggtctcca caaaggcct cccagcccccc    1140 atcgagaaaa ccatctccaa aaccaaaggt gggacccgcg gggtatgagg gccacatgga    1200
cagaggccgg ctcggcccac cctctgccct gggagtgacc gctgtgccaa cctctgtccc    1260
tacagggcag ccccgagaac cacaggtgta caccctgccc ccatcccggg aggagatgac    1320
caagaaccag gtcagcctga cctgcctggt caaaggcttc taccccagcg acatcgccgt    1380
ggagtgggag agcaatgggc agccggagaa caactacaag accacacctc ccatgctgga    1440
ctccgacggc tccttcttcc tctacagcaa gctcaccgtg gacaagagca ggtggcagca    1500
ggggaacgtc ttctcatgct ccgtgatgca tgaggctctg cacaaccact acacgcagaa    1560
gagcctctcc ctgtctccgg gtaaa                                         1585

<210> SEQ ID NO 22
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
cgtacggtgg ctgcaccatc tgtcttcatc ttcccgccat ctgatgagca gttgaaatct      60

```
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                               321
```

```
<210> SEQ ID NO 23
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 24
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
```

325

<210> SEQ ID NO 25
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 26

```
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
caggtgcagc tacagcagtc tggggggaggc ttggtacagc ctggggggtc cctgagactc      60
tcctgtgcag cctctggatt caccttaagc agctatgcca tgagctgggt ccgccaggct     120
ccagggaagg ggctggagtg ggtctcaggt attagtggta gtggtggtag cacatacaac     180
gcagactccg tgaagggccg gttcaccatc tccagagaca attccaagaa cacgctgttt     240
ctgcaaatga acagcctgag agccgaggac acggccgtat attactgtgc gaaaattttt     300
gggtcctact actttgacta ctggggccag ggaaccctgg tcacagtctc gagt          354

<210> SEQ ID NO 27
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gaaattgtga tgacacagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactggac atctacccgg     180
gaatccgggg tccctaaccg attcagtggc agcgggtctg ggacagattt cactctcacc     240
atcagcagcc tgcaggctga agatgtggca gtttattact gtcagcaata ttatagtggt     300
cctccgacgt tcggccaagg gaccaaggtg gaaatcaaa                            339

<210> SEQ ID NO 28
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Asn Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Ile Phe Gly Ser Tyr Tyr Phe Asp Tyr Trp Gly Gln Gly Thr
            100                 105                 110
```

```
Leu Val Thr Val Ser Ser
        115

<210> SEQ ID NO 29
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asn Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Pro Thr Phe Gly Gln Gly Thr Lys Val Glu Ile
            100                 105                 110

Lys

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Phe Thr Leu Ser Ser Tyr Ala
1               5

<210> SEQ ID NO 31
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ile Ser Gly Ser Gly Gly Ser Thr
1               5

<210> SEQ ID NO 32
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32
```

Cys Ala Lys Ile Phe Gly Ser Tyr Tyr Phe Asp Tyr Trp
1               5                   10

<210> SEQ ID NO 33
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gln Ser Val Leu Tyr Ser Ser Asn Asn Lys Asn Tyr
1               5                   10

<210> SEQ ID NO 34
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Trp Thr Ser
1

<210> SEQ ID NO 35
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Cys Gln Gln Tyr Tyr Ser Gly Pro Pro Thr Phe
1               5                   10

<210> SEQ ID NO 36
<211> LENGTH: 377
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
acgtgacagg gcgcgcccag gtccagctgc aggagagcgg tcccggactg gtgaagccat        60
cccagacact gagcctgact tgtactgtga gcggcggtag catctccagc ggcggctact       120
attggtcctg gatcaggcag cacccaggca agggcctgga gtggatcggc tacatctact       180
atagcggctc tatctactat aacccttccc tgaagagccg ggtgaccatc tctgtggaca       240
catccaagaa tcagttctat ctgaagctgt cttccgtgac cgccgctgat acagccgtgt       300
actattgcgc ctcactgatg gtctgggggg tcatgggcga ttactggggg cagggcacac       360
tggtcacagt ctcgagt                                                      377

<210> SEQ ID NO 37
<211> LENGTH: 321
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
gagattgtgc tgacccagtc tcccgccacc ctgtctctga gtcctggcga gagagccacc      60
ctgagctgca gagcctctca gtccgtgtcc agctatctgg cctggtatca gcagaagccc     120
ggccaggctc cccggctgct gatctacgat gcctccaata gagccaccgg catccctgcc     180
agattctccg gctctggctc tggcaccgac tttaccctga ccatctccag cctggaaccc     240
gaggacttcg ccgtgtacta ctgccagcag cggtccgact ggcctcctac atttggccaa     300
ggcaccaagg tggaaatcaa g                                               321
```

<210> SEQ ID NO 38
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Ile Tyr Tyr Asn Pro Ser
    50                  55                  60

Leu Lys Ser Arg Val Thr Ile Ser Val Asp Thr Ser Lys Asn Gln Phe
65                  70                  75                  80

Tyr Leu Lys Leu Ser Ser Val Thr Ala Ala Asp Thr Ala Val Tyr Tyr
                85                  90                  95

Cys Ala Ser Leu Met Val Trp Gly Val Met Gly Asp Tyr Trp Gly Gln
            100                 105                 110

Gly Thr Leu Val Thr Val Ser Ser
        115                 120
```

<210> SEQ ID NO 39
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Pro
                85                  90                  95

Thr Phe Gly Gln Gly Thr Lys Val Glu Ile Lys
            100                 105

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Gly Ser Ile Ser Ser Gly Gly Tyr Tyr
1               5                   10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ile Tyr Tyr Ser Gly Ser Ile
1               5

<210> SEQ ID NO 42
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Cys Ala Ser Leu Met Val Trp Gly Val Met Gly Asp Tyr Trp
1               5                   10

<210> SEQ ID NO 43
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gln Ser Val Ser Ser Tyr
1               5

<210> SEQ ID NO 44
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 44

Asp Ala Ser
1

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Cys Gln Gln Arg Ser Asp Trp Pro Pro Thr Phe
1               5                   10

<210> SEQ ID NO 46
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46
caggtcacct tgaaggagtg gggcgcagga ctgttgaggc cctcggagac cctgtccctc      60
acctgcgctg tctatggtgg gtccttcagt ggttactact ggagctggat ccgccagccc     120
ccagggaagg ggctggagtg gataggggaa atcaatcata gtggaagcac caactacaac     180
ccgtccctca agagtcgagt caccatatca gtagacgcga ccaagaaaca attctccctg     240
aagctgacct ctgtgaccgc cgcggacacg gctgtgtatt actgtgcgag atattgggag     300
ctccctgact actggggcca gggcaccctg gtcaccgtct cgagt                     345

<210> SEQ ID NO 47
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47
gacatccagt tgacccagtc tccatcctcc ctgtctgcat ctgtaggaga cagagtcacc      60
atcacttgcc gggcaagtca gggcattaga aatgatttag ctggtatca gcagaaacca      120 gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctccgac gttcggccaa     300
gggaccaagg tggaaatcaa g                                               321

<210> SEQ ID NO 48
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

<400> SEQUENCE: 48

Gln Val Thr Leu Lys Glu Trp Gly Ala Gly Leu Leu Arg Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Ala Thr Lys Lys Gln Phe Ser Leu
65                  70                  75                  80

Lys Leu Thr Ser Val Thr Ala Ala Asp Thr Ala Val Tyr Tyr Cys Ala
            85                  90                  95

Arg Tyr Trp Glu Leu Pro Asp Tyr Trp Gly Gln Gly Thr Leu Val Thr
        100                 105                 110

Val Ser Ser
        115

<210> SEQ ID NO 49
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
            85                  90                  95

Thr Phe Gly Gln Gly Thr Lys Val Glu Ile Lys
        100                 105

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gly Gly Ser Phe Ser Gly Tyr Tyr
1               5

<210> SEQ ID NO 51
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ile Asn His Ser Gly Ser Thr
1               5

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Cys Ala Arg Tyr Trp Glu Leu Pro Asp Tyr Trp
1               5                   10

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gln Gly Ile Arg Asn Asp
1               5

<210> SEQ ID NO 54
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ala Ala Ser
1

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Cys Leu Gln His Asn Ser Tyr Pro Pro Thr Phe
1               5                   10

<210> SEQ ID NO 56
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
cagatgcagc tggtgcagtg gggcgcagga ctgttgaagc cttcggagac cctgtccctc          60
acctgcgctg tctatggtgg gtccttcagt ggttactact ggagctggat ccgccagccc         120
ccagggaagg ggctggagtg gattggggaa atcaatcata gtggaagcac caactacaac         180
ccgtccctca agagtcgagt caccatgtca gttgacacgt ccaagcacca gttctccctg         240
aagctgagct ctgtgaccgc cgcggacacg gctgtgtatt actgtgcgag atggtgggag         300
cttcctgact actggggcca gggaaccctg gtcaccgtct cgagt                        345

<210> SEQ ID NO 57
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
gaaattgtgt tgacgcagtc tccatcctcc ctgtctgcat ctgtaggaga cagagtcacc          60
atcacttgcc gggcaagtca gggcattaga aatgatttag ctggtatca gcagaaacca         120 gggaaagccc ctaagcgcct gatctatgct gcatccagtt tgcaaagtgg ggtcccatca         180
aggttcagcg gcagtggatc tgggacagaa ttcactctca caatcagcag cctgcagcct         240
gaagattttg caacttatta ctgtctacag cataatagtt acccgtggac gttcggccaa         300
gggaccaagg tggaaatcaa g                                                   321

<210> SEQ ID NO 58
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Met Gln Leu Val Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Met Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Trp Trp Glu Leu Pro Asp Tyr Trp Gly Gln Gly Thr Leu Val Thr
            100                 105                 110

Val Ser Ser
        115

<210> SEQ ID NO 59
<211> LENGTH: 107
<212> TYPE: PRT

-continued

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

```
Gly Gly Ser Phe Ser Gly Tyr Tyr
1               5
```

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

```
Ile Asn His Ser Gly Ser Thr
1               5
```

<210> SEQ ID NO 62
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

```
Cys Ala Arg Trp Trp Glu Leu Pro Asp Tyr Trp
1               5                   10
```

<210> SEQ ID NO 63
<211> LENGTH: 6
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic peptide"

<400> SEQUENCE: 63

Gln Gly Ile Arg Asn Asp
1               5

<210> SEQ ID NO 64
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ala Ala Ser
1

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Cys Leu Gln His Asn Ser Tyr Pro Trp Thr Phe
1               5                   10

<210> SEQ ID NO 66
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
cagatgcagc tggtgcaatg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcgag gttttactat     300
gctccgaact ttgactactg gggccagggc accctggtca ccgtctcgag t               351

<210> SEQ ID NO 67
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
gaaattgtgt tgacgcagtc tccttccacc ctgtctgcat ctgtaggaga cagagtcacc      60
atcacttgcc gggccagtca gagtattagt agctggttgg cctggtatca gcagaaacca     120
```

-continued

```
gggacagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attccacttt cggcggaggg    300
accaaggtgg agatcaaa                                                   318
```

```
<210> SEQ ID NO 68
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Gln Met Gln Leu Val Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Phe Tyr Tyr Ala Pro Asn Phe Asp Tyr Trp Gly Gln Gly Thr Leu
            100                 105                 110

Val Thr Val Ser Ser
        115
```

```
<210> SEQ ID NO 69
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Thr Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gly Gly Thr Lys Val Glu Ile Lys
            100                 105
```

```
<210> SEQ ID NO 70
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gly Gly Ser Phe Ser Gly Tyr Tyr
1               5

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ile Asn His Ser Gly Ser Thr
1               5

<210> SEQ ID NO 72
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Cys Ala Arg Phe Tyr Tyr Ala Pro Asn Phe Asp Tyr Trp
1               5                   10

<210> SEQ ID NO 73
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Ser Ile Ser Ser Trp
1               5

<210> SEQ ID NO 74
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Lys Ala Ser
1

<210> SEQ ID NO 75
<211> LENGTH: 10
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 75

Cys Gln Gln Tyr Asn Ser Tyr Ser Thr Phe
1               5                   10

<210> SEQ ID NO 76
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
caggtgcagc tgcagcagtc gggcccagga ctggtgaagc cttcggagac cctgtccctc        60
acctgcactg tctctggtgg ctccatcagc agtagtaatt actactgggg ctggatccgc       120
cagcccccag ggaagggget ggagtggatt gggagtatct attatagtgg gaacacctac       180
tacaacccgt ccctcaagag tcgagtcacc atatccgtag acacgtccaa gaaccagttc       240
tccctgaagc tgagttctgt gaccgccgca gacacggctg tgtattactg tgcgagacag       300
acagtggctg gcccctctt tgactactgg ggccagggaa ccctggtcac cgtctcgagt        360

<210> SEQ ID NO 77
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77
gaaattgtga tgacgcagtc tccttccacc ctgtctgcat ctgtaggaga cagagtcacc        60
atcacttgcc gggccagtca gagtattagt agctggttgg cctggtatca gcagaaacca       120
gggaaagccc ctaaggtcct gatctataag gcgtctagtt tagaaagtgg ggtcccatca       180
aggttcagcg gcagtggatc tgggacagaa ctcactctca ccatcagcag cctgcagcct       240
gatgattttg caacttatta ctgccaacag tataatagtt attcattcac tttcggccct       300
gggaccaaag tggatatcaa g                                                 321

<210> SEQ ID NO 78
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Asn Tyr Tyr Trp Gly Trp Ile Arg Gln Pro Pro Gly Lys Gly Leu Glu
        35                  40                  45

```
Trp Ile Gly Ser Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Thr Val Ala Gly Pro Leu Phe Asp Tyr Trp Gly Gln
            100                 105                 110

Gly Thr Leu Val Thr Val Ser Ser
        115                 120

<210> SEQ ID NO 79
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Leu Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Thr Phe Gly Pro Gly Thr Lys Val Asp Ile Lys
            100                 105

<210> SEQ ID NO 80
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly Gly Ser Ile Ser Ser Ser Asn Tyr Tyr
1               5                   10

<210> SEQ ID NO 81
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Ile Tyr Tyr Ser Gly Asn Thr
1               5
```

-continued

```
<210> SEQ ID NO 82
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Cys Ala Arg Gln Thr Val Ala Gly Pro Leu Phe Asp Tyr Trp
1               5                   10

<210> SEQ ID NO 83
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Ser Ile Ser Ser Trp
1               5

<210> SEQ ID NO 84
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Lys Ala Ser
1

<210> SEQ ID NO 85
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Cys Gln Gln Tyr Asn Ser Tyr Ser Phe Thr Phe
1               5                   10

<210> SEQ ID NO 86
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
caggtccagc tggtgcaatc tggggctgag gtgaagaagc ctggggcctc agtgaaggtc      60
tcctgcaagg ctgctggata caccttaacc ggctactata tgcactgggt gcgacaggcc     120
cctggacaag gccttgagtg gatgggacgg atcaacccta acagtggtgg ctcaaacaat     180
gcacagaagt ttcagggcag ggtcaccatg accagggaca cgtccatcag cacagcctac     240
```

-continued

```
atggagctga gcaggctgag atctgacgac acggccgtgt attactgtgc gagagagggt      300
cccctgtata gcagtggctg gtacgagggt gcttttgata tctggggcca agggacaatg      360
gtcaccgtct cgagt                                                       375
```

<210> SEQ ID NO 87
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 87

```
gaaattgtga tgacgcagtc tccttccacc ctgtctgcat ctgtaggaga cagagtcacc       60
atcacttgcc gggccagtca gagtattagt agttggttgg cctggtatca gcagaaacca      120
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tataatagtt attctccggg gctcactttc      300
ggcggaggga ccaaggtgga gatcaag                                          327
```

<210> SEQ ID NO 88
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Leu Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Ser Asn Asn Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Pro Leu Tyr Ser Ser Gly Trp Tyr Glu Gly Ala Phe
            100                 105                 110

Asp Ile Trp Gly Gln Gly Thr Met Val Thr Val Ser Ser
        115                 120                 125
```

<210> SEQ ID NO 89
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 89

```
Glu Ile Val Met Thr Gln Ser Pro Ser Thr Leu Ser Ala Ser Val Gly
```

-continued

```
1                5                10               15

Asp Arg Val Thr Ile Thr Cys Arg Ala Ser Gln Ser Ile Ser Ser Trp
             20               25               30

Leu Ala Trp Tyr Gln Gln Lys Pro Gly Lys Ala Pro Lys Leu Leu Ile
         35               40               45

Tyr Lys Ala Ser Ser Leu Glu Ser Gly Val Pro Ser Arg Phe Ser Gly
     50               55               60

Ser Gly Ser Gly Thr Glu Phe Thr Leu Thr Ile Ser Ser Leu Gln Pro
65               70               75               80

Asp Asp Phe Ala Thr Tyr Tyr Cys Gln Gln Tyr Asn Ser Tyr Ser Pro
                 85               90               95

Gly Leu Thr Phe Gly Gly Gly Thr Lys Val Glu Ile Lys
             100              105
```

```
<210> SEQ ID NO 90
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gly Tyr Thr Leu Thr Gly Tyr Tyr
1               5

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ile Asn Pro Asn Ser Gly Gly Ser
1               5

<210> SEQ ID NO 92
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Cys Ala Arg Glu Gly Pro Leu Tyr Ser Ser Gly Trp Tyr Glu Gly Ala
1               5                10               15

Phe Asp Ile Trp
            20

<210> SEQ ID NO 93
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93
```

Gln Ser Ile Ser Ser Trp
1               5

<210> SEQ ID NO 94
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Lys Ala Ser
1

<210> SEQ ID NO 95
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Cys Gln Gln Tyr Asn Ser Tyr Ser Pro Gly Leu Thr Phe
1               5                   10

<210> SEQ ID NO 96
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
cagatgcagc tacagcagtc aggtccagga ctggtgaagc cctcgcagac cctctcactc        60
acctgtgcca tctccgggga cagtgtctct agcaacagtg ctgcttggaa ctggatcagg       120
cagtccccat cgagaggcct tgagtggctg ggaaggacat actacaggtc caagtggtat       180
tctgcttttg cagtatctgt gaaaagtcga ataaccatca acccagacac atccaagaac       240
cagttctccc tgcagctgaa ctctgtgact cccgaggaca cggctgtgta ttactgtgca       300
agagagggta gcagtggctg gtacggatac gtccaccact ggggccaggg caccctggtc       360
accgtctcga gt                                                           372

<210> SEQ ID NO 97
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gaaattgtgt tgacgcagtc tccagcttcc ctgtctgtat ctctgggaga aactgtcacc        60
atcgaatgtc gagcaagtga ggacatttac aatggtttag catggtatca gcagaagcca       120
gggaaatctc ctcagctcct gatctataat gcaaatagct tgcatactgg ggtcccatca       180
cggttcagtg gcagtggatc tggtacacag tattctctca agataaacag cctgcaatct       240
gaagatgtcg caagttattt ctgtcaacag tattacgatt atcctccgac gttcggccaa          300
gggaccaagg tggaaatcaa a                                                    321

<210> SEQ ID NO 98
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Met Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Ala Phe Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Ser Ser Gly Trp Tyr Gly Tyr Val His
            100                 105                 110

His Trp Gly Gln Gly Thr Leu Val Thr Val Ser Ser
        115                 120

<210> SEQ ID NO 99
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Glu Ile Val Leu Thr Gln Ser Pro Ala Ser Leu Ser Val Ser Leu Gly
1               5                   10                  15

Glu Thr Val Thr Ile Glu Cys Arg Ala Ser Glu Asp Ile Tyr Asn Gly
            20                  25                  30

Leu Ala Trp Tyr Gln Gln Lys Pro Gly Lys Ser Pro Gln Leu Leu Ile
        35                  40                  45

Tyr Asn Ala Asn Ser Leu His Thr Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Tyr Asp Tyr Pro Pro
                85                  90                  95

Thr Phe Gly Gln Gly Thr Lys Val Glu Ile Lys
            100                 105

<210> SEQ ID NO 100
<211> LENGTH: 10
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 100

Gly Asp Ser Val Ser Ser Asn Ser Ala Ala
1               5                   10

<210> SEQ ID NO 101
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Thr Tyr Tyr Arg Ser Lys Trp Tyr Ser
1               5

<210> SEQ ID NO 102
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Cys Ala Arg Glu Gly Ser Ser Gly Trp Tyr Gly Tyr Val His His Trp
1               5                   10                  15

<210> SEQ ID NO 103
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Glu Asp Ile Tyr Asn Gly
1               5

<210> SEQ ID NO 104
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Asn Ala Asn
1

<210> SEQ ID NO 105
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 105

Cys Gln Gln Tyr Tyr Asp Tyr Pro Pro Thr Phe
1               5                   10

<210> SEQ ID NO 106
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
caggtgcagc tgcaggagtc gggcccagga ctggtgaagc cttcggagac cctgtccctc      60
acctgcactg tctctggtgg ctccttcagc agtagtagtt actactgggg ctggatccgc     120
cagccccctg ggaaggggct ggagtggatt gggatcttct attatagtgg gaccacctac     180
tacaacccgt ccctcaagag tcgagtcacc atatccgcac acacgtccaa gagccagttc     240
tccctgaagc tgagctctgt gaccgccgca gacacggctg tgtattactg tgcgagaggg     300
ggagaatatt ttgaccggtt actccccttt gactactggg gccagggaac cctggtcacc     360
gtctcgagt                                                            369

<210> SEQ ID NO 107
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107
gaaattgtga tgacgcagtc tccatccttc ctgtctgcat ctgtaggaga cagagtcacc      60
atcacttgcc gggccagtca gggcattagc agttatttag cctggtatca gcaaaaacca     120
gggaaagccc ctaagctcct gatctatgct gcatccactt tggaaagtgg ggtcccatca     180
aggttcagcg gcagtggatc tgggacagaa ttcactctca caatcagcag cctgcagcct     240
gaagattttg caacttatta ctgtcaacag cttaatagtt acccattcac tttcggccct     300
gggaccaaag tggatatcaa a                                                321

<210> SEQ ID NO 108
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ile Phe Tyr Tyr Ser Gly Thr Thr Tyr Tyr Asn Pro Ser
    50                  55                  60

```
Leu Lys Ser Arg Val Thr Ile Ser Ala His Thr Ser Lys Ser Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Glu Tyr Phe Asp Arg Leu Leu Pro Phe Asp Tyr
            100                 105                 110

Trp Gly Gln Gly Thr Leu Val Thr Val Ser Ser
        115                 120
```

```
<210> SEQ ID NO 109
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Glu Ile Val Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Pro Gly Thr Lys Val Asp Ile Lys
            100                 105
```

```
<210> SEQ ID NO 110
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Gly Gly Ser Phe Ser Ser Ser Ser Tyr Tyr
1               5                   10
```

```
<210> SEQ ID NO 111
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Phe Tyr Tyr Ser Gly Thr Thr
1               5
```

```
<210> SEQ ID NO 112
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Cys Ala Arg Gly Gly Glu Tyr Phe Asp Arg Leu Leu Pro Phe Asp Tyr
1               5                   10                  15

Trp

<210> SEQ ID NO 113
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gln Gly Ile Ser Ser Tyr
1               5

<210> SEQ ID NO 114
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ala Ala Ser
1

<210> SEQ ID NO 115
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Cys Gln Gln Leu Asn Ser Tyr Pro Phe Thr Phe
1               5                   10

<210> SEQ ID NO 116
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116
caggtgcagc tggtggagtc tgggggaggc ttggtacagc cggggggggtc cctgagactc     60 tcctgtacag cctctggatt cacctttagc agctatgcca tgagctgggt ccgccaggct    120
ccagggaagg ggctggagtg ggtctcagct attggtggta gtggtggtag cacatactac    180
gcagactccg tgaagggccg gttcaccatc tccagagaca attccaagaa cacgctgtat    240
```

-continued ctgcaaatga acagcctgag agccgaggac acggccgtat attactgtgt gaaagatggg      300
gcaggaggct ttgactactg gggccaggga accctggtca ccgtctcgag t              351

<210> SEQ ID NO 117
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
gatattgtga tgacgcagtc ttcatcctcc ctgtctgcat ctgtaggaga cagagtcacc       60
atcacttgcc gggcaagtca gggcattata aatcatttag ctggtatca gcataaacca      120 gggaaagccc ctaatcgcct aatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacgg cataatagtt accctccgac gttcggccaa      300
gggaccaagg tggaaatcaa g                                               321

<210> SEQ ID NO 118
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Gly Ala Gly Gly Phe Asp Tyr Trp Gly Gln Gly Thr Leu
            100                 105                 110

Val Thr Val Ser Ser
        115

<210> SEQ ID NO 119
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Asp Ile Val Met Thr Gln Ser Ser Ser Ser Leu Ser Ala Ser Val Gly
1               5                   10                  15

```
Asp Arg Val Thr Ile Thr Cys Arg Ala Ser Gln Gly Ile Ile Asn His
            20                  25                  30

Leu Gly Trp Tyr Gln His Lys Pro Gly Lys Ala Pro Asn Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Arg His Asn Ser Tyr Pro Pro
                85                  90                  95

Thr Phe Gly Gln Gly Thr Lys Val Glu Ile Lys
            100                 105
```

```
<210> SEQ ID NO 120
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gly Phe Thr Phe Ser Ser Tyr Ala
1               5
```

```
<210> SEQ ID NO 121
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ile Gly Gly Ser Gly Gly Ser Thr
1               5
```

```
<210> SEQ ID NO 122
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Cys Val Lys Asp Gly Ala Gly Gly Phe Asp Tyr Trp
1               5                   10
```

```
<210> SEQ ID NO 123
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Gln Gly Ile Ile Asn His
1               5
```

<210> SEQ ID NO 124
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Ala Ala Ser
1

<210> SEQ ID NO 125
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Cys Leu Arg His Asn Ser Tyr Pro Pro Thr Phe
1               5                   10

<210> SEQ ID NO 126
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126
caggtgcagc tacagcagtc gggcccagga ctggtgaagc cttcacagac cctgtccctc        60
acctgcactg tctctggtgg ctccatcaac agtggtggtc actactggag ctggatccgc       120
cagcacccag ggaggggcct ggagtggatt gggtacatct attacagtgg gagcatctac       180
tacaacccgt ccctcaagag tcgacttacc atatcagtag acacgtctaa gaaccagttc       240
tccctgaagc tgagctctgt gactgccgcg gacacggccg tgtattactg tgcgagttat       300
tactatgcca gtagtggtga tgcttttgat atctggggcc aagggacaat ggtcaccgtc       360
tcgagt                                                                  366

<210> SEQ ID NO 127
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127
gaaacgacac tcacgcagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg cagtttatta ctgtcagcag cgtagcaact ggcctccgac gttcggccaa       300
gggaccaagg tggaaatcaa a                                                  321

-continued

<210> SEQ ID NO 128
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Gln Val Gln Leu Gln Gln Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly His Tyr Trp Ser Trp Ile Arg Gln His Pro Gly Arg Gly Leu Glu
        35                  40                  45

Trp Ile Gly Tyr Ile Tyr Tyr Ser Gly Ser Ile Tyr Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Tyr Tyr Tyr Ala Ser Ser Gly Asp Ala Phe Asp Ile Trp
                100                 105                 110

Gly Gln Gly Thr Met Val Thr Val Ser Ser
            115                 120

<210> SEQ ID NO 129
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
                100                 105

<210> SEQ ID NO 130
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 130

Gly Gly Ser Ile Asn Ser Gly Gly His Tyr
1               5                   10

<210> SEQ ID NO 131
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Ile Tyr Tyr Ser Gly Ser Ile
1               5

<210> SEQ ID NO 132
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Cys Ala Ser Tyr Tyr Tyr Ala Ser Ser Gly Asp Ala Phe Asp Ile Trp
1               5                   10                  15

<210> SEQ ID NO 133
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Gln Ser Val Ser Ser Tyr
1               5

<210> SEQ ID NO 134
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Asp Ala Ser
1

<210> SEQ ID NO 135
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Cys Gln Gln Arg Ser Asn Trp Pro Pro Thr Phe
1               5                   10
```

```
<210> SEQ ID NO 136
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136
caggtgcagc tgcaggagtc tggggggaggc ttggtacagc cggggggggtc cctgagactc      60 tcctgtacag cctctggatt caccttttagt aattatgcca tgagctgggt ccgccaggct     120
ccagggaagg ggctggagtg ggtctcagct attagtggtc gtggtggtag cacattcttc     180
gcagactccg tgaagggccg gttcaccatc tccagagaca attccaagag cacgctgtat     240
ctgcaaacga acagcctgag agccgaggac acggccgtat attactgtgc gaaaggggggc     300 ccgttgtata actggaacga cggtgatggt tttgatatct ggggccaagg gaccacggtc     360
acagtctcga gt                                                         372

<210> SEQ ID NO 137
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 137
gaaattgtgt tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcactgggtc tgggacagag ttcactctca ccatcagcag cctgcagtct     240
gaagattttg cactttatta ctgtcagcag tatgataact ggcctccgtg gacgttcggc     300
caagggacca aggtggaaat caaa                                            324

<210> SEQ ID NO 138
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Ser Thr Phe Phe Ala Asp Ser Val
    50                  55                  60

Lys Gly Arg Phe Thr Ile Ser Arg Asp Asn Ser Lys Ser Thr Leu Tyr
65                  70                  75                  80

Leu Gln Thr Asn Ser Leu Arg Ala Glu Asp Thr Ala Val Tyr Tyr Cys
```

-continued

```
                    85                  90                  95

Ala Lys Gly Gly Pro Leu Tyr Asn Trp Asn Asp Gly Asp Gly Phe Asp
            100                 105                 110

Ile Trp Gly Gln Gly Thr Thr Val Thr Val Ser Ser
        115                 120
```

<210> SEQ ID NO 139
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Thr Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asp Asn Trp Pro Pro
                85                  90                  95

Trp Thr Phe Gly Gln Gly Thr Lys Val Glu Ile Lys
            100                 105
```

<210> SEQ ID NO 140
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

```
Gly Phe Thr Phe Ser Asn Tyr Ala
1               5
```

<210> SEQ ID NO 141
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

```
Ile Ser Gly Arg Gly Gly Ser Thr
1               5
```

<210> SEQ ID NO 142
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 142

Cys Ala Lys Gly Gly Pro Leu Tyr Asn Trp Asn Asp Gly Asp Gly Phe
1               5                   10                  15

Asp Ile Trp

<210> SEQ ID NO 143
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Gln Ser Val Ser Ser Asn
1               5

<210> SEQ ID NO 144
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Gly Ala Ser
1

<210> SEQ ID NO 145
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Cys Gln Gln Tyr Asp Asn Trp Pro Pro Trp Thr Phe
1               5                   10

<210> SEQ ID NO 146
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 146
caggtgcagc tgcaggagtc tgggggaggc ttggtcaagc ctggagggtc cctgagactc      60
tcctgtgcag cctctggatt caccttcagt gactactaca tgacctggat ccgccaggct     120
ccagggaagg ggctggagtg gatttcatac attagtggtg gtggtggttc catatactac     180
gcagactctg tgaagggccg attcaccatc tccagggaca cgccaagaa ctcactgtat      240 ctgcaaatga acagcctgag agccgaggac acggccgttt atttctgtgc gagagggaac     300
tggggatcgg cggctcttga tatctggggc caagggacaa tggtcacggt ctcgagt        357

-continued

```
<210> SEQ ID NO 147
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 147
gaaattgtgt tgacgcagtc tccatcctca ctgtctgcat ctgtaggaga cagagtcacc      60
atcacttgtc gggcgagtca gggcattaac aattatttag cctggtttca gcagaaacca     120
gggagagccc ctaagtccct gatctatgct gcatccagtt tgcaaagtgg ggtcccatcg     180
aagttcagcg gcagtggatc tgggacagat ttcactctca ccatcagcag cctgcagcct     240
gaagattttg caacttatta ctgccaacag tataatagtt accctccaac tctcggccct     300
gggaccaacg tggatatcaa a                                                321

<210> SEQ ID NO 148
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Ile
        35                  40                  45

Ser Tyr Ile Ser Gly Gly Gly Gly Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Gly Asn Trp Gly Ser Ala Ala Leu Asp Ile Trp Gly Gln Gly
            100                 105                 110

Thr Met Val Thr Val Ser Ser
        115

<210> SEQ ID NO 149
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Arg Ala Pro Lys Ser Leu Ile
        35                  40                  45
```

```
Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Leu Gly Pro Gly Thr Asn Val Asp Ile Lys
            100                 105
```

```
<210> SEQ ID NO 150
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Gly Phe Thr Phe Ser Asp Tyr Tyr
1               5

<210> SEQ ID NO 151
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Ile Ser Gly Gly Gly Gly Ser Ile
1               5

<210> SEQ ID NO 152
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Cys Ala Arg Gly Asn Trp Gly Ser Ala Ala Leu Asp Ile Trp
1               5                   10

<210> SEQ ID NO 153
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Gln Gly Ile Asn Asn Tyr
1               5

<210> SEQ ID NO 154
<211> LENGTH: 3
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 154

Ala Ala Ser
1

<210> SEQ ID NO 155
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Cys Gln Gln Tyr Asn Ser Tyr Pro Pro Thr Leu
1               5                   10

<210> SEQ ID NO 156
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
caggtgcagc tggtggagtc tgggggaggc ttggtacagc cggggggggtc cctgagactc      60 tcctgtacag cctctggatt caccttttagc agctatgcca tgagctgggt ccgccaggct     120
ccagggaagg ggctggagtg ggtctcagct attggtggta gtggtggtag cgcatactac     180
gcagactccg tgaagggccg gttcaccatc tccagagaca attccaagaa cacgctgtat     240
ctgcaaatga acagcctgag agccgaggac acggccgtat attactgtgt gaaagatggg     300
gcaggaggct ttgactactg gggccagggc accctggtca ccgtctcgag t               351

<210> SEQ ID NO 157
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157
gacatccagt tgacccagtc cccatcctcc ctgtctgcat ctgtaggaga cagagtcacc      60
atcacttgcc gggcaagtca gggcattaga aatcatttag ctggtatca gcagaaacca     120 gggaaagccc ctaagcgcct aatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctccgac gttcggccaa     300
gggaccaagg tggaaatcaa g                                                321

<210> SEQ ID NO 158
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 158

Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Gly Ala Gly Gly Phe Asp Tyr Trp Gly Gln Gly Thr Leu
            100                 105                 110

Val Thr Val Ser Ser
        115

<210> SEQ ID NO 159
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 159

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn His
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys
            100                 105

<210> SEQ ID NO 160
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 160

Gly Phe Thr Phe Ser Ser Tyr Ala
1               5

<210> SEQ ID NO 161

<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Ile Gly Gly Ser Gly Gly Ser Ala
1               5

<210> SEQ ID NO 162
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Cys Val Lys Asp Gly Ala Gly Gly Phe Asp Tyr Trp
1               5                   10

<210> SEQ ID NO 163
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Gln Gly Ile Arg Asn His
1               5

<210> SEQ ID NO 164
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Ala Ala Ser
1

<210> SEQ ID NO 165
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Cys Leu Gln His Asn Ser Tyr Pro Pro Thr Phe
1               5                   10

<210> SEQ ID NO 166
<211> LENGTH: 354
<212> TYPE: DNA
<213> ORGANISM: Artificial Sequence
<220> FEATURE:

-continued

```
<221> NAME/KEY: source
<223> OTHER INFORMATION: /note="Description of Artificial Sequence:
      Synthetic polynucleotide"

<400> SEQUENCE: 166
cagatgcagc tacagcagtc tgggggaggc ttggtacagc cggggggggtc cctgagactc      60 tcctgtgcag cctctggatt caccgttagc agctatgcca tgagctgggt ccgccaggct     120
ctagggaagg ggctggagtg ggtctcaggt attagtggta gtggtggtag cacatactac     180
gcagactccg tgaagggccg gttcaccatc tccagagaca attccaagaa tacgctgtat     240
ctgcaaatga acagcctgag agccgaggac acggccgtat attactgtgc gaagatagtg     300
ggagctaccc actttgacta ctggggccag ggaaccctgg tcacggtctc gagt          354

<210> SEQ ID NO 167
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 167
gaaattgtga tgacacagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtggt     300
ccgatcacct tcggccaagg gacacgactg gagattaag                           339

<210> SEQ ID NO 168
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Gln Met Gln Leu Gln Gln Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Ala Met Ser Trp Val Arg Gln Ala Leu Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Val Gly Ala Thr His Phe Asp Tyr Trp Gly Gln Gly Thr
            100                 105                 110

Leu Val Thr Val Ser Ser
        115
```

```
<210> SEQ ID NO 169
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Ile Thr Phe Gly Gln Gly Thr Arg Leu Glu Ile
            100                 105                 110

Lys

<210> SEQ ID NO 170
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Gly Phe Thr Val Ser Ser Tyr Ala
1               5

<210> SEQ ID NO 171
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Ile Ser Gly Ser Gly Gly Ser Thr
1               5

<210> SEQ ID NO 172
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Cys Ala Lys Ile Val Gly Ala Thr His Phe Asp Tyr Trp
1               5                   10
```

<210> SEQ ID NO 173
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Gln Ser Val Leu Tyr Ser Ser Asn Asn Lys Asn Tyr
1               5                   10

<210> SEQ ID NO 174
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Trp Ala Ser
1

<210> SEQ ID NO 175
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Cys Gln Gln Tyr Tyr Ser Gly Pro Ile Thr Phe
1               5                   10

<210> SEQ ID NO 176
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 176
caggtgcagc tggtggagtc gggcccagga ctggtgaagc cttcacagac cctgtccctc      60
acctgcactg tctctggtgg ctccatcaac agtggtggtt actactggag ctggatccgc     120
cagcacccag ggaagggcct ggagtggatt gggtacatct attacagtgg gagcatctac     180
tacaacccgt ccctcaggag tcgacttacc atatcagtag acacgtctaa gaaccagttc     240
tccctgaagc tgagctctgt gactgccgcg gacacggccg tttattactg tgcgactcct     300
tattactatg gttcggggag ttatggggac tactggggcc agggcaccct ggtcactgtc     360
tcgagt                                                                366

<210> SEQ ID NO 177
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 177
gacatccaga tgacccagtc tccagccacc ctgtctttgt ctccagggga aagagccacc      60
ctctcctgca gggccagtca gagtgttaac aactacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcccatcac cttcggccaa     300
gggacacgac tggagattaa a                                               321

<210> SEQ ID NO 178
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Ile Tyr Tyr Asn Pro Ser
    50                  55                  60

Leu Arg Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Thr Pro Tyr Tyr Tyr Gly Ser Gly Ser Tyr Gly Asp Tyr Trp
            100                 105                 110

Gly Gln Gly Thr Leu Val Thr Val Ser Ser
        115                 120

<210> SEQ ID NO 179
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

-continued

```
Glu Asp Phe Ala Val Tyr Tyr Cys Gln Gln Arg Ser Asn Trp Pro Ile
            85                  90                  95

Thr Phe Gly Gln Gly Thr Arg Leu Glu Ile Lys
            100                 105

<210> SEQ ID NO 180
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Gly Gly Ser Ile Asn Ser Gly Gly Tyr Tyr
1               5                   10

<210> SEQ ID NO 181
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Ile Tyr Tyr Ser Gly Ser Ile
1               5

<210> SEQ ID NO 182
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Cys Ala Thr Pro Tyr Tyr Tyr Gly Ser Gly Ser Tyr Gly Asp Tyr Trp
1               5                   10                  15

<210> SEQ ID NO 183
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Gln Ser Val Asn Asn Tyr
1               5

<210> SEQ ID NO 184
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Asp Ala Ser
```

-continued

1

<210> SEQ ID NO 185
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Cys Gln Gln Arg Ser Asn Trp Pro Ile Thr Phe
1               5                   10

<210> SEQ ID NO 186
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 186
cagatgcagc tgcaggagtc gggcccagga ctggtgaagc cttctcagac cctgtccctc      60
acctgcactg tgtctggtgg ctccatcagc agtgttggtt actactggaa ctggatccgc     120
cagcacccag ggaagggcct ggagttcatt gggtacatct attacagtgg gagcatctac     180
tacaatccgt ccctcaagag tcgagttacc atatccgtag acacgtctaa gaaccagttc     240
tccctgaagc tgagctctgt gactgccgcg gacacggccc tatattactg tgcgagcgtc     300
ggtatagtgg gagcctccta ctttgagtac tggggccagg gaaccctggt cacagtctcg     360
agt                                                                   363

<210> SEQ ID NO 187
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 187
gaaattgtga tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctatcac cttcggccaa     300
gggacacgac tggagatcaa g                                               321

<210> SEQ ID NO 188
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

```
Gln Met Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Val
            20                  25                  30

Gly Tyr Tyr Trp Asn Trp Ile Arg Gln His Pro Gly Lys Gly Leu Glu
        35                  40                  45

Phe Ile Gly Tyr Ile Tyr Tyr Ser Gly Ser Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Leu Tyr Tyr
                85                  90                  95

Cys Ala Ser Val Gly Ile Val Gly Ala Ser Tyr Phe Glu Tyr Trp Gly
            100                 105                 110

Gln Gly Thr Leu Val Thr Val Ser Ser
        115                 120
```

```
<210> SEQ ID NO 189
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189
```

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105
```

```
<210> SEQ ID NO 190
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190
```

```
Gly Gly Ser Ile Ser Ser Val Gly Tyr Tyr
1               5                   10
```

```
<210> SEQ ID NO 191
<211> LENGTH: 7
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 191

Ile Tyr Tyr Ser Gly Ser Ile
1               5

<210> SEQ ID NO 192
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Cys Ala Ser Val Gly Ile Val Gly Ala Ser Tyr Phe Glu Tyr Trp
1               5                   10                  15

<210> SEQ ID NO 193
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Gln Ser Val Ser Ser Tyr
1               5

<210> SEQ ID NO 194
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Asp Ala Ser
1

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Cys Gln Gln Arg Ser Asn Trp Pro Ile Thr Phe
1               5                   10

<210> SEQ ID NO 196
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196

-continued

```
caggtgcagc tggtggagtc tggggggaggc ttggttcggc ctggggggtc cctgagactc      60
tcctgtgcag tctctggatt caccttttagc agctatgcca tgagctgggt ccgccaggct     120
ccagggaagg ggctggagtg ggtctcaggt attagtggta gtggtggtag cacatacaac     180
gcagactccg tgaagggccg gttcaccatc tccagagaca attccaagaa cacgctgtat     240
cttcaaatga acagcctgag agccgaggac acggccgtat attactgtgc gaaaattttt     300
gggtcctact actttgacta ctggggccag ggaaccctgg tcaccgtctc gagt           354
```

<210> SEQ ID NO 197
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 197

```
gaaattgtga tgacacagtc tccagactcc ctggctgtgt ctctgggcga gagggccacc      60
atcaactgca agtccagcca gagtgtttta tacagctcca ataataagaa ctacttagct     120
tggtaccagc agaaatcagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtggt     300
ccaccgacgt tcggccaagg gaccaaggtg gaaatcaaa                            339
```

<210> SEQ ID NO 198
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198

```
Gln Val Gln Leu Val Glu Ser Gly Gly Gly Leu Val Arg Pro Gly Gly
1               5                   10                  15

Ser Leu Arg Leu Ser Cys Ala Val Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Phe Gly Ser Tyr Tyr Phe Asp Tyr Trp Gly Gln Gly Thr
            100                 105                 110

Leu Val Thr Val Ser Ser
        115
```

<210> SEQ ID NO 199
<211> LENGTH: 113
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 199

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Gly Pro Pro Thr Phe Gly Gln Gly Thr Lys Val Glu Ile
            100                 105                 110

Lys
```

<210> SEQ ID NO 200
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

```
Gly Phe Thr Phe Ser Ser Tyr Ala
1               5
```

<210> SEQ ID NO 201
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

```
Ile Ser Gly Ser Gly Gly Ser Thr
1               5
```

<210> SEQ ID NO 202
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

```
Cys Ala Lys Ile Phe Gly Ser Tyr Tyr Phe Asp Tyr Trp
1               5                   10
```

<210> SEQ ID NO 203
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Gln Ser Val Leu Tyr Ser Ser Asn Asn Lys Asn Tyr
1               5                   10

<210> SEQ ID NO 204
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Trp Ala Ser
1

<210> SEQ ID NO 205
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Cys Gln Gln Tyr Tyr Ser Gly Pro Pro Thr Phe
1               5                   10

<210> SEQ ID NO 206
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 206
caggtccagc tacagcagtc tggggggaggc ttggttcatc ctggggggtc cctaagactc      60
tcctgtgcag cctctggatt caccgttgac acctatgcca tgacctgggt ccgccaggct     120
ccagggaagg ggctggagtg ggtctcaggt attagcggta gtggtggtag cacatactac     180
gcagactccg tgaagggccg gttcaccatc tccagagaca actccaagaa cacgctgtat     240
ctgcaaatga acagcctgag agacgaggac acggccgtat attactgtgc gaagatagtg     300
ggagttaccc actttgacta ctggggccag ggcaccctgg tcacggtctc gagt          354

<210> SEQ ID NO 207
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 207
gaaattgtga tgacgcagtc tccagactcc ctggctgtgt ctctgggcga gagggccacc      60
atcaactgca agtccagcca gagtgtttta tacaggtcca acaataagaa ctatttagct     120

```
tggtaccagc agaaaccagg acagcctcct aagctgctca tttactgggc atctacccgg      180
gaatccgggg tccctgaccg attcagtggc agcgggtctg ggacagattt cactctcacc      240
atcagcagcc tgcaggctga agatgtggca gtttattact gtcagcaata ttatagtggt      300
ccgatcacct tcggccaagg gacacgactg gagattaag                            339
```

```
<210> SEQ ID NO 208
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Gln Val Gln Leu Gln Gln Ser Gly Gly Gly Leu Val His Pro Gly Gly
1               5                   10                  15

Ser Leu Arg Leu Ser Cys Ala Ala Ser Gly Phe Thr Val Asp Thr Tyr
            20                  25                  30

Ala Met Thr Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Lys Ile Val Gly Val Thr His Phe Asp Tyr Trp Gly Gln Gly Thr
            100                 105                 110

Leu Val Thr Val Ser Ser
        115
```

```
<210> SEQ ID NO 209
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Ile Thr Phe Gly Gln Gly Thr Arg Leu Glu Ile
            100                 105                 110

Lys
```

```
<210> SEQ ID NO 210
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Gly Phe Thr Val Asp Thr Tyr Ala
1               5

<210> SEQ ID NO 211
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Ile Ser Gly Ser Gly Gly Ser Thr
1               5

<210> SEQ ID NO 212
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Cys Ala Lys Ile Val Gly Val Thr His Phe Asp Tyr Trp
1               5                   10

<210> SEQ ID NO 213
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Gln Ser Val Leu Tyr Arg Ser Asn Asn Lys Asn Tyr
1               5                   10

<210> SEQ ID NO 214
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Trp Ala Ser
1

<210> SEQ ID NO 215
<211> LENGTH: 11
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Cys Gln Gln Tyr Tyr Ser Gly Pro Ile Thr Phe
1               5                   10

<210> SEQ ID NO 216
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 216
caggtcacct tgaaggagtc gggcccagga ctggtgaagc cttcacagac cctgtccctc        60
acctgcactg tctctggtgg ctccatcagc agtggtggtc attactggag ctggatccgc       120
cagcacccag ggaagggcct ggagtggatt gggtacatct cttacagtgg gagcacctac       180
tacaacccgt ccctcaagag tcgacttacc atatcagtag acacgtctaa gaaccagttc       240
tccctgaagc tgagctctgt gactgccgcg gacacggccg tgtattactg tgcgaccgcg       300
tattacgata ttttgactgg ttacccttttt gactactggg gccagggaac cctggtcacg      360
gtctcgagt                                                                369

<210> SEQ ID NO 217
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 217
gaaattgtga tgacacagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccgaca gggccactgg catcccagcc       180
aggttcagtg gcagtgggtc tgggacagac ttcactctca ccatcagcag cctagagcct       240
gaagattttg cagtttatta ctgtcagcag cgtagcaact ggccgatcac cttcggccaa       300
gggacacgac tggagatcaa g                                                  321

<210> SEQ ID NO 218
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 218

Gln Val Thr Leu Lys Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

```
Gly His Tyr Trp Ser Trp Ile Arg Gln His Pro Gly Lys Gly Leu Glu
        35                  40                  45

Trp Ile Gly Tyr Ile Ser Tyr Ser Gly Ser Thr Tyr Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Thr Ala Tyr Tyr Asp Ile Leu Thr Gly Tyr Pro Phe Asp Tyr
            100                 105                 110

Trp Gly Gln Gly Thr Leu Val Thr Val Ser Ser
        115                 120
```

```
<210> SEQ ID NO 219
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219
```

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asp Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105
```

```
<210> SEQ ID NO 220
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220
```

```
Gly Gly Ser Ile Ser Ser Gly Gly His Tyr
1               5                   10
```

```
<210> SEQ ID NO 221
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221
```

-continued

```
Ile Ser Tyr Ser Gly Ser Thr
1               5

<210> SEQ ID NO 222
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Cys Ala Thr Ala Tyr Tyr Asp Ile Leu Thr Gly Tyr Pro Phe Asp Tyr
1               5                   10                  15

Trp

<210> SEQ ID NO 223
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gln Ser Val Ser Ser Tyr
1               5

<210> SEQ ID NO 224
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Asp Ala Ser
1

<210> SEQ ID NO 225
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Cys Gln Gln Arg Ser Asn Trp Pro Ile Thr Phe
1               5                   10

<210> SEQ ID NO 226
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 226
caggtgcagc tacagcagtc gggcccagga ctggtgaagc cttcacagac cctgtccctc    60
```

```
acctgcactg tctctggtgg ctccatcagc agtggtggtt actactggag ctggatccgc    120
cagcacccag ggaagggcct ggagtggatt gggtacatct cttatagtgg gagtatctac    180
tacaacccgt ccctcaagag tcgagttacc atatcagtag acacgtctaa gaaccagttc    240
tccctgaagc tgagctctgt gactgccacg gacacggccg tgtattactg tgcgaccgcg    300
tattacgatc ttttgactgg ttaccctttt gactactggg gccagggaac cctggtcacg    360
gtctcgagt                                                             369
```

```
<210> SEQ ID NO 227
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 227
gaaattgtga tgacgcagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgatcac cttcggccaa    300
gggacacgac tggagattaa g                                              321
```

```
<210> SEQ ID NO 228
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 228

Gln Val Gln Leu Gln Gln Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Ser Tyr Ser Gly Ser Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Thr Asp Thr Ala Val Tyr Tyr
                85                  90                  95

Cys Ala Thr Ala Tyr Tyr Asp Leu Leu Thr Gly Tyr Pro Phe Asp Tyr
            100                 105                 110

Trp Gly Gln Gly Thr Leu Val Thr Val Ser Ser
        115                 120
```

```
<210> SEQ ID NO 229
<211> LENGTH: 107
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 229

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 230
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Gly Gly Ser Ile Ser Ser Gly Gly Tyr Tyr
1               5                   10

<210> SEQ ID NO 231
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Ile Ser Tyr Ser Gly Ser Ile
1               5

<210> SEQ ID NO 232
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Cys Ala Thr Ala Tyr Tyr Asp Leu Leu Thr Gly Tyr Pro Phe Asp Tyr
1               5                   10                  15

Trp

<210> SEQ ID NO 233
<211> LENGTH: 6
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 233

Gln Ser Val Ser Ser Tyr
1               5

<210> SEQ ID NO 234
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Asp Ala Ser
1

<210> SEQ ID NO 235
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Cys Gln Gln Arg Ser Asn Trp Pro Ile Thr Phe
1               5                   10

<210> SEQ ID NO 236
<211> LENGTH: 301
<212> TYPE: PRT
<213> ORGANISM: Homo sapiens

<400> SEQUENCE: 236

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
        50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
        130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175
```

```
Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
            245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
    290                 295                 300
```

<210> SEQ ID NO 237
<211> LENGTH: 302
<212> TYPE: PRT
<213> ORGANISM: Macaca fascicularis

<400> SEQUENCE: 237

```
Met Phe Ser His Leu Pro Phe Asp Cys Val Leu Leu Leu Leu Leu Leu
1               5                   10                  15

Leu Leu Thr Arg Ser Ser Glu Val Glu Tyr Ile Ala Glu Val Gly Gln
            20                  25                  30

Asn Ala Tyr Leu Pro Cys Ser Tyr Thr Pro Ala Pro Pro Gly Asn Leu
            35                  40                  45

Val Pro Val Cys Trp Gly Lys Gly Ala Cys Pro Val Phe Asp Cys Ser
    50                  55                  60

Asn Val Val Leu Arg Thr Asp Asn Arg Asp Val Asn Asp Arg Thr Ser
65                  70                  75                  80

Gly Arg Tyr Trp Leu Lys Gly Asp Phe His Lys Gly Asp Val Ser Leu
            85                  90                  95

Thr Ile Glu Asn Val Thr Leu Ala Asp Ser Gly Val Tyr Cys Cys Arg
            100                 105                 110

Ile Gln Ile Pro Gly Ile Met Asn Asp Glu Lys His Asn Val Lys Leu
            115                 120                 125

Val Val Ile Lys Pro Ala Lys Val Thr Pro Ala Pro Thr Leu Gln Arg
            130                 135                 140

Asp Leu Thr Ser Ala Phe Pro Arg Met Leu Thr Thr Gly Glu His Gly
145                 150                 155                 160

Pro Ala Glu Thr Gln Thr Pro Gly Ser Leu Pro Asp Val Asn Leu Thr
            165                 170                 175

Val Ser Asn Phe Phe Cys Glu Leu Gln Ile Phe Thr Leu Thr Asn Glu
            180                 185                 190

Leu Arg Asp Ser Gly Ala Thr Ile Arg Thr Ala Ile Tyr Ile Ala Ala
            195                 200                 205

Gly Ile Ser Ala Gly Leu Ala Leu Ala Leu Ile Phe Gly Ala Leu Ile
    210                 215                 220

Phe Lys Trp Tyr Ser His Ser Lys Glu Lys Thr Gln Asn Leu Ser Leu
225                 230                 235                 240

Ile Ser Leu Ala Asn Ile Pro Pro Ser Gly Leu Ala Asn Ala Val Ala
```

-continued

```
                    245                 250                 255

Glu Gly Ile Arg Ser Glu Glu Asn Ile Tyr Thr Ile Glu Glu Asp Val
                260                 265                 270

Tyr Glu Val Glu Glu Pro Asn Glu Tyr Tyr Cys Tyr Val Ser Ser Gly
            275                 280                 285

Gln Gln Pro Ser Gln Pro Leu Gly Cys Arg Val Ala Met Pro
        290                 295                 300

<210> SEQ ID NO 238
<211> LENGTH: 281
<212> TYPE: PRT
<213> ORGANISM: Mus musculus

<400> SEQUENCE: 238

Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
                20                  25                  30

Asn Ala Tyr Leu Pro Cys Ser Tyr Thr Leu Ser Thr Pro Gly Ala Leu
            35                  40                  45

Val Pro Met Cys Trp Gly Lys Gly Phe Cys Pro Trp Ser Gln Cys Thr
        50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
                100                 105                 110

Ile Gln Phe Pro Gly Leu Met Asn Asp Lys Lys Leu Glu Leu Lys Leu
            115                 120                 125

Asp Ile Lys Ala Ala Lys Val Thr Pro Ala Gln Thr Ala His Gly Asp
        130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Leu Lys Trp Tyr Ser Cys Lys Lys Lys Lys
        210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
                260                 265                 270

Cys Tyr Val Asn Ser Gln Gln Pro Ser
            275                 280

<210> SEQ ID NO 239
<211> LENGTH: 282
<212> TYPE: PRT
<213> ORGANISM: Rattus norvegicus
```

<400> SEQUENCE: 239

```
Met Phe Ser Trp Leu Pro Phe Ser Cys Ala Leu Leu Leu Leu Gln Pro
1               5                   10                  15

Leu Pro Ala Arg Ser Leu Glu Asn Ala Tyr Thr Ala Glu Val Gly Lys
            20                  25                  30

Asn Ala Tyr Leu Pro Cys Ser Tyr Thr Val Pro Ala Pro Gly Thr Leu
        35                  40                  45

Val Pro Ile Cys Trp Gly Lys Gly Ser Cys Pro Leu Leu Gln Cys Ala
    50                  55                  60

Ser Val Val Leu Arg Thr Asp Glu Thr Asn Val Thr Tyr Arg Lys Ser
65                  70                  75                  80

Arg Arg Tyr Gln Leu Lys Gly Asn Phe Tyr Lys Gly Asp Met Ser Leu
                85                  90                  95

Thr Ile Lys Asn Val Thr Leu Ala Asp Ser Gly Thr Tyr Cys Cys Arg
            100                 105                 110

Ile Gln Phe Pro Gly Pro Met Asn Asp Glu Lys Leu Glu Leu Lys Leu
        115                 120                 125

Ser Ile Thr Glu Pro Ala Lys Val Ile Pro Ala Gly Thr Ala His Gly
    130                 135                 140

Asp Ser Thr Thr Ala Ser Pro Arg Thr Leu Thr Thr Glu Gly Ser Gly
145                 150                 155                 160

Ser Glu Thr Gln Thr Leu Val Thr Leu His Asp Asn Asn Gly Thr Lys
                165                 170                 175

Ile Ser Thr Trp Ala Asp Glu Ile Lys Asp Ser Gly Glu Thr Ile Arg
            180                 185                 190

Thr Ala Val His Ile Gly Val Gly Val Ser Ala Gly Leu Ala Leu Ala
            195                 200                 205

Leu Ile Leu Gly Val Leu Ile Leu Lys Trp Tyr Ser Ser Lys Lys Lys
    210                 215                 220

Lys Leu Gln Asp Leu Ser Leu Ile Thr Leu Ala Asn Ser Pro Pro Gly
225                 230                 235                 240

Gly Leu Val Asn Ala Gly Ala Gly Arg Ile Arg Ser Glu Glu Asn Ile
            245                 250                 255

Tyr Thr Ile Glu Glu Asn Ile Tyr Glu Met Glu Asn Ser Asn Glu Tyr
            260                 265                 270

Tyr Cys Tyr Val Ser Ser Gln Gln Pro Ser
            275                 280
```

<210> SEQ ID NO 240
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

```
Gly Gly Gly Gly Ser Gly Gly Gly Gly Ser Gly Gly Gly Gly Ser
1               5                   10                  15
```

ANTI-TIM-3 ANTIBODIES AND COMPOSITIONS

CROSS-REFERENCE TO RELATED APPLICATION

This application is a divisional application of U.S. patent application Ser. No. 16/093,024, filed on Oct. 11, 2018, which is a national stage application under 35 U.S.C. § 371 of International Patent Application No. PCT/EP2017/058696, filed on Apr. 11, 2017, which claims priority from U.S. Patent Application 62/321,476, filed Apr. 12, 2016. The disclosures of those applications are incorporated by reference herein in their entirety.

SEQUENCE LISTING

The instant application contains a Sequence Listing that has been submitted electronically in ASCII format and is hereby incorporated by reference in its entirety. Said ASCII copy, created on Mar. 28, 2017, is named 022675WO053.txt and is 150,698 bytes in size.

BACKGROUND OF THE INVENTION

TIM-3 (T-cell immunoglobulin and mucin-domain containing 3), also known as HAVCR2 (hepatitis A virus cellular receptor 2) or CD366, is a member of the T-cell immunoglobulin and mucin domain protein family. TIM-3 is encoded in humans by the Havcr2 gene and is a 33 kDa type I glycoprotein with a membrane distal IgV domain and a membrane proximal mucin-domain. It contains a conserved region of five Tyr residues in the intracellular domain, which are phosphorylated upon ligand binding. TIM-3 is expressed by a range of different cells originating from both the adaptive and innate arms of the immune system including T-cells, dendritic cells, macrophages, and natural killer (NK) cells. TIM-3 expression is low on naïve T cells but becomes highly upregulated upon T cell activation. In contrast to T-cells, innate cells such as dendritic cells, NK cells and monocytes have high basal TIM-3 expression. TIM-3 has been associated with several, mostly promiscuous, ligands, including galectin-9, phosphatidylserine, CEACAM-1 and HMGB-1, but the exact roles of these ligands are currently unknown.

Although TIM-3 has been suggested to be a checkpoint inhibitor, there is relatively sparse evidence to support the idea that TIM-3 directly mediates suppression of T cell activation or cytokine secretion in a manner similar to, e.g., PD-1. Furthermore, and in contrast to PD-1, TIM-3 appears to play a role in regulation of cells of the innate system, and in particular dendritic cells. The majority of functional data related to TIM-3 and its role in tumor immunology comes from in vivo studies using various antibodies. In most of these studies, due to poor antibody validation, it is not clear whether the effects of the TIM-3 antibodies are mediated by inhibition of ligand binding or by an agonistic effect on the target.

In view of its immune response regulatory properties, TIM-3 has been investigated as a potential target for immunotherapy, including for treatment of cancer and autoimmune diseases. A single anti-TIM-3 antibody is currently in clinical development, but there are currently no approved anti-TIM-3 antibodies.

In view of the critical role of TIM-3 as an immune modulator, there is a need for new and improved immune therapies that target TIM-3 to treat cancers and certain disorders of the immune system.

SUMMARY OF THE INVENTION

The present invention is directed to novel recombinant antibodies targeting TIM-3, as well as pharmaceutical compositions comprising one or more of these antibodies, e.g., an anti-TIM-3 antibody that via activity on TIM-3 activates various immune cells such as professional antigen-presenting cells (e.g., dendritic cells and macrophages) and T cells (e.g., helper T cells and cytotoxic T cells). The present invention is also directed to use of the antibodies and pharmaceutical compositions for enhancing immunity in a patient, and for treatment of cancers originating from tissues such as skin, lung, intestine, ovary, brain, prostate, kidney, soft tissues, the hematopoietic system, head and neck, liver, bladder, breast, stomach, uterus and pancreas. Compared to currently available treatments for such cancers, including antibody treatments, it is contemplated that the antibodies of the invention may provide a superior clinical response either alone or in combination with another cancer therapeutic, such as an antibody targeting another immune checkpoint protein.

In some embodiments, the present invention provides an anti-TIM-3 antibody or an antigen-binding portion thereof, wherein the anti-TIM-3 antibody is the antibody referred to herein as antibody 15086.15086, 15086.16837, 15086.17145, 15086.17144, 20131, 20293, 15105, 15107, 15109, 15174, 15175, 15260, 15284, 15299, 15353, 15354, 17244, 17245, 19324, 19416, 19568, 20185, 20300, 20362, or 20621 or a variant of any of these, where the variant may, e.g., contain certain minimum amino acid changes relative to said antibody (e.g., 1, 2, 3, 4, 5, 6, 7, 8, 9, or 10 amino acid changes, which may be, e.g., in the framework regions) without losing the antigen-binding specificity of antibody.

In some embodiments, the anti-TIM-3 antibody competes for binding to human TIM-3 with, or binds to the same epitope of human TIM-3 as, any one of antibodies 15086.15086, 15086.16837, 15086.17145, 15086.17144, 20131, 20293, 15105, 15107, 15109, 15174, 15175, 15260, 15284, 15299, 15353, 15354, 17244, 17245, 19324, 19416, 19568, 20185, 20300, 20362, and 20621.

In some embodiments, the anti-TIM-3 antibody comprises an H-CDR3 comprising the H-CDR3 amino acid sequence of SEQ ID NO: 9, 32, 42, 52, 62, 72, 82, 92, 102, 112, 122, 132, 142, 152, 162, 172, 182, 192, 202, 212, 222, or 232.

In some embodiments, the anti-TIM-3 antibody comprises H-CDR1-3 comprising the H-CDR1-3 sequences, respectively, of SEQ ID NOs: 7-9, 30-32, 40-42, 50-52, 60-62, 70-72, 80-82, 90-92, 100-102, 110-112, 120-122, 130-132, 140-142, 150-152, 160-162, 170-172, 180-182, 190-192, 200-202, 210-212, 220-222, or 230-232.

In some embodiments, the anti-TIM-3 antibody has a heavy chain variable domain (VH) that is at least 90% (e.g., at least 92%, at least 95%, at least 98%, or at least 99%) identical in amino acid sequence to SEQ ID NO: 3, 15, 28, 38, 48, 58, 68, 78, 88, 98, 108, 118, 128, 138, 148, 158, 168, 178, 188, 198, 208, 218, or 228.

In some embodiments, the anti-TIM-3 antibody has a VH that comprises SEQ ID NO: 3, 15, 28, 38, 48, 58, 68, 78, 88, 98, 108, 118, 128, 138, 148, 158, 168, 178, 188, 198, 208, 218, or 228.

In some embodiments, the anti-TIM-3 antibody has a heavy chain (HC) that comprises the VH amino acid sequence of SEQ ID NO: 3, 15, 28, 38, 48, 58, 68, 78, 88, 98, 108, 118, 128, 138, 148, 158, 168, 178, 188, 198, 208, 218, or 228 and the heavy chain constant region (CH) amino acid sequence of SEQ ID NO: 5 or SEQ ID NO: 23, 24 or 25.

In some embodiments, the anti-TIM-3 antibody comprises an L-CDR3 comprising the L-CDR3 amino acid sequence of SEQ ID NO: 12, 35, 45, 55, 65, 75, 85, 95, 105, 115, 125, 135, 145, 155, 165, 175, 185, 195, 205, 215, 225, or 235.

In some embodiments, the anti-TIM-3 antibody comprises L-CDR1-3 comprising the L-CDR1-3 sequences, respectively, of SEQ ID NOs: 10-12, 33-35, 43-45, 53-55, 63-65, 73-75, 83-85, 93-95, 103-105, 113-115, 123-125, 133-135, 143-145, 153-155, 163-165, 173-175, 183-185, 193-195, 203-205, 213-215, 223-225, or 233-235.

In some embodiments, the anti-TIM-3 antibody has a light chain variable domain (VL) that is at least 90% (e.g., at least 92%, at least 95%, at least 98%, or at least 99%) identical in sequence to the VL amino acid sequence of SEQ ID NO: 4, 29, 39, 49, 59, 69, 79, 89, 99, 109, 119, 129, 139, 149, 159, 169, 179, 189, 199, 209, 219, or 229.

In some embodiments, the anti-TIM-3 antibody has a VL that comprises the VL amino acid sequence of SEQ ID NO: 4, 29, 39, 49, 59, 69, 79, 89, 99, 109, 119, 129, 139, 149, 159, 169, 179, 189, 199, 209, 219, or 229.

In some embodiments, the anti-TIM-3 antibody has a light chain (LC) that comprises the VL amino acid sequence of SEQ ID NO: 4, 29, 39, 49, 59, 69, 79, 89, 99, 109, 119, 129, 139, 149, 159, 169, 179, 189, 199, 209, 219, or 229 and the light chain constant region amino acid sequence of SEQ ID NO: 6.

In some embodiments, the anti-TIM-3 antibody comprises any of the above heavy chain sequences and any of the above light chain sequences.

In some embodiments, the anti-TIM-3 antibody comprises an H-CDR3 and L-CDR3 comprising the H-CDR3 and L-CDR3 amino acid sequences, respectively, of SEQ ID NOs: 9 and 12, 32 and 35, 42 and 45, 52 and 55, 62 and 65, 72 and 75, 82 and 85, 92 and 95, 102 and 105, 112 and 115, 122 and 125, 132 and 135, 142 and 145, 152 and 155, 162 and 165, 172 and 175, 182 and 185, 192 and 195, 202 and 205, 212 and 215, 222 and 225, and 232 and 235.

In some embodiments, the anti-TIM-3 antibody comprises H-CDR1-3 and L-CDR1-3 comprising the H-CDR1-3 and L-CDR1-3 sequences, respectively, of SEQ ID NOs: 7-12, 30-35, 40-45, 50-55, 60-65, 70-75, 80-85, 90-95, 100-105, 110-115, 120-125, 130-135, 140-145, 150-155, 160-165, 170-175, 180-185, 190-195, 200-205, 210-215, 220-225, or 230-235.

In some embodiments, the anti-TIM-3 antibody has a VH that is at least 90% (e.g., at least 92%, at least 95%, at least 98%, or at least 99%) identical in sequence to the amino acid sequence of SEQ ID NO: 3, 15, 28, 38, 48, 58, 68, 78, 88, 98, 108, 118, 128, 138, 148, 158, 168, 178, 188, 198, 208, 218, or 228, and a VL that is at least 90% (e.g., at least 92%, at least 95%, at least 98%, or at least 99%) identical in sequence to the amino acid sequence of SEQ ID NO: 4, 29, 39, 49, 59, 69, 79, 89, 99, 109, 119, 129, 139, 149, 159, 169, 179, 189, 199, 209, 219, or 229.

In some embodiments, the anti-TIM-3 antibody has a VH that comprises the amino acid sequence of SEQ ID NO: 3, 15, 28, 38, 48, 58, 68, 78, 88, 98, 108, 118, 128, 138, 148, 158, 168, 178, 188, 198, 208, 218, or 228, and a VL that comprises the amino acid sequence of SEQ ID NO: 4, 29, 39, 49, 59, 69, 79, 89, 99, 109, 119, 129, 139, 149, 159, 169, 179, 189, 199, 209, 219, or 229.

In some embodiments, the anti-TIM-3 antibody has an LC that comprises the amino acid sequence of SEQ ID NO: 4, 29, 39, 49, 59, 69, 79, 89, 99, 109, 119, 129, 139, 149, 159, 169, 179, 189, 199, 209, 219, or 229 and the amino acid sequence of SEQ ID NO: 6; and an HC that comprises (i) the amino acid sequence of SEQ ID NO: 3, 28, 38, 48, 58, 68, 78, 88, 98, 108, 118, 128, 138, 148, 158, 168, 178, 188, 198, 208, 218, or 228 and the amino acid sequence of SEQ ID NO: 5, or (ii) the amino acid sequence of SEQ ID NO: 15, 28, 38, 48, 58, 68, 78, 88, 98, 108, 118, 128, 138, 148, 158, 168, 178, 188, 198, 208, 218, or 228 and the amino acid sequence of SEQ ID NO: 23, 24 or 25.

In some embodiments, the anti-TIM-3 antibody or antigen-binding portion of the invention comprises the H-CDR1-3 and L-CDR1-3 amino acid sequences of:
a) SEQ ID NOs: 7-12, respectively;
b) SEQ ID NOs: 30-35, respectively;
c) SEQ ID NOs: 40-45, respectively;
d) SEQ ID NOs: 50-55, respectively;
e) SEQ ID NOs: 60-65, respectively;
f) SEQ ID NOs: 70-75, respectively;
g) SEQ ID NOs: 80-85, respectively;
h) SEQ ID NOs: 90-95, respectively;
i) SEQ ID NOs: 100-105, respectively;
j) SEQ ID NOs: 110-115, respectively;
k) SEQ ID NOs: 120-125, respectively;
l) SEQ ID NOs: 130-135, respectively;
m) SEQ ID NOs: 140-145, respectively;
n) SEQ ID NOs: 150-155, respectively;
o) SEQ ID NOs: 160-165, respectively;
p) SEQ ID NOs: 170-175, respectively;
q) SEQ ID NOs: 180-185, respectively;
r) SEQ ID NOs: 190-195, respectively;
s) SEQ ID NOs: 200-205, respectively;
t) SEQ ID NOs: 210-215, respectively;
u) SEQ ID NOs: 220-225, respectively; or
v) SEQ ID NOs: 230-235, respectively.

In some embodiments, the anti-TIM-3 antibody or antigen-binding portion of the invention competes for binding to human TIM-3 with, or binds to the same epitope of human TIM-3 as, an antibody whose heavy and light chain variable domains comprise the amino acid sequences of:
a) SEQ ID NOs: 3 and 4, respectively;
b) SEQ ID NOs: 15 and 4, respectively;
c) SEQ ID NOs: 28 and 29, respectively;
d) SEQ ID NOs: 38 and 39, respectively;
e) SEQ ID NOs: 48 and 49, respectively;
f) SEQ ID NOs: 58 and 59, respectively;
g) SEQ ID NOs: 68 and 69, respectively;
h) SEQ ID NOs: 78 and 79, respectively;
i) SEQ ID NOs: 88 and 89, respectively;
j) SEQ ID NOs: 98 and 99, respectively;
k) SEQ ID NOs: 108 and 109, respectively;
l) SEQ ID NOs: 118 and 119, respectively;
m) SEQ ID NOs: 128 and 129, respectively;
n) SEQ ID NOs: 138 and 139, respectively;
o) SEQ ID NOs: 148 and 149, respectively;
p) SEQ ID NOs: 158 and 159, respectively;
q) SEQ ID NOs: 168 and 169, respectively;
r) SEQ ID NOs: 178 and 179, respectively;
s) SEQ ID NOs: 188 and 189, respectively;
t) SEQ ID NOs: 198 and 199, respectively;
u) SEQ ID NOs: 208 and 209, respectively;
v) SEQ ID NOs: 218 and 219, respectively; or
w) SEQ ID NOs: 228 and 229, respectively.

In some embodiments, the anti-TIM-3 antibody or antigen-binding portion of the invention comprises a heavy chain variable domain and a light chain variable domain with amino acid sequences at least 90% identical to the amino acid sequences of:

a) SEQ ID NOs: 3 and 4, respectively;
b) SEQ ID NOs: 15 and 4, respectively;
c) SEQ ID NOs: 28 and 29, respectively;
d) SEQ ID NOs: 38 and 39, respectively;
e) SEQ ID NOs: 48 and 49, respectively;
f) SEQ ID NOs: 58 and 59, respectively;
g) SEQ ID NOs: 68 and 69, respectively;
h) SEQ ID NOs: 78 and 79, respectively;
i) SEQ ID NOs: 88 and 89, respectively;
j) SEQ ID NOs: 98 and 99, respectively;
k) SEQ ID NOs: 108 and 109, respectively;
l) SEQ ID NOs: 118 and 119, respectively;
m) SEQ ID NOs: 128 and 129, respectively;
n) SEQ ID NOs: 138 and 139, respectively;
o) SEQ ID NOs: 148 and 149, respectively;
p) SEQ ID NOs: 158 and 159, respectively;
q) SEQ ID NOs: 168 and 169, respectively;
r) SEQ ID NOs: 178 and 179, respectively;
s) SEQ ID NOs: 188 and 189, respectively;
t) SEQ ID NOs: 198 and 199, respectively;
u) SEQ ID NOs: 208 and 209, respectively;
v) SEQ ID NOs: 218 and 219, respectively; or
w) SEQ ID NOs: 228 and 229, respectively.

In some embodiments, the anti-TIM-3 antibody or antigen-binding portion of the invention comprises a heavy chain and a light chain whose variable domains have the amino acid sequences of:

a) SEQ ID NOs: 3 and 4, respectively;
b) SEQ ID NOs: 15 and 4, respectively;
c) SEQ ID NOs: 28 and 29, respectively;
d) SEQ ID NOs: 38 and 39, respectively;
e) SEQ ID NOs: 48 and 49, respectively;
f) SEQ ID NOs: 58 and 59, respectively;
g) SEQ ID NOs: 68 and 69, respectively;
h) SEQ ID NOs: 78 and 79, respectively;
i) SEQ ID NOs: 88 and 89, respectively;
j) SEQ ID NOs: 98 and 99, respectively;
k) SEQ ID NOs: 108 and 109, respectively;
l) SEQ ID NOs: 118 and 119, respectively;
m) SEQ ID NOs: 128 and 129, respectively;
n) SEQ ID NOs: 138 and 139, respectively;
o) SEQ ID NOs: 148 and 149, respectively;
p) SEQ ID NOs: 158 and 159, respectively;
q) SEQ ID NOs: 168 and 169, respectively;
r) SEQ ID NOs: 178 and 179, respectively;
s) SEQ ID NOs: 188 and 189, respectively;
t) SEQ ID NOs: 198 and 199, respectively;
u) SEQ ID NOs: 208 and 209, respectively;
v) SEQ ID NOs: 218 and 219, respectively; or
w) SEQ ID NOs: 228 and 229, respectively.

In some embodiments, the anti-TIM-3 antibody of the invention comprises:

a) a heavy chain (HC) comprising the amino acid sequences of SEQ ID NOs: 3 and 5 and a light chain (LC) comprising the amino acid sequences of SEQ ID NOs: 4 and 6;
b) an HC comprising the amino acid sequences of SEQ ID NOs: 28 and 5 and an LC comprising the amino acid sequences of SEQ ID NOs: 29 and 6;
c) an HC comprising the amino acid sequences of SEQ ID NOs: 38 and 5 and an LC comprising the amino acid sequences of SEQ ID NOs: 39 and 6;

d) an HC comprising the amino acid sequences of SEQ ID NOs: 48 and 5 and an LC comprising the amino acid sequences of SEQ ID NOs: 49 and 6;
e) an HC comprising the amino acid sequences of SEQ ID NOs: 58 and 5 and an LC comprising the amino acid sequences of SEQ ID NOs: 59 and 6;
f) an HC comprising the amino acid sequences of SEQ ID NOs: 68 and 5 and an LC comprising the amino acid sequences of SEQ ID NOs: 69 and 6;
g) an HC comprising the amino acid sequences of SEQ ID NOs: 78 and 5 and an LC comprising the amino acid sequences of SEQ ID NOs: 79 and 6;
h) an HC comprising the amino acid sequences of SEQ ID NOs: 88 and 5 and an LC comprising the amino acid sequences of SEQ ID NOs: 89 and 6;
i) an HC comprising the amino acid sequences of SEQ ID NOs: 98 and 5 and an LC comprising the amino acid sequences of SEQ ID NOs: 99 and 6;
j) an HC comprising the amino acid sequences of SEQ ID NOs: 108 and 5 and an LC comprising the amino acid sequences of SEQ ID NOs: 109 and 6;
k) an HC comprising the amino acid sequences of SEQ ID NOs: 118 and 5 and an LC comprising the amino acid sequences of SEQ ID NOs: 119 and 6;
l) an HC comprising the amino acid sequences of SEQ ID NOs: 128 and 5 and an LC comprising the amino acid sequences of SEQ ID NOs: 129 and 6;
m) an HC comprising the amino acid sequences of SEQ ID NOs: 138 and 5 and an LC comprising the amino acid sequences of SEQ ID NOs: 139 and 6;
n) an HC comprising the amino acid sequences of SEQ ID NOs: 148 and 5 and an LC comprising the amino acid sequences of SEQ ID NOs: 149 and 6;
o) an HC comprising the amino acid sequences of SEQ ID NOs: 158 and 5 and an LC comprising the amino acid sequences of SEQ ID NOs: 159 and 6;
p) an HC comprising the amino acid sequences of SEQ ID NOs: 168 and 5 and an LC comprising the amino acid sequences of SEQ ID NOs: 169 and 6;
q) an HC comprising the amino acid sequences of SEQ ID NOs: 178 and 5 and an LC comprising the amino acid sequences of SEQ ID NOs: 179 and 6;
r) an HC comprising the amino acid sequences of SEQ ID NOs: 188 and 5 and an LC comprising the amino acid sequences of SEQ ID NOs: 189 and 6;
s) an HC comprising the amino acid sequences of SEQ ID NOs: 198 and 5 and an LC comprising the amino acid sequences of SEQ ID NOs: 199 and 6;
t) an HC comprising the amino acid sequences of SEQ ID NOs: 208 and 5 and an LC comprising the amino acid sequences of SEQ ID NOs: 209 and 6;
u) an HC comprising the amino acid sequences of SEQ ID NOs: 218 and 5 and an LC comprising the amino acid sequences of SEQ ID NOs: 219 and 6; or
v) an HC comprising the amino acid sequences of SEQ ID NOs: 228 and 5 and an LC comprising the amino acid sequences of SEQ ID NOs: 229 and 6.

In some embodiments, the anti-TIM-3 antibody of the invention comprises:

a) an HC comprising the amino acid sequences of SEQ ID NOs: 15 and 23 and an LC comprising the amino acid sequences of SEQ ID NOs: 4 and 6;
b) an HC comprising the amino acid sequences of SEQ ID NOs: 28 and 23 and an LC comprising the amino acid sequences of SEQ ID NOs: 29 and 6;

c) an HC comprising the amino acid sequences of SEQ ID NOs: 38 and 23 and an LC comprising the amino acid sequences of SEQ ID NOs: 39 and 6;

d) an HC comprising the amino acid sequences of SEQ ID NOs: 48 and 23 and an LC comprising the amino acid sequences of SEQ ID NOs: 49 and 6;

e) an HC comprising the amino acid sequences of SEQ ID NOs: 58 and 23 and an LC comprising the amino acid sequences of SEQ ID NOs: 59 and 6;

f) an HC comprising the amino acid sequences of SEQ ID NOs: 68 and 23 and an LC comprising the amino acid sequences of SEQ ID NOs: 69 and 6;

g) an HC comprising the amino acid sequences of SEQ ID NOs: 78 and 23 and an LC comprising the amino acid sequences of SEQ ID NOs: 79 and 6;

h) an HC comprising the amino acid sequences of SEQ ID NOs: 88 and 23 and an LC comprising the amino acid sequences of SEQ ID NOs: 89 and 6;

i) an HC comprising the amino acid sequences of SEQ ID NOs: 98 and 23 and an LC comprising the amino acid sequences of SEQ ID NOs: 99 and 6;

j) an HC comprising the amino acid sequences of SEQ ID NOs: 108 and 23 and an LC comprising the amino acid sequences of SEQ ID NOs: 109 and 6;

k) an HC comprising the amino acid sequences of SEQ ID NOs: 118 and 23 and an LC comprising the amino acid sequences of SEQ ID NOs: 119 and 6;

l) an HC comprising the amino acid sequences of SEQ ID NOs: 128 and 23 and an LC comprising the amino acid sequences of SEQ ID NOs: 129 and 6;

m) an HC comprising the amino acid sequences of SEQ ID NOs: 138 and 23 and an LC comprising the amino acid sequences of SEQ ID NOs: 139 and 6;

n) an HC comprising the amino acid sequences of SEQ ID NOs: 148 and 23 and an LC comprising the amino acid sequences of SEQ ID NOs: 149 and 6;

o) an HC comprising the amino acid sequences of SEQ ID NOs: 158 and 23 and an LC comprising the amino acid sequences of SEQ ID NOs: 159 and 6;

p) an HC comprising the amino acid sequences of SEQ ID NOs: 168 and 23 and an LC comprising the amino acid sequences of SEQ ID NOs: 169 and 6;

q) an HC comprising the amino acid sequences of SEQ ID NOs: 178 and 23 and an LC comprising the amino acid sequences of SEQ ID NOs: 179 and 6;

r) an HC comprising the amino acid sequences of SEQ ID NOs: 188 and 23 and an LC comprising the amino acid sequences of SEQ ID NOs: 189 and 6;

s) an HC comprising the amino acid sequences of SEQ ID NOs: 198 and 23 and an LC comprising the amino acid sequences of SEQ ID NOs: 199 and 6;

t) an HC comprising the amino acid sequences of SEQ ID NOs: 208 and 23 and an LC comprising the amino acid sequences of SEQ ID NOs: 209 and 6;

u) an HC comprising the amino acid sequences of SEQ ID NOs: 218 and 23 and an LC comprising the amino acid sequences of SEQ ID NOs: 219 and 6; or v) an HC comprising the amino acid sequences of SEQ ID NOs: 228 and 23 and an LC comprising the amino acid sequences of SEQ ID NOs: 229 and 6.

In some embodiments, the anti-TIM-3 antibody of the invention comprises:

a) an HC comprising the amino acid sequences of SEQ ID NOs: 15 and 24 and an LC comprising the amino acid sequences of SEQ ID NOs: 4 and 6;

b) an HC comprising the amino acid sequences of SEQ ID NOs: 28 and 24 and an LC comprising the amino acid sequences of SEQ ID NOs: 29 and 6;

c) an HC comprising the amino acid sequences of SEQ ID NOs: 38 and 24 and an LC comprising the amino acid sequences of SEQ ID NOs: 39 and 6;

d) an HC comprising the amino acid sequences of SEQ ID NOs: 48 and 24 and an LC comprising the amino acid sequences of SEQ ID NOs: 49 and 6;

e) an HC comprising the amino acid sequences of SEQ ID NOs: 58 and 24 and an LC comprising the amino acid sequences of SEQ ID NOs: 59 and 6;

f) an HC comprising the amino acid sequences of SEQ ID NOs: 68 and 24 and an LC comprising the amino acid sequences of SEQ ID NOs: 69 and 6;

g) an HC comprising the amino acid sequences of SEQ ID NOs: 78 and 24 and an LC comprising the amino acid sequences of SEQ ID NOs: 79 and 6;

h) an HC comprising the amino acid sequences of SEQ ID NOs: 88 and 24 and an LC comprising the amino acid sequences of SEQ ID NOs: 89 and 6;

i) an HC comprising the amino acid sequences of SEQ ID NOs: 98 and 24 and an LC comprising the amino acid sequences of SEQ ID NOs: 99 and 6;

j) an HC comprising the amino acid sequences of SEQ ID NOs: 108 and 24 and an LC comprising the amino acid sequences of SEQ ID NOs: 109 and 6;

k) an HC comprising the amino acid sequences of SEQ ID NOs: 118 and 24 and an LC comprising the amino acid sequences of SEQ ID NOs: 119 and 6;

l) an HC comprising the amino acid sequences of SEQ ID NOs: 128 and 24 and an LC comprising the amino acid sequences of SEQ ID NOs: 129 and 6;

m) an HC comprising the amino acid sequences of SEQ ID NOs: 138 and 24 and an LC comprising the amino acid sequences of SEQ ID NOs: 139 and 6;

n) an HC comprising the amino acid sequences of SEQ ID NOs: 148 and 24 and an LC comprising the amino acid sequences of SEQ ID NOs: 149 and 6;

o) an HC comprising the amino acid sequences of SEQ ID NOs: 158 and 24 and an LC comprising the amino acid sequences of SEQ ID NOs: 159 and 6;

p) an HC comprising the amino acid sequences of SEQ ID NOs: 168 and 24 and an LC comprising the amino acid sequences of SEQ ID NOs: 169 and 6;

q) an HC comprising the amino acid sequences of SEQ ID NOs: 178 and 24 and an LC comprising the amino acid sequences of SEQ ID NOs: 179 and 6;

r) an HC comprising the amino acid sequences of SEQ ID NOs: 188 and 24 and an LC comprising the amino acid sequences of SEQ ID NOs: 189 and 6;

s) an HC comprising the amino acid sequences of SEQ ID NOs: 198 and 24 and an LC comprising the amino acid sequences of SEQ ID NOs: 199 and 6;

t) an HC comprising the amino acid sequences of SEQ ID NOs: 208 and 24 and an LC comprising the amino acid sequences of SEQ ID NOs: 209 and 6;

u) an HC comprising the amino acid sequences of SEQ ID NOs: 218 and 24 and an LC comprising the amino acid sequences of SEQ ID NOs: 219 and 6; or v) an HC comprising the amino acid sequences of SEQ ID NOs: 228 and 24 and an LC comprising the amino acid sequences of SEQ ID NOs: 229 and 6.

In some embodiments, the anti-TIM-3 antibody of the invention comprises:

a) an HC comprising the amino acid sequences of SEQ ID NOs: 15 and 25 and an LC comprising the amino acid sequences of SEQ ID NOs: 4 and 6;

b) an HC comprising the amino acid sequences of SEQ ID NOs: 28 and 25 and an LC comprising the amino acid sequences of SEQ ID NOs: 29 and 6;

c) an HC comprising the amino acid sequences of SEQ ID NOs: 38 and 25 and an LC comprising the amino acid sequences of SEQ ID NOs: 39 and 6;

d) an HC comprising the amino acid sequences of SEQ ID NOs: 48 and 25 and an LC comprising the amino acid sequences of SEQ ID NOs: 49 and 6;

e) an HC comprising the amino acid sequences of SEQ ID NOs: 58 and 25 and an LC comprising the amino acid sequences of SEQ ID NOs: 59 and 6;

f) an HC comprising the amino acid sequences of SEQ ID NOs: 68 and 25 and an LC comprising the amino acid sequences of SEQ ID NOs: 69 and 6;

g) an HC comprising the amino acid sequences of SEQ ID NOs: 78 and 25 and an LC comprising the amino acid sequences of SEQ ID NOs: 79 and 6;

h) an HC comprising the amino acid sequences of SEQ ID NOs: 88 and 25 and an LC comprising the amino acid sequences of SEQ ID NOs: 89 and 6;

i) an HC comprising the amino acid sequences of SEQ ID NOs: 98 and 25 and an LC comprising the amino acid sequences of SEQ ID NOs: 99 and 6;

j) an HC comprising the amino acid sequences of SEQ ID NOs: 108 and 25 and an LC comprising the amino acid sequences of SEQ ID NOs: 109 and 6;

k) an HC comprising the amino acid sequences of SEQ ID NOs: 118 and 25 and an LC comprising the amino acid sequences of SEQ ID NOs: 119 and 6;

l) an HC comprising the amino acid sequences of SEQ ID NOs: 128 and 25 and an LC comprising the amino acid sequences of SEQ ID NOs: 129 and 6;

m) an HC comprising the amino acid sequences of SEQ ID NOs: 138 and 25 and an LC comprising the amino acid sequences of SEQ ID NOs: 139 and 6;

n) an HC comprising the amino acid sequences of SEQ ID NOs: 148 and 25 and an LC comprising the amino acid sequences of SEQ ID NOs: 149 and 6;

o) an HC comprising the amino acid sequences of SEQ ID NOs: 158 and 25 and an LC comprising the amino acid sequences of SEQ ID NOs: 159 and 6;

p) an HC comprising the amino acid sequences of SEQ ID NOs: 168 and 25 and an LC comprising the amino acid sequences of SEQ ID NOs: 169 and 6;

q) an HC comprising the amino acid sequences of SEQ ID NOs: 178 and 25 and an LC comprising the amino acid sequences of SEQ ID NOs: 179 and 6;

r) an HC comprising the amino acid sequences of SEQ ID NOs: 188 and 25 and an LC comprising the amino acid sequences of SEQ ID NOs: 189 and 6;

s) an HC comprising the amino acid sequences of SEQ ID NOs: 198 and 25 and an LC comprising the amino acid sequences of SEQ ID NOs: 199 and 6;

t) an HC comprising the amino acid sequences of SEQ ID NOs: 208 and 25 and an LC comprising the amino acid sequences of SEQ ID NOs: 209 and 6;

u) an HC comprising the amino acid sequences of SEQ ID NOs: 218 and 25 and an LC comprising the amino acid sequences of SEQ ID NOs: 219 and 6; or v) an HC comprising the amino acid sequences of SEQ ID NOs: 228 and 25 and an LC comprising the amino acid sequences of SEQ ID NOs: 229 and 6.

In certain embodiments, the invention provides an anti-TIM-3 antibody or an antigen-binding portion thereof, wherein said antibody comprises H-CDR1-3 and L-CDR1-3 comprising the amino acid sequences of SEQ ID NOs: 7-12, respectively.

In certain embodiments, the invention provides an anti-TIM-3 antibody or an antigen-binding portion thereof, wherein said antibody comprises a VH comprising the amino acid sequence of SEQ ID NO: 15 and a VL comprising the amino acid sequence of SEQ ID NO: 4.

In particular embodiments, the invention provides an anti-TIM-3 antibody that comprises a heavy chain comprising the amino acid sequences of SEQ ID NOs: 15 and 25 and a light chain comprising the amino acid sequences of SEQ ID NOs: 4 and 6.

The invention also provides an anti-TIM-3 antibody or an antigen-binding portion thereof that binds to an epitope of TIM-3 comprising amino acid residues F61 and I117 of SEQ ID NO: 236 (e.g., antibody 15086.15086, 15086.16837, 15086.17145, 15086.17144, 20293, or 20131). In some embodiments, the epitope further comprises amino acid residue R69 (e.g., antibody 15086.15086, 15086.16837, 15086.17145, 15086.17144, or 20293). In other embodiments, the epitope further comprises P50, E62, M118, and D120 (e.g., antibody 15086.15086, 15086.16837, 15086.17145, 15086.17144, or 20131) and may additionally comprise amino acid residues R69, V60, and G64 (e.g., antibody 15086.15086, 15086.16837, 15086.17145, or 15086.17144).

In particular embodiments, the antibody or portion binds to an epitope of TIM-3 comprising amino acid residues P50, V60, F61, E62, G64, R69, I117, M118, and D120 of SEQ ID NO: 236 (e.g., antibody 15086.15086, 15086.16837, 15086.17145, or 15086.17144), amino acid residues F61, R69, and I117 of SEQ ID NO: 236 (e.g., antibody 20293), or amino acid residues P50, F61, E62, I117, M118, and D120 of SEQ ID NO: 236 (e.g., antibody 20131).

The invention also provides a monoclonal antibody or an antigen-binding portion thereof that binds to an epitope of TIM-3 comprising amino acid residues 62-67 of SEQ ID NO: 236 (e.g., antibody 15086.15086, 15086.16837, 15086.17145, 15086.17144, or 20293). Further, the invention provides a monoclonal antibody or an antigen-binding portion thereof that binds to an epitope of TIM-3 comprising amino acid residues 114-117 of SEQ ID NO: 236 (e.g., antibody 20131).

In some embodiments, the anti-TIM-3 antibody is an IgG antibody, e.g., a human IgG antibody. In certain embodiments, the antibody comprises at least one mutation in the $F_C$ region. In particular embodiments, the antibody comprises a mutation in one or more of heavy chain amino acid positions 228, 233, 234 and 235, which are numbered according to the IMGT numbering scheme. For example, one or both of the amino acid residues at positions 234 and 235 may be mutated to Ala, and/or the amino acid residue at position 228 may be mutated to Pro.

In some embodiments, the anti-TIM-3 antibody or antigen-binding portion of the invention has at least one of the following properties:

a) binds to human TIM-3 with a $K_D$ of 23 nM or less as measured by surface plasmon resonance;

b) binds to cynomolgus TIM-3 with a $K_D$ of 22 nM or less as measured by surface plasmon resonance;

c) binds to human TIM-3 with an EC50 of 1.2 nM or less as measured by ELISA;

d) binds to cynomolgus TIM-3 with an EC50 of 46 nM or less as measured by ELISA;

e) increases IFN-γ secretion in a one-way mixed lympho-
    cyte reaction assay;

f) increases IFN-γ secretion in a two-way mixed lympho-
    cyte reaction assay;

g) increases TNF-α secretion in a one-way mixed lym-
    phocyte reaction assay;

h) increases TNF-α secretion from dendritic cells; and i) inhibits interaction of TIM-3 with phosphatidylserine.

Examples of such an antibody include, without limitation,
antibody 15086.15086 (having at least properties a, c, d, e,
g, and h); antibody 15086.17145 (having at least properties
a, c, d, e, g, h, and i), antibody 15086.16837 or 15086.17144
(having at least properties a, c, and d), antibody 20293 or
20131 (having at least properties a, b, c, d, e, f, and h),
antibody 20362 (having at least properties c, e, f, and h), and
antibody 19324, 19416, 19568, 20185, 20300, or 20621
(having at least properties c, d, e, f, and h). In some
embodiments, the anti-TIM-3 antibody or antigen-binding
portion of the invention has all of said properties. In some
embodiments, the anti-TIM-3 antibody or antigen-binding
portion has at least properties a, c, d, e, g, and h. In some
embodiments, the anti-TIM-3 antibody or antigen-binding
portion has at least properties a, c, d, e, g, h, and i. In some
embodiments, the anti-TIM-3 antibody or antigen-binding
portion has at least properties a, c, and d. In some embodi-
ments, the anti-TIM-3 antibody or antigen-binding portion
has at least properties a, b, c, d, e, f, and h. In some
embodiments, the anti-TIM-3 antibody or antigen-binding
portion has at least properties c, e, f, and h. In some
embodiments, the anti-TIM-3 antibody or antigen-binding
portion has at least properties c, d, e, f, and h.

In some embodiments, the anti-TIM-3 antibody or anti-
gen-binding portion of the invention increases the activity of
NK cells. In some embodiments, this activity can mediate
ADCC.

In some embodiments, the anti-TIM-3 antibody or anti-
gen-binding portion of the invention does not compete for
binding to TIM-3 with ABTIM3 (from PCT Publication WO
2015/117002) and/or mAb15 (from PCT Publication WO
2016/111947). In some embodiments, the anti-TIM-3 anti-
body or antigen-binding portion of the invention does not
bind to the same epitope as ABTIM3 and/or mAB15; for
example, the antibody or portion of the invention binds to
one or more residues on TIM-3 that are not bound by
ABTIM3 and/or mAb15.

In other aspects, the present invention provides pharma-
ceutical compositions comprising at least one anti-TIM-3
antibody or antigen-binding portion thereof as described
herein and a pharmaceutically acceptable excipient, option-
ally with an additional therapeutic, such as a chemothera-
peutic agent, an anti-neoplastic agent, an anti-angiogenic
agent, a tyrosine kinase inhibitor, or a TIM-3 pathway
inhibitor.

The present invention further provides isolated nucleic
acid molecules comprising a nucleotide sequence that
encodes the heavy chain or an antigen-binding portion
thereof, a nucleotide sequence that encodes the light chain or
an antigen-binding portion thereof, or both, of an anti-TIM-3
antibody or antigen-binding portion as described herein.

The present invention also provides vectors comprising
such an isolated nucleic acid molecule, wherein said vector
optionally further comprises an expression control sequence.

The present invention also provide host cells comprising
a nucleotide sequence that encodes the heavy chain or an
antigen-binding portion thereof, a nucleotide sequence that encodes the light chain or an antigen-binding portion
thereof, or both, of an anti-TIM-3 antibody as described
herein.

The present invention also provides a method for produc-
ing an anti-TIM-3 antibody or antigen-binding portion
thereof as described herein, comprising providing a host cell
that comprises a nucleotide sequence that encodes the heavy
chain or an antigen-binding portion thereof and a nucleotide
sequence that encodes the light chain or an antigen-binding
portion thereof of an anti-TIM-3 antibody or antigen-bind-
ing portion as described herein, culturing said host cell under
conditions suitable for expression of the antibody or portion,
and isolating the resulting antibody or portion.

The present invention also provides a multi-specific (e.g.,
bispecific) binding molecule having an antigen-binding por-
tion of an anti-TIM-3 antibody described herein and an
antigen-binding portion of another, distinct antibody, such as
of another anti-TIM-3 antibody (e.g., another anti-TIM-3
antibody described herein) or an antibody that targets a
different protein, such as another immune checkpoint pro-
tein, a cancer antigen, or another cell surface molecule
whose activity mediates a disease condition such as cancer.

The present invention also provides a method for enhanc-
ing immunity in a patient (e.g., a human patient), comprising
administering to said patient an anti-TIM-3 antibody or an
antigen-binding portion thereof or a multi-specific (e.g.,
bispecific) binding molecule as described herein.

The present invention further provides a method for
treating cancer in a patient (e.g., a human patient), compris-
ing administering to said patient an anti-TIM-3 antibody or
an antigen-binding portion thereof or a multi-specific (e.g.,
bispecific) binding molecule as described herein. In some
embodiments, the cancer originates in a tissue selected from
the group consisting of skin, lung, intestine, ovary, brain,
prostate, kidney, soft tissues, hematopoietic system, head
and neck, liver, bladder, breast, stomach, uterus and pan-
creas. In some embodiments, the patient has leukemia (e.g.,
acute myeloid leukemia), Hodgkin's lymphoma, or non-
Hodgkin's lymphoma. In some embodiments, the patient
has a solid tumor (e.g., an advanced or metastatic solid
tumor). In some embodiments, the patient has melanoma,
non-small cell lung cancer, colorectal cancer, or renal cell
carcinoma. In certain embodiments, the method further
comprises administering a chemotherapeutic agent, an anti-
neoplastic agent, an anti-angiogenic agent, a tyrosine kinase
inhibitor, and/or a TIM-3 pathway inhibitor.

The present invention further provides anti-TIM-3 anti-
bodies or antigen-binding portions or multi-specific (e.g.,
bi-specific) binding molecules as described herein for use in
the aforementioned treatments; the use of said antibodies,
antigen-binding portions, or multi-specific binding mol-
ecules as medicaments for the aforementioned treatments;
and the use of said antibodies, antigen-binding portions, or
multi-specific binding molecules for the preparation of
medicaments for the aforementioned treatments, i.e., treat-
ment of a human patient in need thereof to enhance his/her
immune system, and treatment of a human patient with
cancer, such as one of the aforementioned cancers. The
present invention also provide articles of manufacture com-
prising the anti-TIM-3 antibodies or antigen-binding por-
tions or multi-specific (e.g., bi-specific) binding molecules
described herein, as well as methods for manufacturing said
articles of manufacture.

DETAILED DESCRIPTION OF THE INVENTION

Figure 1:
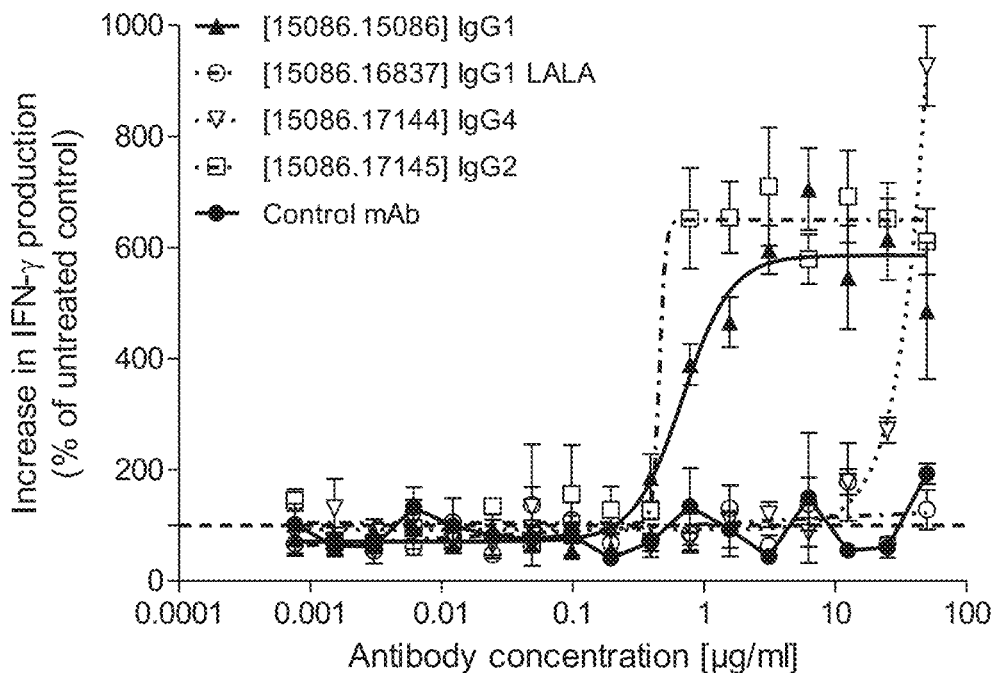
FIG. 1 shows dose-response curves of antibodies
15086.15086, 15086.16837, 15086.17145, and 15086.17144
for IFN-γ production in a one-way mixed lymphocyte reac-
tion (MLR) assay.

The present invention provides new anti-human TIM-3 antibodies that can be used to enhance the immune system in a human patient, such as a cancer patient. Unless otherwise stated, as used herein, "TIM-3" refers to human TIM-3. A human TIM-3 polypeptide sequence is available under Uniprot Accession No. Q8TDQ0 (HAVR2_HUMAN), shown here as SEQ ID NO: 236.

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers in the heavy or light chain may be in accordance with IMGT® definitions (Lefranc et al., *Dev Comp Immunol* 27(1):55-77 (2003)); or the definitions of Kabat, *Sequences of Proteins of Immunological Interest* (National Institutes of Health, Bethesda, MD (1987 and 1991)); Chothia and Lesk, *J. Mol. Biol.* 196:901-917 (1987); or Chothia et al., *Nature* 342:878-883 (1989).

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, the term "germline" refers to the nucleotide and amino acid sequences of antibody genes and gene segments as they are passed from parents to offspring via germ cells. Germline sequences are distinguished from the nucleotide sequences encoding antibodies in mature B cells, which have been altered by recombination and hypermutation events during the course of B cell maturation. An antibody that "utilizes" a particular germline sequence has a nucleotide or amino acid sequence that aligns with that germline nucleotide sequence or with the amino acid sequence that it specifies more closely than with any other germline nucleotide or amino acid sequence.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is ≤1 mM, preferably ≤100 nM. A $K_D$ binding affinity constant can be measured, e.g., by surface plasmon resonance (BIA-core™) or Bio-Layer Interferometry, for example using the ProteOn™ XPR36 SPR system from Bio-Rad or the Octet™ system.

The term "$k_{off}$" refers to the dissociation rate constant of a particular antibody-antigen interaction. A $k_{off}$ dissociation rate constant can be measured by Bio-Layer Interferometry, for example using the Octet™ system.

The term "epitope" as used herein refers to a portion (determinant) of an antigen that specifically binds to an antibody or a related molecule such as a bispecific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest or a relevant portion thereof (e.g., the ECD of TIM-3), then screening for binding to the epitope.

One can determine whether an antibody binds to the same epitope as or competes for binding with an anti-TIM-3 antibody of the invention by using methods known in the art, including, without limitation, competition assays, epitope binning, and alanine scanning. In some embodiments, the test antibody and an anti-TIM-3 antibody of the invention bind to at least one common residue (e.g., at least two, three, four, five, six, seven, eight, or nine common residues) on TIM-3. In further embodiments, the contact residues on TIM-3 are completely identical between the test antibody and the anti-TIM-3 antibody of the invention. In one embodiment, one allows the anti-TIM-3 antibody of the invention to bind to TIM-3 under saturating conditions and then measures the ability of the test antibody to bind to TIM-3. If the test antibody is able to bind to TIM-3 at the same time as the reference anti-TIM-3 antibody, then the test antibody binds to a different epitope than the reference anti-TIM-3 antibody. However, if the test antibody is not able to bind to TIM-3 at the same time, then the test antibody binds to the same epitope, an overlapping epitope, or an epitope that is in close proximity to the epitope bound by the anti-TIM-3 antibody of the invention. This experiment can be performed using, e.g., ELISA, RIA, BIACORE™, Bio-Layer Interferometry or flow cytometry. To test whether an anti-TIM-3 antibody cross-competes with another anti-TIM-3 antibody, one may use the competition method described above in two directions, i.e., determining if the known antibody blocks the test antibody and vice versa. Such cross-competition experiments may be performed, e.g., using an IBIS MX96 SPR instrument or the Octet™ system.

In certain cases, it may be desirable to alter one or more CDR amino acid residues in order to improve binding affinity to the target epitope. This is known as "affinity maturation." Various affinity maturation methods are known in the art, for example the in vitro scanning saturation mutagenesis method described by Burks et al., *Proc Natl Acad Sci USA,* 94:412-417 (1997), and the stepwise in vitro affinity maturation method of Wu et al., *Proc Natl Acad Sci USA* 95:6037-6042 (1998).

The term "antigen-binding portion" of an antibody (or simply "antibody portion"), as used herein, refers to one or more portions or fragments of an antibody that retain the ability to specifically bind to an antigen (e.g., human TIM-3, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, $C_L$ and $C_H1$ domains; (ii) a F(ab')$_2$ fragment: a bivalent fragment comprising two Fab fragments linked by a disulfide bridge at the hinge region; (iii) an Fd fragment consisting of the $V_H$ and $C_H1$ domains; (iv) a Fv fragment consisting of the $V_L$ and $V_H$ domains of a single arm of an antibody, (v) a dAb fragment, which consists of a $V_H$ domain; and (vi) an isolated complementarity determining region (CDR) capable of specifically binding to an antigen. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ domains pair to form monovalent molecules (known as single chain Fv (scFv)). Also within the invention are antigen-binding molecules comprising a $V_H$ and/or a $V_L$. In the case of a $V_H$, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

The class (isotype) and subclass of anti-TIM-3 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

When referring to particular amino acid residues in a given position of an antibody sequence, an indication of, e.g., "35S" refers to the position and residue, i.e., in this case indicating that a serine residue (S) is present in position 35 of the sequence. Similarly, an indication of, e.g., "13Q+35S" refers to the two residues in the respective positions.

Unless otherwise indicated, all antibody amino acid residue numbers referred to in this disclosure are those under the IMGT® numbering scheme.

Anti-TIM-3 Antibodies

The present invention provides antibodies directed against TIM-3, and antigen-binding portions thereof. In a particular embodiment, the antibodies disclosed herein are human antibodies generated from transgenic rats that are able to generate antibodies with human idiotypes.

An advantage of the novel anti-TIM-3 antibodies of the invention is that they can potently activate dendritic cells (see, e.g., Example 4). While not wishing to be bound by any particular theory, it is believed that the anti-TIM-3 antibodies of the invention are able to stimulate T cells (e.g., tumor-specific T cells) through activation of dendritic cells.

Further, the present application demonstrates for the first time that anti-TIM-3 antibodies of isotype IgG1 or IgG2 have high levels of activity while antibodies of isotype IgG4 or IgG1-LALA are non-functional or poorly functional (see, e.g., Examples 3 and 4). Without wishing to be bound by any particular theory, the inventors' data suggest that an anti-TIM-3 antibody that can cross-link TIM-3 via Fc receptors is a particularly potent activator of the immune system. For example, an anti-TIM-3 IgG2 antibody of the invention can bind to FcγR2A found on dendritic cells, and is believed to activate dendritic cells by cross-linking the TIM-3 molecules on them.

The anti-TIM-3 antibodies disclosed herein may be referred to by either a 5-digit number, e.g. "20131", or by a 10-digit number, e.g. "15086.16837". 10-digit numbers with the same first five digits are derived from the same parent antibody, as in the case of antibodies 15086.15086, 15086.16837, 15086.17145, 15086.17144. Such antibodies, which share the same six CDRs, are expected to have the same or substantially the same target binding properties. As will be apparent from the protein and DNA sequences provided herein, the 15086.16837, 15086.17145, and 15086.17144 variants have only a single amino acid difference in the VH sequence compared to the parent 15086 antibody ("15086.15086"), namely E, rather than Q, in position 6, whereas the VL amino acid sequences are identical. It will also be apparent that these variants differ primarily by their antibody format/subclass, i.e.:

15086.15086: IgG1
15086.16837: IgG1 LALA
15086.17145: IgG2
15086.17144: IgG4

In some embodiments, the anti-TIM-3 antibody is selected from the group consisting of:

a) an antibody whose H-CDR1-3 comprise the amino acid sequences of SEQ ID NOs: 7-9, respectively;
b) an antibody whose heavy chain variable domain (VH) is at least 90% identical in sequence to the amino acid sequence of SEQ ID NO: 3;
c) an antibody whose VH comprises the amino acid sequence of SEQ ID NO: 3;
d) an antibody whose heavy chain (HC) comprises the amino acid sequences of SEQ ID NOs: 3 and 5;
e) an antibody whose L-CDR1-3 comprise the amino acid sequences of SEQ ID NOs: 10-12, respectively;
f) an antibody whose light chain variable domain (VL) is at least 90% identical in sequence to the amino acid sequence of SEQ ID NO: 4;
g) an antibody whose VL comprises the amino acid sequence of SEQ ID NO: 4;
h) an antibody whose light chain (LC) comprises the amino acid sequences of SEQ ID NOs: 4 and 6;
i) an antibody whose H-CDR1-3 and L-CDR1-3 comprise the amino acid sequences of SEQ ID NOs: 7-12, respectively;
j) an antibody whose VH is at least 90% identical in sequence to the amino acid sequence of SEQ ID NO: 3 and whose VL is at least 90% identical in sequence to the amino acid sequence of SEQ ID NO: 4;
k) an antibody whose VH comprises the amino acid sequence of SEQ ID NO: 3 and whose VL comprises the amino acid sequence of SEQ ID NO: 4; and
l) an antibody whose HC comprises the amino acid sequences of SEQ ID NOs: 3 and 5; and whose LC comprises the amino acid sequences of SEQ ID NOs: 4 and 6.

In some embodiments, the anti-TIM-3 antibody is selected from the group consisting of:

a) an antibody whose H-CDR1-3 comprise the amino acid sequences of SEQ ID NOs: 7-9, respectively;
b) an antibody whose heavy chain variable domain (VH) is at least 90% identical in sequence to the amino acid sequence of SEQ ID NO: 15;
c) an antibody whose VH comprises the amino acid sequence of SEQ ID NO: 15;
d) an antibody whose heavy chain (HC) comprises the amino acid sequence of SEQ ID NOs: 15 and 25;
e) an antibody whose L-CDR1-3 comprise the amino acid sequences of SEQ ID NOs: 10-12, respectively;
f) an antibody whose light chain variable domain (VL) is at least 90% identical in sequence to the amino acid sequence of SEQ ID NO: 4;
g) an antibody whose VL comprises the amino acid sequence of SEQ ID NO: 4;
h) an antibody whose light chain (LC) comprises the amino acid sequences of SEQ ID NOs: 4 and 6;
i) an antibody whose H-CDR1-3 and L-CDR1-3 comprise the amino acid sequences of SEQ ID NOs: 7-12, respectively;
j) an antibody whose VH is at least 90% identical in sequence to the amino acid sequence of SEQ ID NO: 15 and whose VL is at least 90% identical in sequence to the amino acid sequence of SEQ ID NO: 4;
k) an antibody whose VH comprises the amino acid sequence of SEQ ID NO: 15 and whose VL comprises the amino acid sequence of SEQ ID NO: 4; and
l) an antibody whose HC comprises the amino acid sequences of SEQ ID NOs: 15 and 25; and whose LC comprises the amino acid sequences of SEQ ID NOs: 4 and 6.

In some embodiments, the anti-TIM-3 antibody is selected from the group consisting of:

a) an antibody whose H-CDR1-3 comprise the amino acid sequences of SEQ ID NOs: 7-9, respectively;
b) an antibody whose heavy chain variable domain (VH) is at least 90% identical in sequence to the amino acid sequence of SEQ ID NO: 15;
c) an antibody whose VH comprises the amino acid sequence of SEQ ID NO: 15;
d) an antibody whose heavy chain (HC) comprises the amino acid sequence of SEQ ID NO: 15 and the amino acid sequence of SEQ ID NO: 23 or 24;
e) an antibody whose L-CDR1-3 comprise the amino acid sequences of SEQ ID NOs: 10-12, respectively;
f) an antibody whose light chain variable domain (VL) is at least 90% identical in sequence to the amino acid sequence of SEQ ID NO: 4;
g) an antibody whose VL comprises the amino acid sequence of SEQ ID NO: 4;
h) an antibody whose light chain (LC) comprises the amino acid sequences of SEQ ID NOs: 4 and 6;
i) an antibody whose H-CDR1-3 and L-CDR1-3 comprise the amino acid sequences of SEQ ID NOs: 7-12, respectively;
j) an antibody whose VH is at least 90% identical in sequence to the amino acid sequence of SEQ ID NO: 15 and whose VL is at least 90% identical in sequence to the amino acid sequence of SEQ ID NO: 4;
k) an antibody whose VH comprises the amino acid sequence of SEQ ID NO: 15 and whose VL comprises the amino acid sequence of SEQ ID NO: 4; and
l) an antibody whose HC comprises the amino acid sequence of SEQ ID NO: 15 and the amino acid sequence of SEQ ID NO: 23 or 24; and whose LC comprises the amino acid sequences of SEQ ID NOs: 4 and 6.

In some embodiments, the anti-TIM-3 antibody is selected from the group consisting of:

a) an antibody whose H-CDR1-3 comprise the amino acid sequences of SEQ ID NOs: 30-32, respectively;

b) an antibody whose heavy chain variable domain (VH) is at least 90% identical in sequence to the amino acid sequence of SEQ ID NO: 28;

c) an antibody whose VH comprises the amino acid sequence of SEQ ID NO: 28;

d) an antibody whose heavy chain (HC) comprises the amino acid sequences of SEQ ID NO: 28 and SEQ ID NO: 5, 23, 24, or 25;

e) an antibody whose L-CDR1-3 comprise the amino acid sequences of SEQ ID NOs: 33-35, respectively;

f) an antibody whose light chain variable domain (VL) is at least 90% identical in sequence to the amino acid sequence of SEQ ID NO: 29;

g) an antibody whose VL comprises the amino acid sequence of SEQ ID NO: 29;

h) an antibody whose light chain (LC) comprises the amino acid sequences of SEQ ID NOs: 29 and 6;

i) an antibody whose H-CDR1-3 and L-CDR1-3 comprise the amino acid sequences of SEQ ID NOs: 30-35, respectively;

j) an antibody whose VH is at least 90% identical in sequence to the amino acid sequence of SEQ ID NO: 28 and whose VL is at least 90% identical in sequence to the amino acid sequence of SEQ ID NO: 29;

k) an antibody whose VH comprises the amino acid sequence of SEQ ID NO: 28 and whose VL comprises the amino acid sequence of SEQ ID NO: 29; and l) an antibody whose HC comprises the amino acid sequence of SEQ ID NO: 28 and the amino acid sequence of SEQ ID NO: 5, 23, 24, or 25; and whose LC comprises the amino acid sequences of SEQ ID NOs: 29 and 6.

In some embodiments, the anti-TIM-3 antibody is selected from the group consisting of:

a) an antibody whose H-CDR1-3 comprise the amino acid sequences of SEQ ID NOs: 40-42, respectively;

b) an antibody whose heavy chain variable domain (VH) is at least 90% identical in sequence to the amino acid sequence of SEQ ID NO: 38;

c) an antibody whose VH comprises the amino acid sequence of SEQ ID NO: 38;

d) an antibody whose heavy chain (HC) comprises the amino acid sequences of SEQ ID NO: 38 and SEQ ID NO: 5, 23, 24, or 25;

e) an antibody whose L-CDR1-3 comprise the amino acid sequences of SEQ ID NOs: 43-45, respectively;

f) an antibody whose light chain variable domain (VL) is at least 90% identical in sequence to the amino acid sequence of SEQ ID NO: 39;

g) an antibody whose VL comprises the amino acid sequence of SEQ ID NO: 39;

h) an antibody whose light chain (LC) comprises the amino acid sequences of SEQ ID NOs: 39 and 6;

i) an antibody whose H-CDR1-3 and L-CDR1-3 comprise the amino acid sequences of SEQ ID NOs: 40-45, respectively;

j) an antibody whose VH is at least 90% identical in sequence to the amino acid sequence of SEQ ID NO: 38 and whose VL is at least 90% identical in sequence to the amino acid sequence of SEQ ID NO: 39;

k) an antibody whose VH comprises the amino acid sequence of SEQ ID NO: 38 and whose VL comprises the amino acid sequence of SEQ ID NO: 39; and l) an antibody whose HC comprises the amino acid sequence of SEQ ID NO: 38 and the amino acid sequence of SEQ ID NO: 5, 23, 24, or 25; and whose LC comprises the amino acid sequences of SEQ ID NOs: 39 and 6.

In some embodiments, the anti-TIM-3 antibody is selected from the group consisting of:

a) an antibody whose H-CDR1-3 comprise the amino acid sequences of SEQ ID NOs: 50-52, respectively;

b) an antibody whose heavy chain variable domain (VH) is at least 90% identical in sequence to the amino acid sequence of SEQ ID NO: 48;

c) an antibody whose VH comprises the amino acid sequence of SEQ ID NO: 48;

d) an antibody whose heavy chain (HC) comprises the amino acid sequences of SEQ ID NO: 48 and SEQ ID NO: 5, 23, 24, or 25;

e) an antibody whose L-CDR1-3 comprise the amino acid sequences of SEQ ID NOs: 53-55, respectively;

f) an antibody whose light chain variable domain (VL) is at least 90% identical in sequence to the amino acid sequence of SEQ ID NO: 49;

g) an antibody whose VL comprises the amino acid sequence of SEQ ID NO: 49;

h) an antibody whose light chain (LC) comprises the amino acid sequences of SEQ ID NOs: 49 and 6;

i) an antibody whose H-CDR1-3 and L-CDR1-3 comprise the amino acid sequences of SEQ ID NOs: 50-55, respectively;

j) an antibody whose VH is at least 90% identical in sequence to the amino acid sequence of SEQ ID NO: 48 and whose VL is at least 90% identical in sequence to the amino acid sequence of SEQ ID NO: 49;

k) an antibody whose VH comprises the amino acid sequence of SEQ ID NO: 48 and whose VL comprises the amino acid sequence of SEQ ID NO: 49; and l) an antibody whose HC comprises the amino acid sequence of SEQ ID NO: 48 and the amino acid sequence of SEQ ID NO: 5, 23, 24, or 25; and whose LC comprises the amino acid sequences of SEQ ID NOs: 49 and 6.

In some embodiments, the anti-TIM-3 antibody is selected from the group a) an antibody whose H-CDR1-3 comprise the amino acid sequences of SEQ ID NOs: 60-62, respectively;

b) an antibody whose heavy chain variable domain (VH) is at least 90% identical in sequence to the amino acid sequence of SEQ ID NO: 58;

c) an antibody whose VH comprises the amino acid sequence of SEQ ID NO: 58;

d) an antibody whose heavy chain (HC) comprises the amino acid sequences of SEQ ID NO: 58 and SEQ ID NO: 5, 23, 24, or 25;

e) an antibody whose L-CDR1-3 comprise the amino acid sequences of SEQ ID NOs: 63-65, respectively;

f) an antibody whose light chain variable domain (VL) is at least 90% identical in sequence to the amino acid sequence of SEQ ID NO: 59;

g) an antibody whose VL comprises the amino acid sequence of SEQ ID NO: 59;

h) an antibody whose light chain (LC) comprises the amino acid sequences of SEQ ID NOs: 59 and 6;

i) an antibody whose H-CDR1-3 and L-CDR1-3 comprise the amino acid sequences of SEQ ID NOs: 60-65, respectively;

j) an antibody whose VH is at least 90% identical in sequence to the amino acid sequence of SEQ ID NO: 58 and whose VL is at least 90% identical in sequence to the amino acid sequence of SEQ ID NO: 59;

k) an antibody whose VH comprises the amino acid sequence of SEQ ID NO: 58 and whose VL comprises the amino acid sequence of SEQ ID NO: 59; and l) an antibody whose HC comprises the amino acid sequence of SEQ ID NO: 58 and the amino acid sequence of SEQ ID NO: 5, 23, 24, or 25; and whose LC comprises the amino acid sequences of SEQ ID NOs: 59 and 6.

In some embodiments, the anti-TIM-3 antibody is selected from the group consisting of:

a) an antibody whose H-CDR1-3 comprise the amino acid sequences of SEQ ID NOs: 70-72, respectively;

b) an antibody whose heavy chain variable domain (VH) is at least 90% identical in sequence to the amino acid sequence of SEQ ID NO: 68;

c) an antibody whose VH comprises the amino acid sequence of SEQ ID NO: 68;

d) an antibody whose heavy chain (HC) comprises the amino acid sequences of SEQ ID NO: 68 and SEQ ID NO: 5, 23, 24, or 25;

e) an antibody whose L-CDR1-3 comprise the amino acid sequences of SEQ ID NOs: 73-75, respectively;

f) an antibody whose light chain variable domain (VL) is at least 90% identical in sequence to the amino acid sequence of SEQ ID NO: 69;

g) an antibody whose VL comprises the amino acid sequence of SEQ ID NO: 69;

h) an antibody whose light chain (LC) comprises the amino acid sequences of SEQ ID NOs: 69 and 6;

i) an antibody whose H-CDR1-3 and L-CDR1-3 comprise the amino acid sequences of SEQ ID NOs: 70-75, respectively;

j) an antibody whose VH is at least 90% identical in sequence to the amino acid sequence of SEQ ID NO: 68 and whose VL is at least 90% identical in sequence to the amino acid sequence of SEQ ID NO: 69;

k) an antibody whose VH comprises the amino acid sequence of SEQ ID NO: 68 and whose VL comprises the amino acid sequence of SEQ ID NO: 69; and l) an antibody whose HC comprises the amino acid sequence of SEQ ID NO: 68 and the amino acid sequence of SEQ ID NO: 5, 23, 24, or 25; and whose LC comprises the amino acid sequences of SEQ ID NOs: 69 and 6.

In some embodiments, the anti-TIM-3 antibody is selected from the group consisting of:

a) an antibody whose H-CDR1-3 comprise the amino acid sequences of SEQ ID NOs: 80-82, respectively;

b) an antibody whose heavy chain variable domain (VH) is at least 90% identical in sequence to the amino acid sequence of SEQ ID NO: 78;

c) an antibody whose VH comprises the amino acid sequence of SEQ ID NO: 78;

d) an antibody whose heavy chain (HC) comprises the amino acid sequences of SEQ ID NO: 78 and SEQ ID NO: 5, 23, 24, or 25;

e) an antibody whose L-CDR1-3 comprise the amino acid sequences of SEQ ID NOs: 83-85, respectively;

f) an antibody whose light chain variable domain (VL) is at least 90% identical in sequence to the amino acid sequence of SEQ ID NO: 79;

g) an antibody whose VL comprises the amino acid sequence of SEQ ID NO: 79;

h) an antibody whose light chain (LC) comprises the amino acid sequences of SEQ ID NOs: 79 and 6;

i) an antibody whose H-CDR1-3 and L-CDR1-3 comprise the amino acid sequences of SEQ ID NOs: 80-85, respectively;

j) an antibody whose VH is at least 90% identical in sequence to the amino acid sequence of SEQ ID NO: 78 and whose VL is at least 90% identical in sequence to the amino acid sequence of SEQ ID NO: 79;

k) an antibody whose VH comprises the amino acid sequence of SEQ ID NO: 78 and whose VL comprises the amino acid sequence of SEQ ID NO: 79; and l) an antibody whose HC comprises the amino acid sequence of SEQ ID NO: 78 and the amino acid sequence of SEQ ID NO: 5, 23, 24, or 25; and whose LC comprises the amino acid sequences of SEQ ID NOs: 79 and 6.

In some embodiments, the anti-TIM-3 antibody is selected from the group consisting of:

a) an antibody whose H-CDR1-3 comprise the amino acid sequences of SEQ ID NOs: 90-92, respectively;

b) an antibody whose heavy chain variable domain (VH) is at least 90% identical in sequence to the amino acid sequence of SEQ ID NO: 88;

c) an antibody whose VH comprises the amino acid sequence of SEQ ID NO: 88;

d) an antibody whose heavy chain (HC) comprises the amino acid sequences of SEQ ID NO: 88 and SEQ ID NO: 5, 23, 24, or 25;

e) an antibody whose L-CDR1-3 comprise the amino acid sequences of SEQ ID NOs: 93-95, respectively;

f) an antibody whose light chain variable domain (VL) is at least 90% identical in sequence to the amino acid sequence of SEQ ID NO: 89;

g) an antibody whose VL comprises the amino acid sequence of SEQ ID NO: 89;

h) an antibody whose light chain (LC) comprises the amino acid sequences of SEQ ID NOs: 89 and 6;

i) an antibody whose H-CDR1-3 and L-CDR1-3 comprise the amino acid sequences of SEQ ID NOs: 90-95, respectively;

j) an antibody whose VH is at least 90% identical in sequence to the amino acid sequence of SEQ ID NO: 88 and whose VL is at least 90% identical in sequence to the amino acid sequence of SEQ ID NO: 89;

k) an antibody whose VH comprises the amino acid sequence of SEQ ID NO: 88 and whose VL comprises the amino acid sequence of SEQ ID NO: 89; and l) an antibody whose HC comprises the amino acid sequence of SEQ ID NO: 88 and the amino acid sequence of SEQ ID NO: 5, 23, 24, or 25; and whose LC comprises the amino acid sequences of SEQ ID NOs: 89 and 6.

In some embodiments, the anti-TIM-3 antibody is selected from the group consisting of:

a) an antibody whose H-CDR1-3 comprise the amino acid sequences of SEQ ID NOs: 100-102, respectively;

b) an antibody whose heavy chain variable domain (VH) is at least 90% identical in sequence to the amino acid sequence of SEQ ID NO: 98;

c) an antibody whose VH comprises the amino acid sequence of SEQ ID NO: 98;

d) an antibody whose heavy chain (HC) comprises the amino acid sequences of SEQ ID NO: 98 and SEQ ID NO: 5, 23, 24, or 25;

e) an antibody whose L-CDR1-3 comprise the amino acid sequences of SEQ ID NOs: 103-105, respectively;

f) an antibody whose light chain variable domain (VL) is at least 90% identical in sequence to the amino acid sequence of SEQ ID NO: 99;

g) an antibody whose VL comprises the amino acid sequence of SEQ ID NO: 99;

h) an antibody whose light chain (LC) comprises the amino acid sequences of SEQ ID NOs: 99 and 6;

i) an antibody whose H-CDR1-3 and L-CDR1-3 comprise the amino acid sequences of SEQ ID NOs: 100-105, respectively;

j) an antibody whose VH is at least 90% identical in sequence to the amino acid sequence of SEQ ID NO: 98 and whose VL is at least 90% identical in sequence to the amino acid sequence of SEQ ID NO: 99;

k) an antibody whose VH comprises the amino acid sequence of SEQ ID NO: 98 and whose VL comprises the amino acid sequence of SEQ ID NO: 99; and l) an antibody whose HC comprises the amino acid sequence of SEQ ID NO: 98 and the amino acid sequence of SEQ ID NO: 5, 23, 24, or 25; and whose LC comprises the amino acid sequences of SEQ ID NOs: 99 and 6.

In some embodiments, the anti-TIM-3 antibody is selected from the group consisting of:

a) an antibody whose H-CDR1-3 comprise the amino acid sequences of SEQ ID NOs: 110-112, respectively;

b) an antibody whose heavy chain variable domain (VH) is at least 90% identical in sequence to the amino acid sequence of SEQ ID NO: 108;

c) an antibody whose VH comprises the amino acid sequence of SEQ ID NO: 108;

d) an antibody whose heavy chain (HC) comprises the amino acid sequences of SEQ ID NO: 108 and SEQ ID NO: 5, 23, 24, or 25;

e) an antibody whose L-CDR1-3 comprise the amino acid sequences of SEQ ID NOs: 113-115, respectively;

f) an antibody whose light chain variable domain (VL) is at least 90% identical in sequence to the amino acid sequence of SEQ ID NO: 109;

g) an antibody whose VL comprises the amino acid sequence of SEQ ID NO: 109;

h) an antibody whose light chain (LC) comprises the amino acid sequences of SEQ ID NOs: 109 and 6;

i) an antibody whose H-CDR1-3 and L-CDR1-3 comprise the amino acid sequences of SEQ ID NOs: 110-115, respectively;

j) an antibody whose VH is at least 90% identical in sequence to the amino acid sequence of SEQ ID NO: 108 and whose VL is at least 90% identical in sequence to the amino acid sequence of SEQ ID NO: 109;

k) an antibody whose VH comprises the amino acid sequence of SEQ ID NO: 108 and whose VL comprises the amino acid sequence of SEQ ID NO: 109; and l) an antibody whose HC comprises the amino acid sequence of SEQ ID NO: 108 and the amino acid sequence of SEQ ID NO: 5, 23, 24, or 25; and whose LC comprises the amino acid sequences of SEQ ID NOs: 109 and 6.

In some embodiments, the anti-TIM-3 antibody is selected from the group consisting of:

a) an antibody whose H-CDR1-3 comprise the amino acid sequences of SEQ ID NOs: 120-122, respectively;

b) an antibody whose heavy chain variable domain (VH) is at least 90% identical in sequence to the amino acid sequence of SEQ ID NO: 118;

c) an antibody whose VH comprises the amino acid sequence of SEQ ID NO: 118;

d) an antibody whose heavy chain (HC) comprises the amino acid sequences of SEQ ID NO: 118 and SEQ ID NO: 5, 23, 24, or 25;

e) an antibody whose L-CDR1-3 comprise the amino acid sequences of SEQ ID NOs: 123-125, respectively;

f) an antibody whose light chain variable domain (VL) is at least 90% identical in sequence to the amino acid sequence of SEQ ID NO: 119;

g) an antibody whose VL comprises the amino acid sequence of SEQ ID NO: 119;

h) an antibody whose light chain (LC) comprises the amino acid sequences of SEQ ID NOs: 119 and 6;

i) an antibody whose H-CDR1-3 and L-CDR1-3 comprise the amino acid sequences of SEQ ID NOs: 120-125, respectively;

j) an antibody whose VH is at least 90% identical in sequence to the amino acid sequence of SEQ ID NO: 118 and whose VL is at least 90% identical in sequence to the amino acid sequence of SEQ ID NO: 119;

k) an antibody whose VH comprises the amino acid sequence of SEQ ID NO: 118 and whose VL comprises the amino acid sequence of SEQ ID NO: 119; and l) an antibody whose HC comprises the amino acid sequence of SEQ ID NO: 118 and the amino acid sequence of SEQ ID NO: 5, 23, 24, or 25; and whose LC comprises the amino acid sequences of SEQ ID NOs: 119 and 6.

In some embodiments, the anti-TIM-3 antibody is selected from the group consisting of:

a) an antibody whose H-CDR1-3 comprise the amino acid sequences of SEQ ID NOs: 130-132, respectively;

b) an antibody whose heavy chain variable domain (VH) is at least 90% identical in sequence to the amino acid sequence of SEQ ID NO: 128;

c) an antibody whose VH comprises the amino acid sequence of SEQ ID NO: 128;

d) an antibody whose heavy chain (HC) comprises the amino acid sequences of SEQ ID NO: 128 and SEQ ID NO: 5, 23, 24, or 25;

e) an antibody whose L-CDR1-3 comprise the amino acid sequences of SEQ ID NOs: 133-135, respectively;

f) an antibody whose light chain variable domain (VL) is at least 90% identical in sequence to the amino acid sequence of SEQ ID NO: 129;

g) an antibody whose VL comprises the amino acid sequence of SEQ ID NO: 129;

h) an antibody whose light chain (LC) comprises the amino acid sequences of SEQ ID NOs: 129 and 6;

i) an antibody whose H-CDR1-3 and L-CDR1-3 comprise the amino acid sequences of SEQ ID NOs: 130-135, respectively;

j) an antibody whose VH is at least 90% identical in sequence to the amino acid sequence of SEQ ID NO: 128 and whose VL is at least 90% identical in sequence to the amino acid sequence of SEQ ID NO: 129;

k) an antibody whose VH comprises the amino acid sequence of SEQ ID NO: 128 and whose VL comprises the amino acid sequence of SEQ ID NO: 129; and l) an antibody whose HC comprises the amino acid sequence of SEQ ID NO: 128 and the amino acid sequence of SEQ ID NO: 5, 23, 24, or 25; and whose LC comprises the amino acid sequences of SEQ ID NOs: 129 and 6.

In some embodiments, the anti-TIM-3 antibody is selected from the group consisting of:

a) an antibody whose H-CDR1-3 comprise the amino acid sequences of SEQ ID NOs: 140-142, respectively;

b) an antibody whose heavy chain variable domain (VH) is at least 90% identical in sequence to the amino acid sequence of SEQ ID NO: 138;

c) an antibody whose VH comprises the amino acid sequence of SEQ ID NO: 138;

d) an antibody whose heavy chain (HC) comprises the amino acid sequences of SEQ ID NO: 138 and SEQ ID NO: 5, 23, 24, or 25;

e) an antibody whose L-CDR1-3 comprise the amino acid sequences of SEQ ID NOs: 143-145, respectively;

f) an antibody whose light chain variable domain (VL) is at least 90% identical in sequence to the amino acid sequence of SEQ ID NO: 139;

g) an antibody whose VL comprises the amino acid sequence of SEQ ID NO: 139;

h) an antibody whose light chain (LC) comprises the amino acid sequences of SEQ ID NOs: 139 and 6;

i) an antibody whose H-CDR1-3 and L-CDR1-3 comprise the amino acid sequences of SEQ ID NOs: 140-145, respectively;

j) an antibody whose VH is at least 90% identical in sequence to the amino acid sequence of SEQ ID NO: 138 and whose VL is at least 90% identical in sequence to the amino acid sequence of SEQ ID NO: 139;

k) an antibody whose VH comprises the amino acid sequence of SEQ ID NO: 138 and whose VL comprises the amino acid sequence of SEQ ID NO: 139; and l) an antibody whose HC comprises the amino acid sequence of SEQ ID NO: 138 and the amino acid sequence of SEQ ID NO: 5, 23, 24, or 25; and whose LC comprises the amino acid sequences of SEQ ID NOs: 139 and 6.

In some embodiments, the anti-TIM-3 antibody is selected from the group consisting of:

a) an antibody whose H-CDR1-3 comprise the amino acid sequences of SEQ ID NOs: 150-152, respectively;

b) an antibody whose heavy chain variable domain (VH) is at least 90% identical in sequence to the amino acid sequence of SEQ ID NO: 148;

c) an antibody whose VH comprises the amino acid sequence of SEQ ID NO: 148;

d) an antibody whose heavy chain (HC) comprises the amino acid sequences of SEQ ID NO: 148 and SEQ ID NO: 5, 23, 24, or 25;

e) an antibody whose L-CDR1-3 comprise the amino acid sequences of SEQ ID NOs: 153-155, respectively;

f) an antibody whose light chain variable domain (VL) is at least 90% identical in sequence to the amino acid sequence of SEQ ID NO: 149;

g) an antibody whose VL comprises the amino acid sequence of SEQ ID NO: 149;

h) an antibody whose light chain (LC) comprises the amino acid sequences of SEQ ID NOs: 149 and 6;

i) an antibody whose H-CDR1-3 and L-CDR1-3 comprise the amino acid sequences of SEQ ID NOs: 150-155, respectively;

j) an antibody whose VH is at least 90% identical in sequence to the amino acid sequence of SEQ ID NO: 148 and whose VL is at least 90% identical in sequence to the amino acid sequence of SEQ ID NO: 149;

k) an antibody whose VH comprises the amino acid sequence of SEQ ID NO: 148 and whose VL comprises the amino acid sequence of SEQ ID NO: 149; and l) an antibody whose HC comprises the amino acid sequence of SEQ ID NO: 148 and the amino acid sequence of SEQ ID NO: 5, 23, 24, or 25; and whose LC comprises the amino acid sequences of SEQ ID NOs: 149 and 6.

In some embodiments, the anti-TIM-3 antibody is selected from the group consisting of:

a) an antibody whose H-CDR1-3 comprise the amino acid sequences of SEQ ID NOs: 160-162, respectively;

b) an antibody whose heavy chain variable domain (VH) is at least 90% identical in sequence to the amino acid sequence of SEQ ID NO: 158;

c) an antibody whose VH comprises the amino acid sequence of SEQ ID NO: 158;

d) an antibody whose heavy chain (HC) comprises the amino acid sequences of SEQ ID NO: 158 and SEQ ID NO: 5, 23, 24, or 25;

e) an antibody whose L-CDR1-3 comprise the amino acid sequences of SEQ ID NOs: 163-165, respectively;

f) an antibody whose light chain variable domain (VL) is at least 90% identical in sequence to the amino acid sequence of SEQ ID NO: 159;

g) an antibody whose VL comprises the amino acid sequence of SEQ ID NO: 159;

h) an antibody whose light chain (LC) comprises the amino acid sequences of SEQ ID NOs: 159 and 6;

i) an antibody whose H-CDR1-3 and L-CDR1-3 comprise the amino acid sequences of SEQ ID NOs: 160-165, respectively;

j) an antibody whose VH is at least 90% identical in sequence to the amino acid sequence of SEQ ID NO: 158 and whose VL is at least 90% identical in sequence to the amino acid sequence of SEQ ID NO: 159;

k) an antibody whose VH comprises the amino acid sequence of SEQ ID NO: 158 and whose VL comprises the amino acid sequence of SEQ ID NO: 159; and l) an antibody whose HC comprises the amino acid sequence of SEQ ID NO: 158 and the amino acid sequence of SEQ ID NO: 5, 23, 24, or 25; and whose LC comprises the amino acid sequences of SEQ ID NOs: 159 and 6.

In some embodiments, the anti-TIM-3 antibody is selected from the group consisting of:

a) an antibody whose H-CDR1-3 comprise the amino acid sequences of SEQ ID NOs: 170-172, respectively;

b) an antibody whose heavy chain variable domain (VH) is at least 90% identical in sequence to the amino acid sequence of SEQ ID NO: 168;

c) an antibody whose VH comprises the amino acid sequence of SEQ ID NO: 168;

d) an antibody whose heavy chain (HC) comprises the amino acid sequences of SEQ ID NO: 168 and SEQ ID NO: 5, 23, 24, or 25;

e) an antibody whose L-CDR1-3 comprise the amino acid sequences of SEQ ID NOs: 173-175, respectively;

f) an antibody whose light chain variable domain (VL) is at least 90% identical in sequence to the amino acid sequence of SEQ ID NO: 169;

g) an antibody whose VL comprises the amino acid sequence of SEQ ID NO: 169;

h) an antibody whose light chain (LC) comprises the amino acid sequences of SEQ ID NOs: 169 and 6;

i) an antibody whose H-CDR1-3 and L-CDR1-3 comprise the amino acid sequences of SEQ ID NOs: 170-175, respectively;

j) an antibody whose VH is at least 90% identical in sequence to the amino acid sequence of SEQ ID NO: 168 and whose VL is at least 90% identical in sequence to the amino acid sequence of SEQ ID NO: 169;

k) an antibody whose VH comprises the amino acid sequence of SEQ ID NO: 168 and whose VL comprises the amino acid sequence of SEQ ID NO: 169; and l) an antibody whose HC comprises the amino acid sequence of SEQ ID NO: 168 and the amino acid sequence of SEQ ID NO: 5, 23, 24, or 25; and whose LC comprises the amino acid sequences of SEQ ID NOs: 169 and 6.

In some embodiments, the anti-TIM-3 antibody is selected from the group consisting of:

a) an antibody whose H-CDR1-3 comprise the amino acid sequences of SEQ ID NOs: 180-182, respectively;

b) an antibody whose heavy chain variable domain (VH) is at least 90% identical in sequence to the amino acid sequence of SEQ ID NO: 178;

c) an antibody whose VH comprises the amino acid sequence of SEQ ID NO: 178;

d) an antibody whose heavy chain (HC) comprises the amino acid sequences of SEQ ID NO: 178 and SEQ ID NO: 5, 23, 24, or 25;

e) an antibody whose L-CDR1-3 comprise the amino acid sequences of SEQ ID NOs: 183-185, respectively;

f) an antibody whose light chain variable domain (VL) is at least 90% identical in sequence to the amino acid sequence of SEQ ID NO: 179;

g) an antibody whose VL comprises the amino acid sequence of SEQ ID NO: 179;

h) an antibody whose light chain (LC) comprises the amino acid sequences of SEQ ID NOs: 179 and 6;

i) an antibody whose H-CDR1-3 and L-CDR1-3 comprise the amino acid sequences of SEQ ID NOs: 180-185, respectively;

j) an antibody whose VH is at least 90% identical in sequence to the amino acid sequence of SEQ ID NO: 178 and whose VL is at least 90% identical in sequence to the amino acid sequence of SEQ ID NO: 179;

k) an antibody whose VH comprises the amino acid sequence of SEQ ID NO: 178 and whose VL comprises the amino acid sequence of SEQ ID NO: 179; and l) an antibody whose HC comprises the amino acid sequence of SEQ ID NO: 178 and the amino acid sequence of SEQ ID NO: 5, 23, 24, or 25; and whose LC comprises the amino acid sequences of SEQ ID NOs: 179 and 6.

In some embodiments, the anti-TIM-3 antibody is selected from the group consisting of:

a) an antibody whose H-CDR1-3 comprise the amino acid sequences of SEQ ID NOs: 190-192, respectively;

b) an antibody whose heavy chain variable domain (VH) is at least 90% identical in sequence to the amino acid sequence of SEQ ID NO: 188;

c) an antibody whose VH comprises the amino acid sequence of SEQ ID NO: 188;

d) an antibody whose heavy chain (HC) comprises the amino acid sequences of SEQ ID NO: 188 and SEQ ID NO: 5, 23, 24, or 25;

e) an antibody whose L-CDR1-3 comprise the amino acid sequences of SEQ ID NOs: 193-195, respectively;

f) an antibody whose light chain variable domain (VL) is at least 90% identical in sequence to the amino acid sequence of SEQ ID NO: 189;

g) an antibody whose VL comprises the amino acid sequence of SEQ ID NO: 189;

h) an antibody whose light chain (LC) comprises the amino acid sequences of SEQ ID NOs: 189 and 6;

i) an antibody whose H-CDR1-3 and L-CDR1-3 comprise the amino acid sequences of SEQ ID NOs: 190-195, respectively;

j) an antibody whose VH is at least 90% identical in sequence to the amino acid sequence of SEQ ID NO: 188 and whose VL is at least 90% identical in sequence to the amino acid sequence of SEQ ID NO: 189;

k) an antibody whose VH comprises the amino acid sequence of SEQ ID NO: 188 and whose VL comprises the amino acid sequence of SEQ ID NO: 189; and l) an antibody whose HC comprises the amino acid sequence of SEQ ID NO: 188 and the amino acid sequence of SEQ ID NO: 5, 23, 24, or 25; and whose LC comprises the amino acid sequences of SEQ ID NOs: 189 and 6.

In some embodiments, the anti-TIM-3 antibody is selected from the group consisting of:

a) an antibody whose H-CDR1-3 comprise the amino acid sequences of SEQ ID NOs: 200-202, respectively;

b) an antibody whose heavy chain variable domain (VH) is at least 90% identical in sequence to the amino acid sequence of SEQ ID NO: 198;

c) an antibody whose VH comprises the amino acid sequence of SEQ ID NO: 198;

d) an antibody whose heavy chain (HC) comprises the amino acid sequences of SEQ ID NO: 198 and SEQ ID NO: 5, 23, 24, or 25;

e) an antibody whose L-CDR1-3 comprise the amino acid sequences of SEQ ID NOs: 203-205, respectively;

f) an antibody whose light chain variable domain (VL) is at least 90% identical in sequence to the amino acid sequence of SEQ ID NO: 199;

g) an antibody whose VL comprises the amino acid sequence of SEQ ID NO: 199;

h) an antibody whose light chain (LC) comprises the amino acid sequences of SEQ ID NOs: 199 and 6;

i) an antibody whose H-CDR1-3 and L-CDR1-3 comprise the amino acid sequences of SEQ ID NOs: 200-205, respectively;

j) an antibody whose VH is at least 90% identical in sequence to the amino acid sequence of SEQ ID NO: 198 and whose VL is at least 90% identical in sequence to the amino acid sequence of SEQ ID NO: 199;

k) an antibody whose VH comprises the amino acid sequence of SEQ ID NO: 198 and whose VL comprises the amino acid sequence of SEQ ID NO: 199; and l) an antibody whose HC comprises the amino acid sequence of SEQ ID NO: 198 and the amino acid sequence of SEQ ID NO: 5, 23, 24, or 25; and whose LC comprises the amino acid sequences of SEQ ID NOs: 199 and 6.

In some embodiments, the anti-TIM-3 antibody is selected from the group consisting of:

a) an antibody whose H-CDR1-3 comprise the amino acid sequences of SEQ ID NOs: 210-212, respectively;

b) an antibody whose heavy chain variable domain (VH) is at least 90% identical in sequence to the amino acid sequence of SEQ ID NO: 208;

c) an antibody whose VH comprises the amino acid sequence of SEQ ID NO: 208;

d) an antibody whose heavy chain (HC) comprises the amino acid sequences of SEQ ID NO: 208 and SEQ ID NO: 5, 23, 24, or 25;

e) an antibody whose L-CDR1-3 comprise the amino acid sequences of SEQ ID NOs: 213-215, respectively;

f) an antibody whose light chain variable domain (VL) is at least 90% identical in sequence to the amino acid sequence of SEQ ID NO: 209;

g) an antibody whose VL comprises the amino acid sequence of SEQ ID NO: 209;

h) an antibody whose light chain (LC) comprises the amino acid sequences of SEQ ID NOs: 209 and 6;

i) an antibody whose H-CDR1-3 and L-CDR1-3 comprise the amino acid sequences of SEQ ID NOs: 210-215, respectively;

j) an antibody whose VH is at least 90% identical in sequence to the amino acid sequence of SEQ ID NO: 208 and whose VL is at least 90% identical in sequence to the amino acid sequence of SEQ ID NO: 209;

k) an antibody whose VH comprises the amino acid sequence of SEQ ID NO: 208 and whose VL comprises the amino acid sequence of SEQ ID NO: 209; and l) an antibody whose HC comprises the amino acid sequence of SEQ ID NO: 208 and the amino acid sequence of SEQ ID NO: 5, 23, 24, or 25; and whose LC comprises the amino acid sequences of SEQ ID NOs: 209 and 6.

In some embodiments, the anti-TIM-3 antibody is selected from the group a) an antibody whose H-CDR1-3 comprise the amino acid sequences of SEQ ID NOs: 220-222, respectively;

b) an antibody whose heavy chain variable domain (VH) is at least 90% identical in sequence to the amino acid sequence of SEQ ID NO: 218;

c) an antibody whose VH comprises the amino acid sequence of SEQ ID NO: 218;

d) an antibody whose heavy chain (HC) comprises the amino acid sequences of SEQ ID NO: 218 and SEQ ID NO: 5, 23, 24, or 25;

e) an antibody whose L-CDR1-3 comprise the amino acid sequences of SEQ ID NOs: 223-225, respectively;

f) an antibody whose light chain variable domain (VL) is at least 90% identical in sequence to the amino acid sequence of SEQ ID NO: 219;

g) an antibody whose VL comprises the amino acid sequence of SEQ ID NO: 219;

h) an antibody whose light chain (LC) comprises the amino acid sequences of SEQ ID NOs: 219 and 6;

i) an antibody whose H-CDR1-3 and L-CDR1-3 comprise the amino acid sequences of SEQ ID NOs: 220-225, respectively;

j) an antibody whose VH is at least 90% identical in sequence to the amino acid sequence of SEQ ID NO: 218 and whose VL is at least 90% identical in sequence to the amino acid sequence of SEQ ID NO: 219;

k) an antibody whose VH comprises the amino acid sequence of SEQ ID NO: 218 and whose VL comprises the amino acid sequence of SEQ ID NO: 219; and l) an antibody whose HC comprises the amino acid sequence of SEQ ID NO: 218 and the amino acid sequence of SEQ ID NO: 5, 23, 24, or 25; and whose LC comprises the amino acid sequences of SEQ ID NOs: 219 and 6.

In some embodiments, the anti-TIM-3 antibody is selected from the group consisting of:

a) an antibody whose H-CDR1-3 comprise the amino acid sequences of SEQ ID NOs: 230-232, respectively;

b) an antibody whose heavy chain variable domain (VH) is at least 90% identical in sequence to the amino acid sequence of SEQ ID NO: 228;

c) an antibody whose VH comprises the amino acid sequence of SEQ ID NO: 228;

d) an antibody whose heavy chain (HC) comprises the amino acid sequences of SEQ ID NO: 228 and SEQ ID NO: 5, 23, 24, or 25;

e) an antibody whose L-CDR1-3 comprise the amino acid sequences of SEQ ID NOs: 233-235, respectively;

f) an antibody whose light chain variable domain (VL) is at least 90% identical in sequence to the amino acid sequence of SEQ ID NO: 229;

g) an antibody whose VL comprises the amino acid sequence of SEQ ID NO: 229;

h) an antibody whose light chain (LC) comprises the amino acid sequences of SEQ ID NOs: 229 and 6;

i) an antibody whose H-CDR1-3 and L-CDR1-3 comprise the amino acid sequences of SEQ ID NOs: 230-235, respectively;

j) an antibody whose VH is at least 90% identical in sequence to the amino acid sequence of SEQ ID NO: 228 and whose VL is at least 90% identical in sequence to the amino acid sequence of SEQ ID NO: 229;

k) an antibody whose VH comprises the amino acid sequence of SEQ ID NO: 228 and whose VL comprises the amino acid sequence of SEQ ID NO: 229; and l) an antibody whose HC comprises the amino acid sequence of SEQ ID NO: 228 and the amino acid sequence of SEQ ID NO: 5, 23, 24, or 25; and whose LC comprises the amino acid sequences of SEQ ID NOs: 229 and 6.

In some embodiments, the anti-TIM-3 antibody, or an antigen-binding portion thereof, competes for binding to human TIM-3 with, or binds to the same epitope of human TIM-3 as, antibody 15086.15086 having the IgG1 format, antibody 15086.16837 having the IgG1 LALA format, antibody 15086.17145 having the IgG2 format, or antibody 15086.17144 having the IgG4 format. In some embodiments, the antibody of the invention is an IgG. In some embodiments, the antibody of the invention has an IgG1, IgG2, IgG3, or IgG4 format.

In some embodiments, the anti-TIM-3 antibody, or an antigen-binding portion thereof, competes for binding to human TIM-3 with, or binds to the same epitope of human TIM-3 as, antibody 20131, 20293, 15105, 15107, 15109, 15174, 15175, 15260, 15284, 15299, 15353, 15354, 17244, 17245, 19324, 19416, 19568, 20185, 20300, 20362, or 20621. In some embodiments, the antibody of the invention has an IgG1, IgG2, IgG3, or IgG4 format.

In some embodiments, an anti-TIM-3 antibody of the invention, or an antigen-binding portion thereof, does not compete for binding to human TIM-3 with, or bind to the same epitope of human TIM-3 as, any or all of the antibodies from epitope bin 1 (reference antibody mAb 15), bin 2 (e.g., antibodies 15105 and 15107), and bin 8 (e.g., antibodies 15174 and 15175) as defined in Example 12 below.

In some embodiments, an anti-TIM-3 antibody of the invention, or an antigen-binding portion thereof, does not compete for binding to human TIM-3 with, or bind to the same epitope of human TIM-3 as, any or all of the antibodies from epitope bin 2 (e.g., antibodies 15105 and 15107) and bin 8 (e.g., antibodies 15174 and 15175) as defined in Example 12 below.

In some embodiments, an anti-TIM-3 antibody of the invention, or an antigen-binding portion thereof, does not compete for binding to human TIM-3 with, or bind to the same epitope of human TIM-3 as, any or all of the antibodies from epitope bin 2 (e.g., antibodies 15105 and 15107) as defined in Example 12 below.

In some embodiments, the anti-TIM-3 antibody competes for binding to human TIM-3 or binds to the same epitope of human TIM-3 as an antibody whose heavy chain (H) CDR1-3 and light chain (L) CDR1-3 comprise, respectively, SEQ ID NOs: 7-12, 30-35, 40-45, 50-55, 60-65, 70-75, 80-85, 90-95, 100-105, 110-115, 120-125, 130-135, 140-145, 150-155, 160-165, 170-175, 180-185, 190-195, 200-205, 210-215, 220-225, or 230-235.

In some embodiments, the anti-TIM-3 antibody or antigen-binding portion has a heavy chain variable domain (VH) that is at least 90% identical in sequence to SEQ ID NO: 3, 15, 28, 38, 48, 58, 68, 78, 88, 98, 108, 118, 128, 138, 148, 158, 168, 178, 188, 198, 208, 218, or 228, e.g., at least 95% identical, such as at least 96%, at least 97%, at least 98% or at least 99% identical to said sequence.

In some embodiments, the anti-TIM-3 antibody has a heavy chain variable domain (VH) that is at least 90% identical in sequence to SEQ ID NO: 3, 28, 38, 48, 58, 68, 78, 88, 98, 108, 118, 128, 138, 148, 158, 168, 178, 188, 198, 208, 218, or 228, e.g. at least 95% identical, such as at least 96%, at least 97%, at least 98% or at least 99% identical to said sequence; and a heavy chain constant region (CH) that is at least 90% identical in sequence to SEQ ID NO: 5, e.g. at least 95% identical, such as at least 96%, at least 97%, at least 98% or at least 99% identical to SEQ ID NO: 5.

In some embodiments, the anti-TIM-3 antibody has a heavy chain (HC) that comprises the VH amino acid sequence of SEQ ID NO: 3, 28, 38, 48, 58, 68, 78, 88, 98, 108, 118, 128, 138, 148, 158, 168, 178, 188, 198, 208, 218, or 228 and the CH amino acid sequence of SEQ ID NO: 5.

In some embodiments, the anti-TIM-3 antibody has a heavy chain variable domain (VH) that is at least 90% identical in sequence to SEQ ID NO: 15, 28, 38, 48, 58, 68, 78, 88, 98, 108, 118, 128, 138, 148, 158, 168, 178, 188, 198, 208, 218, or 228, e.g. at least 95% identical, such as at least 96%, at least 97%, at least 98% or at least 99% identical to said sequence; and a heavy chain constant region (CH) that is at least 90% identical in sequence to SEQ ID NO: 23, 24 or 25, e.g. at least 95% identical, such as at least 96%, at least 97%, at least 98% or at least 99% identical to SEQ ID NO: 23, 24 or 25. In particular embodiments, the CH is at least 90% identical in sequence to SEQ ID NO: 25, e.g. at least 95% identical, such as at least 96%, at least 97%, at least 98% or at least 99% identical to SEQ ID NO: 25

In some embodiments, the anti-TIM-3 antibody has a heavy chain (HC) that comprises the VH amino acid sequence of SEQ ID NO: 15, 28, 38, 48, 58, 68, 78, 88, 98, 108, 118, 128, 138, 148, 158, 168, 178, 188, 198, 208, 218, or 228 and the CH amino acid sequence of SEQ ID NO: 23, 24 or 25. In particular embodiments, the heavy chain comprises the CH amino acid sequence of SEQ ID NO: 25.

In some embodiments, the anti-TIM-3 antibody has a light chain variable domain (VL) that is at least 90% identical in sequence to the VL amino acid sequence of SEQ ID NO: 4, 29, 39, 49, 59, 69, 79, 89, 99, 109, 119, 129, 139, 149, 159, 169, 179, 189, 199, 209, 219, or 229, e.g. at least 95% identical, such as at least 96%, at least 97%, at least 98% or at least 99% identical to said sequence.

In some embodiments, the anti-TIM-3 antibody has a light chain variable domain (VL) that is at least 90% identical in sequence to the VL amino acid sequence of SEQ ID NO: 4, 29, 39, 49, 59, 69, 79, 89, 99, 109, 119, 129, 139, 149, 159, 169, 179, 189, 199, 209, 219, or 229, e.g. at least 95% identical, such as at least 96%, at least 97%, at least 98% or at least 99% identical to said sequence; and a light chain constant region (CL) that is at least 90% identical in sequence to SEQ ID NO: 6, e.g. at least 95% identical, such as at least 96%, at least 97%, at least 98% or at least 99% identical to SEQ ID NO: 6.

In some embodiments, the anti-TIM-3 antibody has a light chain (LC) that comprises the VL amino acid sequence of SEQ ID NO: 4, 29, 39, 49, 59, 69, 79, 89, 99, 109, 119, 129, 139, 149, 159, 169, 179, 189, 199, 209, 219, or 229 and the CL amino acid sequence of SEQ ID NO: 6.

In certain embodiments, the anti-TIM-3 antibody comprises any one of the above-described heavy chains and any one of the above-described light chains.

In some embodiments, any of the anti-TIM-3 antibodies or antigen-binding portions described herein may inhibit binding of ligands such as galectin-9, CEACAM1, HMGB-1, and phosphatidylserine to TIM-3.

In one embodiment, administration of an anti-TIM-3 antibody of the invention or an antigen-binding portion thereof may activate dendritic cells, causing their maturation and thereby their ability to stimulate T-cells. While not wishing to be bound by any particular theory, it is believed that the anti-TIM-3 antibodies of the invention function as TIM-3 dendritic cell activators, whereby their effect on dendritic cells serves to stimulate T cells. In a tumor-related setting, the anti-TIM-3 antibodies thus would cause maturation and activation of tumor associated dendritic cells, resulting in activation of tumor specific T-cells.

In some embodiments, any of the anti-TIM-3 antibodies or antigen-binding portions described herein may bind to human TIM-3 with a $K_D$ of at least 100, at least 50, at least 40, at least 30, at least 25, at least 20, at least 15, at least 10, at least 9, at least 8, at least 7, or at least 6 nM. In certain embodiments, the $K_D$ is determined using surface plasmon resonance.

In some embodiments, any of the anti-TIM-3 antibodies or antigen-binding portions described herein may bind to cynomolgus TIM-3 with a $K_D$ of at least 100, at least 50, at least 40, at least 30, at least 25, at least 24, at least 23, at least 22, at least 21, or at least 20 nM. In certain embodiments, the $K_D$ is determined using surface plasmon resonance.

In some embodiments, any of the anti-TIM-3 antibodies or antigen-binding portions described herein may have an avidity for human TIM-3 of EC50≤2, 1.5, 1, 0.5, 0.4, 0.3, 0.2, or 0.15 nM. In some embodiments, any of the anti-TIM-3 antibodies or antigen-binding portions described herein may have an avidity for cynomolgus TIM-3 of EC50≤80, 70, 60, 50, 40, 30, 25, 20, 15, 10, 5, 4, 3, 2, 1.5, 1, 0.5, 0.4, 0.3, 0.2, or 0.15 nM.

In one embodiment, administration of an anti-TIM-3 antibody of the invention or an antigen-binding portion thereof may directly activate T cells.

In some embodiments, an anti-TIM-3 antibody of the invention, or an antigen-binding portion thereof, binds to an epitope of TIM-3 that includes at least one (e.g., at least one, at least two, at least three, at least four, at least five, at least six, at least seven, at least eight, or at least nine) of the following residues of SEQ ID NO: 236: P50, V60, F61, E62, G64, R69, I117, M118, and D120. An epitope with any combination of the above residues is contemplated.

In some embodiments, an anti-TIM-3 antibody of the invention, or an antigen-binding portion thereof, binds to an epitope of TIM-3 that comprises residues 62-67 and/or 114-117 of SEQ ID NO: 236. In some embodiments, the antibody or portion binds to residues 62-67 (or a fragment thereof, such as a one, two, three, four, or five residue fragment), of SEQ ID NO: 236 (e.g., antibodies 15086.15086, 15086.16837, 15086.17145, 15086.17144, and 20293). In some embodiments, the antibody or portion binds to residues 114-117 (or a fragment thereof, such as a one, two, or three residue fragment) of SEQ ID NO: 236 (e.g., antibody 20131). An epitope with any combination of the above residues is also contemplated.

The class of an anti-TIM-3 antibody obtained by the methods described herein may be changed or switched with another class or subclass. In one aspect of the invention, a nucleic acid molecule encoding VL or VH is isolated using methods well-known in the art such that it does not include nucleic acid sequences encoding CL or CH. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH chain, as described above. For example, an anti-TIM-3 antibody that was originally IgM may be class switched to IgG. Further, the class switching may be used to convert one IgG subclass to another, e.g., from IgG1 to IgG2. A κ light chain constant region can be changed to a λ light chain constant region. A preferred method for producing an antibody of the invention with a desired Ig isotype comprises the steps of isolating a nucleic acid molecule encoding the heavy chain of an anti-TIM-3 antibody and a nucleic acid molecule encoding the light chain of an anti-TIM-3 antibody, obtaining the variable domain of the heavy chain, ligating the variable domain of the heavy chain with the constant region of a heavy chain of the desired isotype, expressing the light chain and the ligated heavy chain in a cell, and collecting the anti-TIM-3 antibody with the desired isotype.

The anti-TIM-3 antibody of the invention can be an IgG, an IgM, an IgE, an IgA, or an IgD molecule, but is typically of the IgG isotype, e.g. of IgG subclass IgG1, IgG2a or IgG2b, IgG3 or IgG4. In one embodiment, the antibody is an IgG1. In another embodiment, the antibody is an IgG2.

In one embodiment, the anti-TIM-3 antibody may comprise at least one mutation in the Fc region. A number of different Fc mutations are known, where these mutations provide altered effector function. For example, in many cases it will be desirable to reduce or eliminate effector function, e.g., where ligand/receptor interactions are undesired or in the case of antibody-drug conjugates. Fc region amino acid positions that may be advantageous to mutate in order to reduce effector function include one or more of positions 228, 233, 234 and 235, where amino acid positions are numbered according to the IMGT® numbering scheme.

In one embodiment, one or both of the amino acid residues at positions 234 and 235 may be mutated, for example, from Leu to Ala (L234A/L235A). These mutations reduce effector function of the Fc region of IgG1 antibodies. Additionally or alternatively, the amino acid residue at position 228 may be mutated, for example to Pro. In another embodiment, the amino acid residue at position 233 may be mutated, e.g., to Pro, the amino acid residue at position 234 may be mutated, e.g., to Val, and/or the amino acid residue at position 235 may be mutated, e.g., to Ala. The amino acid positions are numbered according to the IMGT® numbering scheme.

In another embodiment, where the antibody is of the IgG4 subclass, it may comprise the mutation S228P, i.e., having a proline in position 228, where the amino acid position is numbered according to the Eu IMGT® numbering scheme. This mutation is known to reduce undesired Fab arm exchange (Angal et al., *Mol Immunol.* 30:105-8 (1993)).

In certain embodiments, an antibody or antigen-binding portion thereof of the invention may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of an anti-TIM-3 antibody of the invention linked to another polypeptide. In certain embodiments, only the variable domains of the anti-TIM-3 antibody are linked to the polypeptide. In certain embodiments, the VH domain of an anti-TIM-3 antibody is linked to a first polypeptide, while the VL domain of an anti-TIM-3 antibody is linked to a second polypeptide that associates with the first polypeptide in a manner such that the VH and VL domains can interact with one another to form an antigen-binding site. In another preferred embodiment, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody (scFv), the VH- and VL-encoding DNA fragments are operatively linked to another fragment encoding a flexible linker, e.g., encoding the amino acid sequence (Gly4-Ser)3 (SEQ ID NO: 240), such that the VH and VL sequences can be expressed as a contiguous single-chain protein, with the VL and VH domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used. Bispecific or polyvalent antibodies may be generated that bind specifically to human TIM-3 and to another molecule, for instance.

In other embodiments, other modified antibodies may be prepared using anti-TIM-3 antibody-encoding nucleic acid molecules. For instance, "kappa bodies" (Ill et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

An anti-TIM-3 antibody or antigen-binding portion of the invention can be derivatized or linked to another molecule (e.g., another peptide or protein). In general, the antibodies or portions thereof are derivatized such that TIM-3 binding is not affected adversely by the derivatization or labeling. Accordingly, the antibodies and antibody portions of the invention are intended to include both intact and modified forms of the human anti-TIM-3 antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, Il.

An anti-TIM-3 antibody can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody according to the present invention may also be labeled. As used herein, the terms "label" or "labeled" refer to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the antibodies of the invention may be present in a neutral form (including zwitter ionic forms) or as a positively or negatively-charged species. In some embodiments, the antibodies may be complexed with a counterion to form a pharmaceutically acceptable salt. The term "pharmaceutically acceptable salt" refers to a complex comprising one or more antibodies and one or more counterions, wherein the counterions are derived from pharmaceutically acceptable inorganic and organic acids and bases.

Bispecific Binding Molecules

In a further aspect, the invention provides a bispecific binding molecule having the binding specificity of an anti-TIM-3 antibody described herein and the binding specificity of another anti-TIM-3 antibody (e.g., another anti-TIM-3 antibody described herein) or an antibody that targets a different protein, such as another immune checkpoint protein, a cancer antigen, or another cell surface molecule whose activity mediates a disease condition such as cancer. Such bispecific binding molecules are known in the art, and examples of different types of bispecific binding molecules are given elsewhere herein.

Nucleic Acid Molecules and Vectors

The present invention also provides nucleic acid molecules and sequences encoding anti-TIM-3 antibodies or antigen-binding portions thereof described herein. In some embodiments, different nucleic acid molecules encode the heavy chain and light chain amino acid sequences of the anti-TIM-3 antibody or an antigen-binding portion thereof. In other embodiments, the same nucleic acid molecule encodes the heavy chain and light chain amino acid sequences of the anti-TIM-3 antibody or an antigen-binding portion thereof.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single and double stranded forms.

The invention also provides nucleotide sequences that are at least 70%, 75%, 80%, 85%, 90%, 95%, 97%, 98% or 99% identical to one or more nucleotide sequences recited herein, e.g., to a nucleotide sequence encoding an amino acid sequence selected from the group consisting of SEQ ID NOs: 3, 4, 7-12, 15, 28-35, 38-45, 48-55, 58-65, 68-75, 78-85, 88-95, 98-105, 108-115, 118-125, 128-135, 138-145, 148-155, 158-165, 168-175, 178-185, 188-195, 198-205, 208-215, 218-225, and 228-235. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wisconsin FASTA, which includes, e.g., the programs FASTA2 and FASTA3, provides alignments and percent sequence identity of the regions of the best overlap between the query and search sequences (see, e.g., Pearson, *Methods Enzymol.* 183:63-98 (1990); Pearson, *Methods Mol. Biol.* 132:185-219 (2000); Pearson, *Methods Enzymol.* 266:227-258 (1996); and Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In one aspect, the invention provides a nucleic acid molecule comprising a nucleotide sequence selected from the group consisting of SEQ ID NOs: 1, 2, 13, 14, 26, 27, 36, 37, 46, 47, 56, 57, 66, 67, 76, 77, 86, 87, 96, 97, 106, 107, 116, 117, 126, 127, 136, 137, 146, 147, 156, 157, 166, 167, 176, 177, 186, 187, 196, 197, 206, 207, 216, 217, 226, and 227. The invention also provides nucleic acid molecules comprising nucleotide sequences that are at least 70%, 75%, 80%, 85%, 90%, 95%, 97%, 98% or 99% identical to any of said nucleotide sequences.

In any of the above embodiments, the nucleic acid molecules may be isolated. A nucleic acid molecule encoding the heavy and/or light chain of an anti-TIM-3 antibody or antigen-binding portion thereof of the invention can be isolated from any source that produces such an antibody or portion. In various embodiments, the nucleic acid molecules are isolated from B cells that express an anti-TIM-3 antibody isolated from an animal immunized with a human TIM-3 antigen, or from an immortalized cell produced from such a B cell. Methods of isolating nucleic acids encoding an antibody are well-known in the art. mRNA may be isolated and used to produce cDNA for use in polymerase chain reaction (PCR) or cDNA cloning of antibody genes. In certain embodiments, a nucleic acid molecule of the invention can be synthesized rather than isolated.

In some embodiments, a nucleic acid molecule of the invention can comprise a nucleotide sequence encoding a VH domain from an anti-TIM-3 antibody or antigen-binding portion of the invention joined in-frame to a nucleotide sequence encoding a heavy chain constant region from any source. Similarly, a nucleic acid molecule of the invention can comprise a nucleotide sequence encoding a VL domain from an anti-TIM-3 antibody or antigen-binding portion of the invention joined in-frame to a nucleotide sequence encoding a light chain constant region from any source.

In a further aspect of the invention, nucleic acid molecules encoding the variable domain of the heavy (VH) and/or light (VL) chains may be "converted" to full-length antibody genes. In one embodiment, nucleic acid molecules encoding the VH or VL domains are converted to full-length antibody genes by insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domains to a nucleic acid molecule encoding a CH and/or CL domain using standard molecular biological techniques. Nucleic acid molecules encoding the full-length heavy and/or light chains may then be expressed from a cell into which they have been introduced and the anti-TIM-3 antibody isolated.

The nucleic acid molecules may be used to recombinantly express large quantities of anti-TIM-3 antibodies. The nucleic acid molecules also may be used to produce, e.g., chimeric antibodies, bispecific antibodies, single chain antibodies, immunoadhesins, diabodies, mutated antibodies and antibody derivatives, as described herein.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-TIM-3 antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of the anti-TIM-3 antibodies or antigen-binding portions thereof of the invention as described herein.

In another embodiment, the nucleic acid molecules and vectors may be used to make mutated anti-TIM-3 antibodies. The antibodies may be mutated in the variable domains of the heavy and/or light chains, e.g., to alter a binding property of the antibody. For example, a mutation may be made in one or more of the CDRs to increase or decrease the $K_D$ of the anti-TIM-3 antibody, to increase or decrease $k_{off}$, or to alter the binding specificity of the antibody. In another embodiment, one or more mutations are made at an amino acid residue that is known to be changed compared to the germline in a monoclonal antibody of the invention. The mutations may be made in a CDR or framework region of a variable domain, or in a constant region. In a preferred embodiment, the mutations are made in a variable domain. In some embodiments, one or more mutations are made at an amino acid residue that is known to be changed compared to the germline in a CDR or framework region of a variable domain of an antibody or antigen-binding portion thereof of the invention.

In another embodiment, the framework region(s) are mutated so that the resulting framework region(s) have the amino acid sequence of the corresponding germline gene. A mutation may be made in a framework region or constant region to increase the half-life of the anti-TIM-3 antibody. See, e.g., PCT Publication WO 00/09560. A mutation in a framework region or constant region also can be made to alter the immunogenicity of the antibody, and/or to provide a site for covalent or non-covalent binding to another molecule. According to the invention, a single antibody may have mutations in any one or more of the CDRs or framework regions of the variable domain or in the constant region.

In a further aspect, the present invention provides a vector suitable for expressing one or both of the chains of an anti-TIM-3 antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The invention provides vectors comprising nucleic acid molecules that encode the heavy chain of an anti-TIM-3 antibody of the invention or an antigen-binding portion thereof, the light chain of an anti-TIM-3 antibody of the invention or an antigen-binding portion thereof, or both the heavy and light chains of an anti-TIM-3 antibody of the invention or an antigen-binding portion thereof. The invention further provides vectors comprising nucleic acid molecules encoding fusion proteins, modified antibodies, antibody fragments, and probes thereof.

In some embodiments, the anti-TIM-3 antibodies of the invention or antigen-binding portions thereof are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody coding sequence may be ligated into a vector such that transcriptional and translational control sequences within the vector serve their intended function of regulating the transcription and translation of the antibody coding sequence. The expression vector and expression control sequences may be chosen to be compatible with the expression host cell used. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector, and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can easily be inserted and expressed, as described above. The HC- and LC-encoding genes in such vectors may contain intron sequences that will result in enhanced overall antibody protein yields by stabilizing the related mRNA. The intron sequences are flanked by splice donor and splice acceptor sites, which determine where RNA splicing will occur. Location of intron sequences can be either in variable or constant regions of the antibody chains, or in both variable and constant regions when multiple introns are used. Polyadenylation and transcription termination may occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Host Cells and Methods of Antibody and Antibody Composition Production

An additional aspect of the invention relates to methods for producing the antibody compositions and antibodies and antigen-binding portions thereof of the invention. One embodiment of this aspect of the invention relates to a method for producing an antibody as defined herein, comprising providing a recombinant host cell capable of expressing the antibody, cultivating said host cell under conditions suitable for expression of the antibody, and isolating the resulting antibody. Antibodies produced by such expression in such recombinant host cells are referred to herein as "recombinant antibodies." The invention also provides progeny cells of such host cells, and antibodies produced by same.

The term "recombinant host cell" (or simply "host cell"), as used herein, means a cell into which a recombinant expression vector has been introduced. The invention provides host cells that may comprise, e.g., a vector according to the invention described above. The invention also provides host cells that comprise, e.g., a nucleotide sequence encoding the heavy chain or an antigen-binding portion thereof, a nucleotide sequence encoding the light chain or an antigen-binding portion thereof, or both, of an anti-TIM-3 antibody or antigen-binding portion thereof of the invention. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-TIM-3 antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected by determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention or antigen-binding portions thereof from production cell lines can be enhanced using a number of known techniques. For example, the glutamine synthetase gene expression system (the GS system) is a common approach for enhancing expression under certain conditions. The GS system is discussed in whole or part in connection with EP Patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein are part of the instant invention, regardless of the glycosylation state of the antibodies, and more generally, regardless of the presence or absence of post-translational modification(s).

Pharmaceutical Compositions

Another aspect of the invention is a pharmaceutical composition comprising as an active ingredient (or as the sole active ingredient) an anti-TIM-3 antibody or antigen-binding portion thereof, bi-specific binding molecule, or anti-TIM-3 antibody composition of the invention. The pharmaceutical composition may comprise any anti-TIM-3 antibody composition, bi-specific binding molecule, or antibody or antigen-binding portion thereof as described herein. In some embodiments, the compositions are intended for amelioration, prevention, and/or treatment of a TIM-3-related disorder (e.g., a disorder characterized by overexpression or overactivity of TIM-3 or any of its ligands) and/or cancer. In some embodiments, the compositions are intended for activation of the immune system. In certain embodiments, the compositions are intended for amelioration, prevention, and/or treatment of cancer originating in tissues such as skin, lung, intestine, ovary, brain, prostate, kidney, soft tissues, the hematopoietic system, head and neck, liver, bladder, breast, stomach, uterus and pancreas.

Generally, the antibodies of the invention or antigen-binding portions thereof or bi-specific binding molecules of the invention, are suitable to be administered as a formulation in association with one or more pharmaceutically acceptable excipient(s), e.g., as described below.

Pharmaceutical compositions of the invention will comprise one or more anti-TIM-3 antibodies or binding portions, or bi-specific binding molecules, of the invention, e.g., one or two anti-TIM-3 antibodies or binding portions or bi-specific binding molecules. In one embodiment, the composition comprises a single anti-TIM-3 antibody of the invention or binding portion thereof.

In another embodiment, the pharmaceutical composition may comprise at least one anti-TIM-3 antibody or antigen-binding portion thereof, e.g., one anti-TIM-3 antibody or portion, or one bi-specific binding molecule, and one or more additional antibodies that target one or more relevant cell surface receptors, e.g., one or more cancer-relevant receptors.

The term "excipient" is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in *Remington's Pharmaceutical Sciences,* 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and antigen-binding portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, and intrasynovial injection or infusions; and kidney dialytic infusion techniques. Regional perfusion is also contemplated. Particular embodiments include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-TIM-3 antibody or antigen-binding portion thereof, bi-specific binding molecule, or anti-TIM-3 antibody composition in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin, and/or by using modified-release coatings (e.g., slow-release coatings).

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antibody of the invention per actuation and the actuation volume may for example vary from 1 µL to 100 µL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic Uses of Antibodies and Compositions of the Invention

In one aspect, the anti-TIM-3 antibodies and antigen-binding portions thereof, anti-TIM-3 compositions, and bi-specific binding molecules of the invention are used to enhance or activate the immune system in a human in need thereof. In some embodiments, the patient has a condition characterized by overexpression or overactivity of TIM-3 or any of its ligands. In some embodiments, the patient is immune-suppressed. In certain embodiments, the antibody or antigen-binding portion thereof, composition, or bi-specific binding molecule is for use in the treatment of cancer, e.g., cancers that originate in tissues such as skin, lung, intestine, ovary, brain, prostate, kidney, soft tissues, hematopoietic system, head and neck, liver, bladder, breast, stomach, uterus and pancreas, and any cancers or other conditions which rely on TIM-3 activity and/or in which the patient expresses or overexpresses galectin-9, phosphatidyl-serine, CEACAM-1 and/or HMGB-1. Cancers treated by the anti-TIM-3 antibodies, antigen-binding portions thereof, anti-TIM-3 antibody compositions, and/or bi-specific binding molecules of the invention may include, e.g., melanoma, non-small cell lung cancer, colorectal cancer, renal cell carcinoma, leukemia (e.g., acute myeloid leukemia), and solid tumors (e.g., advanced or metastatic solid tumors).

In some embodiments, cancers treated by the anti-TIM-3 antibodies, antigen-binding portions, anti-TIM-3 compositions, and/or bi-specific binding molecules of the invention may include, e.g., melanoma (e.g., advanced or metastatic melanoma), non-small cell lung cancer, head and neck squamous cell cancer, renal cell carcinoma, Hodgkin's lymphoma, non-Hodgkin's lymphoma, glioblastoma, glioma, squamous cell lung cancer, small-cell lung cancer, hepatocellular carcinoma, bladder cancer, upper urinary tract cancer, esophageal cancer, gastroesophageal junction cancer, gastric cancer, liver cancer, colon cancer, colorectal carcinoma, multiple myeloma, sarcomas, acute myeloid leukemia, chronic myeloid leukemia, myelodysplastic syndrome, nasopharyngeal cancer, chronic lymphocytic leukemia, acute lymphoblastic leukemia, small lymphocytic lymphoma, ovarian cancer, gastrointestinal cancer, primary peritoneal cancer, fallopian tube cancer, urothelial cancer, HTLV-associated T-cell leukemia/lymphoma, prostate cancer, genitourinary cancer, meningioma, adrenocortical cancer, gliosarcoma, fibrosarcoma, kidney cancer, breast cancer, pancreatic cancer, endometrial cancer, skin basal cell cancer, cancer of the appendix, biliary tract cancer, salivary gland cancer, advanced Merkel cell cancer, diffuse large B cell lymphoma, follicular lymphoma, mesothelioma, and solid tumors.

In some embodiments, the antibody or antigen-binding portion thereof, composition, or bi-specific binding molecule is for use in treating viral and/or parasitic infections, e.g., where the pathogens inhibit the host immune response.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic, for example, may result in tumor shrinkage, increased survival, elimination of cancer cells, decreased disease progression, reversal of metastasis, or other clinical endpoints desired by healthcare professionals.

The antibody compositions or antibodies or antigen-binding portions thereof of the invention may be administered alone or in combination with one or more other drugs or antibodies (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with," referring to the antibody compositions, antibodies and antigen-binding portions thereof, and bi-specific binding molecules of the invention with one or more other therapeutic agents, is intended to mean, and does refer to and include the following:

simultaneous administration of such combination of antibody composition/antibody/antigen-binding portion/bi-specific binding molecule of the invention and therapeutic agent(s) to a patient in need of treatment, when such components are formulated together into a single dosage form which releases said components at substantially the same time to said patient, substantially simultaneous administration of such combination of antibody composition/antibody/antigen-binding portion/bi-specific binding molecule of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination of antibody composition/antibody/antigen-binding portion/bi-specific binding molecule of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of antibody composition/antibody/antigen-binding portion/bi-specific binding molecule of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The antibody compositions, antibodies and antigen-binding portions thereof, and bi-specific binding molecules of the invention may be administered without additional therapeutic treatments, i.e., as a stand-alone therapy. Alternatively, treatment with the antibody compositions and antibodies and antigen-binding portions thereof of the invention may include at least one additional therapeutic treatment (combination therapy). In some embodiments, the antibody composition or antibody or antigen-binding portion thereof may be co-administered or formulated with another medication/drug for the treatment of cancer. The additional therapeutic treatment may comprise, e.g., a chemotherapeutic, anti-neoplastic, or anti-angiogenic agent, a different anti-cancer antibody, and/or radiation therapy.

By combining the antibody compositions, antibodies or antigen-binding portions, or bi-specific binding molecules of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. In some embodiments, the compound is selected from the group consisting of retinoic acid, phenylbutyrate, all-trans-retinoic acid and active form vitamin D.

Pharmaceutical articles comprising an anti-TIM-3 antibody composition, anti-TIM-3 antibody or antigen-binding portion thereof, or bi-specific binding molecule of the invention and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, e.g., fluorouracil and/or other fluoropyrimidines.

An anti-TIM-3 antibody or antigen-binding portion thereof, bi-specific binding molecule, or anti-TIM-3 antibody composition of the invention may also be used in combination with other anti-cancer therapies such as vaccines, cytokines, enzyme inhibitors and T cell therapies. In the case of a vaccine, it may, e.g., be a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example 1-methyl-D-tryptophan (1-D-MT). Adoptive T cell therapy refers to various immunotherapy techniques that involve expanding or engineering patients' own T cells to recognize and attack their tumors.

It is also contemplated that an anti-TIM-3 antibody or antigen-binding portion thereof, bi-specific binding molecule, or anti-TIM-3 antibody composition of the invention may be used in adjunctive therapy in connection with tyrosine kinase inhibitors. These are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site.

In some embodiments, the antibody composition, bi-specific binding molecule, or antibody or antigen-binding portion thereof may be used in combination with another medication/drug that mediates immune system activation, including, but not limited to, an agent that mediates the expression or activity of A2AR, BLTA, B7-H3, B7-H4, CTLA-4, CD27, CD28, CD39, CD40, CD55, CD73, CD122, CD137, CD160, CGEN-15049, CHK1, CHK2, CTLA-3, CEACAM (e.g., CEACAM-1 and/or CEACAM-5), galectin-9, GITR, HVEM, ICOS, IDO, KIR, LAIR1, LAG-3, NKG2A, OX40, PD-1/PD-L1/PD-L2, TIGIT, TGFR-beta, TNFR2, VISTA and/or 2B4. In certain embodiments, the agent is an antibody or an antigen-binding fragment thereof that binds to one of the above molecules.

In certain aspects, the antibodies and antigen-binding portions, compositions, and bi-specific binding molecules of the invention may be administered in combination with another inhibitor of the TIM-3 pathway, which may target TIM-3 or one or more of its ligands. Examples of such inhibitors include other anti-TIM-3 antibodies and antibodies that target TIM-3 ligands and/or co-receptors such as galectin-9, HMGB-1, phosphatidylserine lipids, CEACAM1, LILRA1-6, or LILRB1-5.

It is understood that the antibody compositions, bi-specific binding molecules, and antibodies and antigen-binding portions thereof of the invention may be used in a method of treatment as described herein, may be for use in a treatment as described herein, and/or may be for use in the manufacture of a medicament for a treatment as described herein.

Dose and Route of Administration

The antibody compositions of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

It is contemplated that a suitable dose of an antibody composition of the invention will be in the range of 0.1-100 mg/kg, such as about 0.5-50 mg/kg, e.g., about 1-20 mg/kg. The antibody composition may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

An effective amount for tumor therapy may be measured by its ability to stabilize disease progression and/or ameliorate symptoms in a patient, and preferably to reverse disease progression, e.g., by reducing tumor size. The ability of an antibody, antigen-binding portion, bi-specific binding molecule, or composition of the invention to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

Diagnostic Uses and Compositions

The antibodies and antigen-binding portions of the present invention also are useful in diagnostic processes (e.g., in vitro, ex vivo). For example, the antibodies and portions can be used to detect and/or measure the level of TIM-3 in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassay, and immunohistology. The invention further encompasses kits (e.g., diagnostic kits) comprising the antibodies and antigen-binding portions described herein.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Example 1: Cloning of Anti-TIM-3 Antibodies from Rat B Cells

This example describes the method used for generating the anti-human TIM-3 antibodies of the invention. The DNA and amino acid sequences of the antibodies are also provided.

Materials and Methods

The anti-TIM-3 antibodies of the invention were isolated from an antibody repertoire derived from OmniRat® rats (Osborn et al., *J Immunol.* 190(4):1481-90 (2013)), a rat strain from OMT (Open Monoclonal Technology, Inc.) that produces antibodies with fully human idiotypes. Cloning of rat-derived antibody genes from single-cell sorted antibody- A Symplex™ antibody library was prepared from single-cell sorted B cells from immunized OmniRat® rats, the library containing cognate VH and VL encoding pairs for each sorted B cell. The antibody repertoire constructs encoding fully human immunoglobulins in IgG1 or IgG2 format were transfected into Expi293 cells, and cell supernatants were screened for binding properties in a high-throughput format. Screening hits were analysed by DNA sequencing and antibody-encoding DNA sequences were extracted. Selected antibody clones were expressed and tested functionally as described below. Table 1 shows the heavy and light chain variable domain nucleic acid sequences of antibody clone 15086.15086. Table 2 shows the heavy and light chain amino acid sequences for said antibody clone, and Table 4 shows the heavy and light chain CDR amino acid sequences. Table 3 shows the amino acid sequences of the IgG1 heavy chain constant region and the kappa light chain constant region.

Due to the use of degenerated primers in the Symplex™ cloning of antibody-encoding cDNA fragments, a number of missense mutations in the amino termini of heavy and light chains were corrected for certain antibodies (e.g., antibodies 15086.16837, 15086.17145, and 15086.17144). Table 5 shows the heavy and light chain variable domain sequences at the DNA level from the optimized antibody designated 15086.16837, 15086.17145, or 15086.17144 (these three variants differ in isotype subtype but have identical heavy and light chain variable domain sequences). The optimization process includes matching amino terminal correction to germline as well as codon usage optimization. The targets for matching to human germline sequences were IGHV4-31 for the heavy chain variable domains and IGKV3-11 for the light chain variable domains.

Additional antibodies defining different epitope bins were identified. The heavy and light chain variable domain sequences of these antibodies are shown in Table 9 and Table 10. Additional functional antibodies were identified and the heavy and light chain variable domain sequences of these are shown in Table 12 and Table 13.

Results

Table 1 shows the DNA sequences encoding the Symplex™-cloned antibody 15086.15086.

TABLE 1

DNA sequences of variable domains of Symplex ™-cloned antibody 15086.15086

| | Sequence (5' to 3') |
|---|---|
| VH DNA sequence (SEQ ID NO: 1) | CAGGTGCAGCTACAGCAGTCGGGCCCAGGACTGGTGAAGCCTTCACAGACCCTGTCCCT CACCTGCACTGTCTCTGGTGGCTCCATCAGCAGTGGTGGTTACTACTGGAGTTGGACCC GTCAGCACCCAGGGATGGGCCTGGAGTGGATTGGATACATCTCTTACAGTGGGAGTATC TATTACACTCCGTCCCTCAAGAGTCGACTTACCATATCAGTGGACACGTCTAAGAACCA GTTCTCCCTGAAGCTGAGCTCTGTGACTGCCGCGGACACGGCCGTATATTACTGTGCGA GTTTGGATTCCTGGGGATCTAACCGTGACTACTGGGGCCAGGGAACCCTGGTCACCGTC TCGAGT |
| VL DNA sequence (SEQ ID NO: 2) | GAAATTGTGTTGACGCAGTCTCCAGCCACCCTGTCTTTGTCTCCAGGGGAAAGAGCCAC CCTCTCCTGCAGGGCCAGTCAGAGTGTTAGCAGCTACTTAGCCTGGTACCAACAGAAAC CTGGCCAGGCTCCCAGGCTCCTCATCTATGATGCATCCAACAGGGCCACTGGCATCCCA GCCAGGTTCAGTGGCAGTGGGTCTGGGACAGACTTCACTCTCACCATCAGCAGCCTAGA GCCTGAAGATTTTGCAGTTTATTACTGTCAGCAGCGTAGCAACTGGCCGCTCACTTTCG GCGGAGGGACCAAGGTGGAGATTAAG | secreting B cells (ASC) was performed by means of the Symplex™ antibody discovery technology (Meijer et al., *J Mol Biol* 358(3):764-72 (2006)).

Table 2 shows the deduced protein sequences of the original Symplex™-cloned antibody 15086.15086. CDRs are shown bolded and italicized.

TABLE 2

| Protein sequences of variable domains of Symplex ™-cloned antibody 15086.15086 |
| --- |

| Sequence (N-terminal to C-terminal) |
| --- |

| VH protein sequence (SEQ ID NO: 3) | QVQLQQSGPGLVKPSQTLSLTCTVS*GGSISSGGYY*WSWTRQHPGMGLEWIGY*ISYSGS IYYTPSLKSRLTISVDTSKNQFSLKLSSVTAADTAVYY*CASLDSWGSNRDYW*GQGTLV TVSS |
| VL protein sequence (SEQ ID NO: 4) | EIVLTQSPATLSLSPGERATLSCRAS*QSVSSY*LAWYQQKPGQAPRLLIY*DAS*NRATGI PARFSGSGSGTDFTLTISSLEPEDFAVYY*CQQRSNWPLTF*FGGGTKVEIK |

15

Table 3 shows heavy and light chain constant regions.

TABLE 3

| Protein sequences of constant regions |
| --- |

| Sequence (N-terminal to C-terminal) |
| --- |

| IgG1 heavy chain constant region (SEQ ID NO: 5) | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKRVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSFFLYSKLTV DKSRWQQGNVFSCSVMHEALHNHYTQKSLSLSPGK |
| Kappa light chain constant region (SEQ ID NO: 6) | RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |

35

Table 4 shows the heavy and light chain complementarity determining regions (CDRs) shared by antibodies 15086.15086, 15086.16837, 15086.17145, and 15086.17144. The CDR sequences herein were determined according to the IMGT® definitions for CDR1 and CDR2. For heavy and light chain CDR3, the definitions herein include one extra amino acid residue upstream of the IMGT-CDR3 (Cys) and one extra amino acid residue downstream (Trp for VH CDR3, Phe for VL CDR3).

40

TABLE 4

| Protein sequences of CDRs of antibodies 15086.15086, 15086.16837, 15086.17145, and 15086.17144 |
| --- |

| Region | Sequence (N-terminal to C-terminal) |
| --- | --- |
| HCDR1 (SEQ ID NO: 7) | GGSISSGGYY |
| HCDR2 (SEQ ID NO: 8) | ISYSGSI |
| HCDR3 (SEQ ID NO: 9) | CASLDSWGSNRDYW |
| LCDR1 (SEQ ID NO: 10) | QSVSSY |
| LCDR2 (SEQ ID NO: 11) | DAS |
| LCDR3 (SEQ ID NO: 12) | CQQRSNWPLTF |

Table 5 shows optimized DNA sequences encoding the heavy and light chain variable domains shared by antibodies 15086.16837, 15086.17145, and 15086.17144.

TABLE 5

| Optimized DNA sequences encoding variable domains of antibodies 15086.16837, 15086.17145, and 15086.17144 | |
|---|---|
| | Sequence (5' to 3') |
| VH DNA sequence (SEQ ID NO: 13) | CAGGTGCAGCTGCAGGAGAGTGGCCCCGGACTGGTCAAGCCTTCACAGACTCTGAGCCT GACCTGCACAGTGTCTGGCGGAAGTATCAGCTCCGGGGGTTACTATTGGAGCTGGACCC GACAGCACCCAGGAATGGGTCTGGAATGGATCGGGTACATTTCATATAGCGGCTCCATC TACTATACACCCTCACTGAAAAGCAGGCTGACCATTTCCGTGGACACATCTAAGAACCA GTTCAGCCTGAAACTGTCTAGTGTGACAGCCGCTGATACTGCAGTCTACTATTGTGCCT CCCTGGACTCTTGGGGCAGTAATAGAGATTACTGGGGCCAGGGAACTCTGGTCACCGTC TCGAGT |
| VL DNA sequence (SEQ ID NO: 14) | GAGATCGTGCTGACTCAGTCCCCAGCCCACCCTGTCACTGAGCCCAGGAGAACGAGCAAC CCTGTCTTGCAGGGCCTCCCAGTCTGTCAGCTCCTACCTGGCTTGGTATCAGCAGAAGC CCGGGCAGGCACCTCGACTGCTGATCTACGACGCCAGTAACAGAGCTACCGGTATTCCC GCCCGCTTCAGTGGTTCAGGCAGCGGAACAGACTTTACCCTGACAATCTCTAGTCTGGA GCCTGAAGATTTCGCCGTGTACTATTGTCAGCAGAGGTCTAATTGGCCACTGACATTTG GCGGAGGGACTAAGGTCGAGATCAAG |

Table 6 shows the deduced heavy and light chain variable domain protein sequences shared by antibodies 15086.16837, 15086.17145, and 15086.17144. CDRs are shown bolded and italicized. Note that the VL protein sequence is the same as the non-optimized VL protein sequence.

TABLE 6

| Protein sequences of variable domains of optimized antibodies 15086.16837, 15086.17145, and 15086.17144 | |
|---|---|
| | Sequence (N-terminal to C-terminal) |
| VH protein sequence (SEQ ID NO: 15) | QVQLQESGPGLVKPSQTLSLTCTVS*GGSISSGGYY*WSWTRQHPGMGLEWIGY*ISYSGSI* YYTPSLKSRLTISVDTSKNQFSLKLSSVTAADTAVYY*CASLDSWGSNRDYW*GQGTLVTV SS |
| VL protein sequence (SEQ ID NO: 4 ) | EIVLTQSPATLSLSPGERATLSCRAS*QSVSSY*LAWYQQKPGQAPRLLIY*DAS*NRATGIP ARFSGSGSGTDFTLTISSLEPEDFAVYY*CQQRSNWPLTF*GGGTKVEIK |

Table 7 shows the DNA sequences encoding antibody constant regions in different isotype formats.

TABLE 7

| DNA sequences encoding antibody constant regions in different isotype formats | | |
|---|---|---|
| | Description | Sequence (5' to 3') |
| IgG1-LALA heavy chain constant region (SEQ ID NO: 16) | IgG1-LALA heavy chain constant region excluding introns | GCCTCCACCAAGGGCCCATCGGTCTTCCCCCTGGCACCCTCCTCCAA GAGCACCTCTGGGGGCACAGCGGCCCTGGGCTGCCTGGTCAAGGACT ACTTCCCCGAACCGGTGACGGTGTCGTGGAACTCAGGCGCCCTGACC AGCGGCGTGCACACCTTCCCGGCTGTCCTACAGTCCTCAGGACTCTA CTCCCTCAGCAGCGTGGTGACCGTGCCCTCCAGCAGCTTGGGCACCC AGACCTACATCTGCAACGTGAATCACAAGCCCAGCAACACCAAGGTG GACAAGAGAGTTGAGCCCAAATCTTGTGACAAAACTCACACATGCCC ACCGTGCCCAGCACCTGAAGCCGCCGGGGGACCGTCAGTCTTCCTCT TCCCCCCAAAACCCAAGGACACCCTCATGATCTCCCGGACCCCTGAG GTCACATGCGTGGTGGTGGACGTGAGCCACGAAGACCCTGAGGTCAA GTTCAACTGGTACGTGGACGGCGTGGAGGTGCATAATGCCAAGACAA AGCCGCGGGAGGAGCAGTACAACAGCACGTACCGTGTGGTCAGCGTC CTCACCGTCCTGCACCAGGACTGGCTGAATGGCAAGGAGTACAAGTG CAAGGTCTCCAACAAAGCCCTCCCAGCCCCCATCGAGAAAACCATCT CCAAAGCCAAAGGGCAGCCCCGAGAACCACAGGTGTACACCCTGCCC CCATCCCGGGAGGAGATGACCAAGAACCAGGTCAGCCTGACCTGCCT |

TABLE 7-continued

| | Description | Sequence (5' to 3') |
|---|---|---|

DNA sequences encoding antibody constant regions in different isotype formats

| | Description | Sequence (5' to 3') |
|---|---|---|
| | | GGTCAAAGGCTTCTATCCCAGCGACATCGCCGTGGAGTGGGAGAGCA |
| | | ATGGGCAGCCGGAGAACAACTACAAGACCACGCCTCCCGTGCTGGAC |
| | | TCCGACGGCTCCTTCTTCCTCTATAGCAAGCTCACCGTGGACAAGAG |
| | | CAGGTGGCAGCAGGGGAACGTCTTCTCATGCTCCGTGATGCATGAGG |
| | | CTCTGCACAACCACTACACGCAGAAGAGCCTCTCCCTGTCCCCGGGT |
| | | AAA |
| IgG1-LALA heavy chain constant region (SEQ ID NO: 17) | IgG1-LALA heavy chain constant region including introns | GCCTCCACCAAGGGCCCATCGGTCTTCCCCCTGGCACCCTCCTCCAA GAGCACCTCTGGGGGCACAGCGGCCCTGGGCTGCCTGGTCAAGGACT ACTTCCCCGAACCGGTGACGGTGTCGTGGAACTCAGGCGCCCTGACC AGCGGCGTGCACACCTTCCCGGCTGTCCTACAGTCCTCAGGACTCTA CTCCCTCAGCAGCGTGGTGACCGTGCCCTCCAGCAGCTTGGGCACCC AGACCTACATCTGCAACGTGAATCACAAGCCCAGCAACACCAAGGTG GACAAGAGAGTTGGTGAGAGGCCAGCACAGGGAGGGAGGGTGTCTGC TGGAAGCCAGGCTCAGCGCTCCTGCCTGGACGCATCCCGGCTATGCA GTCCCAGTCCAGGGCAGCAAGGCAGGCCCCGTCTGCCTCTTCACCCG GAGGCCTCTGCCCCGCCCCACTCATGCTCAGGGAGAGGGTCTTCTGGC TTTTTCCCCAGGCTCTGGGCAGGCACAGGCTAGGTGCCCCTAACCCA GGCCCTGCACACAAAGGGGCAGGTGCTGGGCTCAGACCTGCCAAGAG CCATATCCGGGAGGACCCTGCCCCTGACCTAAGCCCACCCCAAAGGC CAAACTCTCCACTCCCTCAGCTCGGACACCTTCTCTCCTCCCAGATT CCAGTAACTCCCAATCTTCTCTCTGCAGAGCCCAAATCTTGTGACAA AACTCACACATGCCCACCGTGCCCAGGTAAGCCAGCCCAGGCCTCGC CCTCCAGCTCAAGGCGGGACAGGTGCCCTAGAGTAGCCTGCATCCAG GGACAGGCCCCAGCCGGGTGCTGACACGTCCACCTCCATCTCTTCCT CAGCACCTGAAgccgccGGGGGACCGTCAGTCTTCCTCTTCCCCCCA AAACCCAAGGACACCCTCATGATCTCCCGGACCCCTGAGGTCACATG CGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACAACAGCACGTACCGTGTGGTCAGCGTCCTCACCGT CCTGCACCAGGACTGGCTGAATGGCAAGGAGTACAAGTGCAAGGTCT CCAACAAAGCCCTCCCAGCCCCCATCGAGAAAACCATCTCCAAAGCC AAAGGTGGGACCCGTGGGGTGCGAGGGCCACATGGACAGAGGCCGGC TCGGCCCACCCTCTGCCCTGAGAGTGACCGCTGTACCAACCTCTGTC CCTACAGGGCAGCCCCGAGAACCACAGGTGTACACCCTGCCCCCATC CCGGGAGGAGATGACCAAGAACCAGGTCAGCCTGACCTGCCTGGTCA AAGGCTTCTATCCCAGCGACATCGCCGTGGAGTGGGAGAGCAATGGG CAGCCGGAGAACAACTACAAGACCACGCCTCCCGTGCTGGACTCCGA CGGCTCCTTCTTCCTCTATAGCAAGCTCACCGTGGACAAGAGCAGGT GGCAGCAGGGGAACGTCTTCTCATGCTCCGTGATGCATGAGGCTCTG CACAACCACTACACGCAGAAGAGCCTCTCCCTGTCCCCGGGTAAA |
| IgG4 (S228P) heavy chain constant region (SEQ ID NO: 18) | IgG4 (S228P) heavy chain constant region excluding introns | GCTTCCACCAAGGGCCCATCGGTCTTCCCCCTGGCGCCCTGCTCCAG GAGCACCTCCGAGAGCACAGCCGCCCTGGGCTGCCTGGTCAAGGACT ACTTCCCCGAACCGGTGACGGTGTCGTGGAACTCAGGCGCCCTGACC AGCGGCGTGCACACCTTCCCGGCTGTCCTACAGTCCTCAGGACTCTA CTCCCTCAGCAGCGTGGTGACCGTGCCCTCCAGCAGCTTGGGCACGA AGACCTACACCTGCAACGTAGATCACAAGCCCAGCAACACCAAGGTG GACAAGAGAGTTGAGTCCAAATATGGTCCCCCATGCCCAcCATGCCC AGCACCTGAGTTCCTGGGGGGACCATCAGTCTTCCTGTTCCCCCCAA AACCCAAGGACACTCTCATGATCTCCCGGACCCCTGAGGTCACGTGC GTGGTGGTGGACGTGAGCCAGGAAGACCCCGAGGTCCAGTTCAACTG GTACGTGGATGGCGTGGAGGTGCATAATGCCAAGACAAAGCCGCGGG AGGAGCAGTTCAACAGCACGTACCGTGTGGTCAGCGTCCTCACCGTC CTGCACCAGGACTGGCTGAACGGCAAGGAGTACAAGTGCAAGGTCTC CAACAAAGGCCTCCCGTCCTCCATCGAGAAAACCATCTCCAAAGCCA AAGGGCAGCCCCGAGAGCCACAGGTGTACACCCTGCCCCCATCCCAG GAGGAGATGACCAAGAACCAGGTCAGCCTGACCTGCCTGGTCAAAGG CTTCTACCCCAGCGACATCGCCGTGGAGTGGGAGAGCAATGGGCAGC CGGAGAACAACTACAAGACCACGCCTCCCGTGCTGGACTCCGACGGC TCCTTCTTCCTCTACAGCAGGCTCACCGTGGACAAGAGCAGGTGGCA GGAGGGGAATGTCTTCTCATGCTCCGTGATGCATGAGGCTCTGCACA ACCACTACACAGAAGAGCCTCTCCCTGTCTCTGGGTAAA |
| IgG4 (S228P) heavy chain constant region (SEQ ID NO: 19) | IgG4 (S228P) heavy chain constant region including introns | GCTTCCACCAAGGGCCCATCGGTCTTCCCCCTGGCGCCCTGCTCCAG GAGCACCTCCGAGAGCACAGCCGCCCTGGGCTGCCTGGTCAAGGACT ACTTCCCCGAACCGGTGACGGTGTCGTGGAACTCAGGCGCCCTGACC AGCGGCGTGCACACCTTCCCGGCTGTCCTACAGTCCTCAGGACTCTA CTCCCTCAGCAGCGTGGTGACCGTGCCCTCCAGCAGCTTGGGCACGA AGACCTACACCTGCAACGTAGATCACAAGCCCAGCAACACCAAGGTG GACAAGAGAGTTGGTGAGAGGCCAGCACAGGGAGGGAGGGTGTCTGC TGGAAGCCAGGCTCAGCCCTCCTGCCTGGACGCACCCCGGCTGTGCA GCCCCAGCCCAGGGCAGCAAGGCAGGCCCCATCTGTCTCCTCACCCG GAGGCCTCTGACCACCCCACTCATGCTCAGGGAGAGGGTCTTCTGGA TTTTTCCACCAGGCTCCGGGCAGCCACAGGCTGGATGCCCCTACCCC |

TABLE 7-continued

DNA sequences encoding antibody constant regions in different isotype formats

| | Description | Sequence (5' to 3') |
|---|---|---|
| | | AGGCCCTGaGCATACAGGGGCAGGTGCTGCGCTCAGACCTGCCAAGA<br>GCCATATCCGGGAGGACCCTGCCCCTGACCTAAGCCCACCCCAAAGG<br>CCAAACTCTCCACTCCCTCAGCTCAGACACCTTCTCTCCTCCCAGAT<br>CTGAGTAACTCCCAATCTTCTCTCTGCAGAGTCCAAATATGGTCCCC<br>CATGCCCAcCATGCCCAGGTAAGCCAACCCAGGCCTCGCCCTCCAGC<br>TCAAGGCGGGACAGGTGCCCTAGAGTAGCCTGCATCCAGGGACAGGC<br>CCCAGCCGGGTGCTGACGCATCCACCTCCATCTCTTCCTCAGCACCT<br>GAGTTCCTGGGGGGACCATCAGTCTTCCTGTTCCCCCCAAAACCCAA<br>GGACACTCTCATGATCTCCCGGACCCCTGAGGTCACGTGCGTGGTGG<br>TGGACGTGAGCCAGGAAGACCCCGAGGTCCAGTTCAACTGGTACGTG<br>GATGGCGTGGAGGTGCATAATGCCAAGACAAAGCCGCGGGAGGAGCA<br>GTTCAACAGCACGTACCGTGTGGTCAGCGTCCTCACCGTCCTGCACC<br>AGGACTGGCTGAACGGCAAGGAGTACAAGTGCAAGGTCTCCAACAAA<br>GGCCTCCCGTCCTCCATCGAGAAAACCATCTCCAAAGCCAAAGGTGG<br>GACCCACGGGGTGCGAGGGCCACATGGACAGAGGTCAGCTCGGCCCA<br>CCCTCTGCCCTGGGAGTGACCGCTGTGCCAACCTCTGTCCCTACAGG<br>GCAGCCCCGAGAGCCACAGGTGTACACCCTGCCCCCCATCCCAGGAGG<br>AGATGACCAAGAACCAGGTCAGCCTGACCTGCCTGGTCAAAGGCTTC<br>TACCCCAGCGACATCGCCGTGGAGTGGGAGAGCAATGGGCAGCCGGA<br>GAACAACTACAAGACCACGCCTCCCGTGCTGGACTCCGACGGCTCCT<br>TCTTCCTCTACAGCAGGCTCACCGTGGACAAGAGCAGGTGGCAGGAG<br>GGGAATGTCTTCTCATGCTCCGTGATGCATGAGGCTCTGCACAACCA<br>CTACACACAGAAGAGCCTCTCCCTGTCTCTGGGTAAA |
| IgG2<br>heavy<br>chain<br>constant<br>region<br>(SEQ ID<br>NO: 20) | IgG2 heavy<br>chain<br>constant<br>region<br>excluding<br>introns | GCCTCCACCAAGGGCCCATCGGTCTTCCCCCTGGCGCCCTGCTCCAG<br>GAGCACCTCCGAGAGCACAGCCGCCCTGGGCTGCCTGGTCAAGGACT<br>ACTTCCCCGAACCGGTGACGGTGTCGTGGAACTCAGGCGCTCTGACC<br>AGCGGCGTGCACACCTTCCCAGCTGTCCTACAGTCCTCAGGACTCTA<br>CTCCCTCAGCAGCGTGGTGACCGTGCCCTCCAGCAACTTCGGCACCC<br>AGACCTACACCTGCAACGTAGATCACAAGCCCAGCAACACCAAGGTG<br>GACAAGACAGTTGAGCGCAAATGTTGTGTCGAGTGCCCACCGTGCCC<br>AGCACCACCTGTGGCAGGACCGTCAGTCTTCCTCTTCCCCCCAAAAC<br>CCAAGGACACCCTCATGATCTCCCGGACCCCTGAGGTCACGTGCGTG<br>GTGGTGGACGTGAGCCACGAAGACCCCGAGGTCCAGTTCAACTGGTA<br>CGTGGACGGCGTGGAGGTGCATAATGCCAAGACAAAGCCACGGGAGG<br>AGCAGTTCAACAGCACGTTCCGTGTGGTCAGCGTCCTCACCGTTGTG<br>CACCAGGACTGGCTGAACGGCAAGGAGTACAAGTGCAAGGTCTCCAA<br>CAAAGGCCTCCCAGCCCCCATCGAGAAAACCATCTCCAAAACCAAAG<br>GGCAGCCCCGAGAACCACAGGTGTACACCCTGCCCCCATCCCGGGAG<br>GAGATGACCAAGAACCAGGTCAGCCTGACCTGCCTGGTCAAAGGCTT<br>CTACCCCAGCGACATCGCCGTGGAGTGGGAGAGCAATGGGCAGCCGG<br>AGAACAACTACAAGACCACACCTCCCATGCTGGACTCCGACGGCTCC<br>TTCTTCCTCTACAGCAAGCTCACCGTGGACAAGAGCAGGTGGCAGCA<br>GGGGAACGTCTTCTCATGCTCCGTGATGCATGAGGCTCTGCACAACC<br>ACTACACGCAGAAGAGCCTCTCCCTGTCTCCGGGTAAA |
| IgG2<br>heavy<br>chain<br>constant<br>region<br>(SEQ ID<br>NO: 21) | IgG2 heavy<br>chain<br>constant<br>region<br>including<br>introns | GCCTCCACCAAGGGCCCATCGGTCTTCCCCCTGGCGCCCTGCTCCAG<br>GAGCACCTCCGAGAGCACAGCCGCCCTGGGCTGCCTGGTCAAGGACT<br>ACTTCCCCGAACCGGTGACGGTGTCGTGGAACTCAGGCGCTCTGACC<br>AGCGGCGTGCACACCTTCCCAGCTGTCCTACAGTCCTCAGGACTCTA<br>CTCCCTCAGCAGCGTGGTGACCGTGCCCTCCAGCAACTTCGGCACCC<br>AGACCTACACCTGCAACGTAGATCACAAGCCCAGCAACACCAAGGTG<br>GACAAGACAGTTGGTGAGAGGCCAGCTCAGGGAGGGAGGGTGTCTGC<br>TGGAAGCCAGGCTCAGCCCTCCTGCCTGGACGCACCCCGGCTGTGCA<br>GCCCCAGCCCAGGGCAGCAAGGCAGGCCCCATCTGTCTCCTCACCCG<br>GAGGCCTCTGCCCGCCCCACTCATGCTCAGGGAGAGGGTCTTCTGGC<br>TTTTTCCACCAGGCTCCAGGCAGGCACAGGCTGGGTGCCCCTACCCC<br>AGGCCCTTCACACACAGGGGCAGGTGCTTGGCTCAGACCTGCCAAAA<br>GCCATATCCGGGAGGACCCTGCCCCTGACCTAAGCCGACCCCAAAGG<br>CCAAACTGTCCACTCCCTCAGCTCGGACACCTTCTCTCCTCCCAGAT<br>CCGAGTAACTCCCAATCTTCTCTCTGCAGAGCGCAAATGTTGTGTCG<br>AGTGCCCACCGTGCCCAGGTAAGCCAGCCCAGGCCTCGCCCTCCAGC<br>TCAAGGCGGGACAGGTGCCCTAGAGTAGCCTGCATCCAGGGACAGGC<br>CCCAGCTGGGTGCTGACACGTCCACCTCCATCTCTTCCTCAGCACCA<br>CCTGTGGCAGGACCGTCAGTCTTCCTCTTCCCCCCAAAACCCAAGGA<br>CACCCTCATGATCTCCCGGACCCCTGAGGTCACGTGCGTGGTGGTGG<br>ACGTGAGCCACGAAGACCCCGAGGTCCAGTTCAACTGGTACGTGGAC<br>GGCGTGGAGGTGCATAATGCCAAGACAAAGCCACGGGAGGAGCAGTT<br>CAACAGCACGTTCCGTGTGGTCAGCGTCCTCACCGTTGTGCACCAGG<br>ACTGGCTGAACGGCAAGGAGTACAAGTGCAAGGTCTCCAACAAAGGC<br>CTCCCAGCCCCCATCGAGAAAACCATCTCCAAAACCAAAGGTGGGAC<br>CCGCGGGGTATGAGGGCCACATGGACAGAGGCCGGCTCGGCCCACCC<br>TCTGCCCTGGGAGTGACCGCTGTGCCAACCTCTGTCCCTACAGGGCA<br>GCCCCGAGAACCACAGGTGTACACCCTGCCCCCATCCCGGGAGGAGA<br>TGACCAAGAACCAGGTCAGCCTGACCTGCCTGGTCAAAGGCTTCTAC |

TABLE 7-continued

| | Description | Sequence (5' to 3') |
|---|---|---|
| DNA sequences encoding antibody constant regions in different isotype formats | | |
| | | CCCAGCGACATCGCCGTGGAGTGGGAGAGCAATGGGCAGCCGGAGAA |
| | | CAACTACAAGACCACACCTCCCATGCTGGACTCCGACGGCTCCTTCT |
| | | TCCTCTACAGCAAGCTCACCGTGGACAAGAGCAGGTGGCAGCAGGGG |
| | | AACGTCTTCTCATGCTCCGTGATGCATGAGGCTCTGCACAACCACTA |
| | | CACGCAGAAGAGCCTCTCCCTGTCTCCGGGTAAA |
| Kappa light chain constant region (SEQ ID NO: 22) | | CGTACGGTGGCTGCACCATCTGTCTTCATCTTCCCGCCATCTGATGA GCAGTTGAAATCTGGAACTGCCTCTGTTGTGTGCCTGCTGAATAACT TCTATCCCAGAGAGGCCAAAGTACAGTGGAAGGTGGATAACGCCCTC CAATCGGGTAACTCCCAGGAGAGTGTCACAGAGCAGGACAGCAAGGA CAGCACCTACAGCCTCAGCAGCACCCTGACGCTGAGCAAAGCAGACT ACGAGAAACACAAAGTCTACGCCTGCGAAGTCACCCATCAGGGCCTG AGCTCGCCCGTCACAAAGAGCTTCAACAGGGGAGAGTGT |

Table 8 shows the protein sequences of antibody constant regions in different isotype formats.

TABLE 8

| | Sequence (N-terminal to C-terminal) |
|---|---|
| Protein sequences of antibody constant regions in different isotype formats | |
| IgG1-LALA heavy chain constant region (SEQ ID NO: 23) | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGK |
| IgG4 (S228P) heavy chain constant region (SEQ ID NO: 24) | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEF LGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFF LYSRLTVDKSRWQEGNVFSCSVMHEALHNHYTQKSLSLSLGK |
| IgG2 heavy chain constant region (SEQ ID NO: 25) | ASTKGPSVFPLAPCSRSTSESTAALGCLVKDYFPEPVTVSWNSGALTSGVHTFPAVL QSSGLYSLSSVVTVPSSNFGTQTYTCNVDHKPSNTKVDKTVERKCCVECPPCPAPPV AGPSVFLFPPKPKDTLMISRTPEVTCVVVDVSHEDPEVQFNWYVDGVEVHNAKTKPR EEQFNSTFRVVSVLTVVHQDWLNGKEYKCKVSNKGLPAPIEKTISKTKGQPREPQVY TLPPSREEMTKNQVSLTCLVKGFYPSDIAVEWESNGQPENNYKTTPPMLDSDGSFFL YSKLTVDKSRWQQGNVFSCSVMHEALHNHYTQKSLSLSPGK |

Table 9 shows the DNA sequences encoding heavy and light chain variable domains of anti-TIM-3 antibodies used for epitope binning.

TABLE 9

| Ab | SEQ ID NO: | Sequence (5' to 3') |
|---|---|---|
| DNA sequences of variable domains of anti-TIM-3 binning antibodies | | |
| 20131 VH | 26 | CAGGTGCAGCTACAGCAGTCTGGGGGAGGCTTGGTACAGCCTGGGGGGTCCCTGA GACTCTCCTGTGCAGCCTCTGGATTCACCTTAAGCAGCTATGCCATGAGCTGGGT CCGCCAGGCTCCAGGGAAGGGGCTGGAGTGGGTCTCAGGTATTAGTGGTAGTGGT GGTAGCACATACAACGCAGACTCCGTGAAGGGCCGGTTCACCATCTCCAGAGACA ATTCCAAGAACACGCTGTTTCTGCAAATGAACAGCCTGAGAGCCGAGGACACGGC CGTATATTACTGTGCGAAATTTTTGGGTCCTACTACTTTGACTACTGGGGCCAG GGAACCCTGGTCACAGTCTCGAGT |
| 20131 VL | 27 | GAAATTGTGATGACACAGTCTCCAGACTCCCTGGCTGTGTCTCTGGGCGAGAGGG CCACCATCAACTGCAAGTCCAGCCAGAGTGTTTTATACAGCTCCAACAATAAGAA CTACTTAGCTTGGTACCAGCAGAAACCAGGACAGCCTCCTAAGCTGCTCATTTAC TGGACATCTACCCGGGAATCCGGGGTCCCTAACCGATTCAGTGGCAGCGGGTCTG GGACAGATTTCACTCTCACCATCAGCAGCCTGCAGGCTGAAGATGTGGCAGTTTA |

TABLE 9-continued

| | | |
|---|---|---|

DNA sequences of variable domains of anti-TIM-3 binning antibodies

| Ab | SEQ ID NO: | Sequence (5' to 3') |
|---|---|---|
| | | TTACTGTCAGCAATATTATAGTGGTCCTCCGACGTTCGGCCAAGGGACCAAGGTG GAAATCAAA |
| 20293 VH | 36 | ACGTGACAGGGCGCGCCCAGGTCCAGCTGCAGGAGAGCGGTCCCGGACTGGTGAA GCCATCCCAGACACTGAGCCTGACTTGTACTGTGAGCGGCGGTAGCATCTCCAGC GGCGGCTACTATTGGTCCTGGATCAGGCAGCACCCAGGCAAGGGCCTGGAGTGGA TCGGCTACATCTACTATAGCGGCTCTATCTACTATAACCCTTCCCTGAAGAGCCG GGTGACCATCTCTGTGGACACATCCAAGAATCAGTTCTATCTGAAGCTGTCTTCC GTGACCGCCGCTGATACAGCCGTGTACTATTGCGCCTCACTGATGGTCTGGGGGG TCATGGGCGATTACTGGGGGCAGGGCACACTGGTCACAGTCTCGAGT |
| 20293 VL | 37 | GAGATTGTGCTGACCCAGTCTCCCGCCACCCTGTCTCTGAGTCCTGGCGAGAGAG CCACCCTGAGCTGCAGAGCCTCTCAGTCCGTGTCCAGCTATCTGGCCTGGTATCA GCAGAAGCCCGGCCAGGCTCCCCGGCTGCTGATCTACGATGCCTCCAATAGAGCC ACCGGCATCCCTGCCAGATTCTCCGGCTCTGGCTCTGGCACCGACTTTACCCTGA CCATCTCCAGCCTGGAACCCGAGGACTTCGCCGTGTACTACTGCCAGCAGCGGTC CGACTGGCCTCCTACATTTGGCCAAGGCACCAAGGTGGAAATCAAG |
| 15105 VH | 46 | CAGGTCACCTTGAAGGAGTGGGGCGCAGGACTGTTGAGGCCCTCGGAGACCCTGT CCCTCACCTGCGCTGTCTATGGTGGGTCCTTCAGTGGTTACTACTGGAGCTGGAT CCGCCAGCCCCCAGGGAAGGGGCTGGAGTGGATAGGGGAAATCAATCATAGTGGA AGCACCAACTACAACCCGTCCCTCAAGAGTCGAGTCACCATATCAGTAGACGCGA CCAAGAAACAATTCTCCCTGAAGCTGACCTCTGTGACCGCCGCGGACACGGCTGT GTATTACTGTGCGAGATATTGGGAGCTCCCTGACTACTGGGGCCAGGGCACCCTG GTCACCGTCTCGAGT |
| 15105 VL | 47 | GACATCCAGTTGACCCAGTCTCCATCCTCCCTGTCTGCATCTGTAGGAGACAGAG TCACCATCACTTGCCGGGCAAGTCAGGGCATTAGAAATGATTTAGGCTGGTATCA GCAGAAACCAGGGAAAGCCCCTAAGCGCCTGATCTATGCTGCATCCAGTTTGCAA AGTGGGGTCCCATCAAGGTTCAGCGGCAGTGGATCTGGGACAGAATTCACTCTCA CAATCAGCAGCCTGCAGCCTGAAGATTTTGCAACTTATTACTGTCTACAGCATAA TAGTTACCCTCCGACGTTCGGCCAAGGGACCAAGGTGGAAATCAAG |
| 15107 VH | 56 | CAGATGCAGCTGGTGCAGTGGGGCGCAGGACTGTTGAAGCCTTCGGAGACCCTGT CCCTCACCTGCGCTGTCTATGGTGGGTCCTTCAGTGGTTACTACTGGAGCTGGAT CCGCCAGCCCCCAGGGAAGGGGCTGGAGTGGATTGGGGAAATCAATCATAGTGGA AGCACCAACTACAACCCGTCCCTCAAGAGTCGAGTCACCATGTCAGTTGACACGT CCAAGCACCAGTTCTCCCTGAAGCTGAGCTCTGTGACCGCCGCGGACACGGCTGT GTATTACTGTGCGAGATGGTGGGAGCTTCCTGACTACTGGGGCCAGGGAACCCTG GTCACCGTCTCGAGT |
| 15107 VL | 57 | GAAATTGTGTTGACGCAGTCTCCATCCTCCCTGTCTGCATCTGTAGGAGACAGAG TCACCATCACTTGCCGGGCAAGTCAGGGCATTAGAAATGATTTAGGCTGGTATCA GCAGAAACCAGGGAAAGCCCCTAAGCGCCTGATCTATGCTGCATCCAGTTTGCAA AGTGGGGTCCCATCAAGGTTCAGCGGCAGTGGATCTGGGACAGAATTCACTCTCA CAATCAGCAGCCTGCAGCCTGAAGATTTTGCAACTTATTACTGTCTACAGCATAA TAGTTACCCGTGGACGTTCGGCCAAGGGACCAAGGTGGAAATCAAG |
| 15109 VH | 66 | CAGATGCAGCTGGTGCAATGGGGCGCAGGACTGTTGAAGCCTTCGGAGACCCTGT CCCTCACCTGCGCTGTCTATGGTGGGTCCTTCAGTGGTTACTACTGGAGCTGGAT CCGCCAGCCCCCAGGGAAGGGGCTGGAGTGGATTGGGGAAATCAATCATAGTGGA AGCACCAACTACAACCCGTCCCTCAAGAGTCGAGTCACCATATCAGTAGACACGT CCAAGAACCAGTTCTCCCTGAAGCTGAGCTCTGTGACCGCCGCGGACACGGCTGT GTATTACTGTGCGAGGTTTTACTATGCTCCGAACTTTGACTACTGGGGCCAGGGC ACCCTGGTCACCGTCTCGAGT |
| 15109 VL | 67 | GAAATTGTGTTGACGCAGTCTCCTTCCACCCTGTCTGCATCTGTAGGAGACAGAG TCACCATCACTTGCCGGGCCAGTCAGAGTATTAGTAGCTGGTTGGCCTGGTATCA GCAGAAACCAGGGACAGCCCCTAAGCTCCTGATCTATAAGGCGTCTAGTTTAGAA AGTGGGGTCCCATCAAGGTTCAGCGGCAGTGGATCTGGGACAGAATTCACTCTCA CCATCAGCAGCCTGCAGCCTGATGATTTTGCAACTTATTACTGCCAACAGTATAA TAGTTATTCCACTTTCGGCGGAGGGACCAAGGTGGAGATCAAA |
| 15174 VH | 76 | CAGGTGCAGCTGCAGCAGTCGGGCCCAGGACTGGTGAAGCCTTCGGAGACCCTGT CCCTCACCTGCACTGTCTCTGGTGGCTCCATCAGCAGTAGTAATTACTACTGGGG CTGGATCCGCCAGCCCCCAGGGAAGGGGCTGGAGTGGATTGGGAGTATCTATTAT AGTGGGAACACCTACTACAACCCGTCCCTCAAGAGTCGAGTCACCATATCCGTAG ACACGTCCAAGAACCAGTTCTCCCTGAAGCTGAGTTCTGTGACCGCCGCAGACAC GGCTGTGTATTACTGTGCGAGACAGACAGTGGCTGGCCCCCTCTTTGACTACTGG GGCCAGGGAACCCTGGTCACCGTCTCGAGT |
| 15174 VL | 77 | GAAATTGTGATGACGCAGTCTCCTTCCACCCTGTCTGCATCTGTAGGAGACAGAG TCACCATCACTTGCCGGGCCAGTCAGAGTATTAGTAGCTGGTTGGCCTGGTATCA GCAGAAACCAGGGAAAGCCCCTAAGGTCCTGATCTATAAGGCGTCTAGTTTAGAA |

TABLE 9-continued

| Ab | SEQ ID NO: | Sequence (5' to 3') |
|---|---|---|

DNA sequences of variable domains of anti-TIM-3 binning antibodies

|  |  | AGTGGGGTCCCATCAAGGTTCAGCGGCAGTGGATCTGGGACAGAACTCACTCTCA<br>CCATCAGCAGCCTGCAGCCTGATGATTTTGCAACTTATTACTGCCAACAGTATAA<br>TAGTTATTCATTCACTTTCGGCCCTGGGACCAAAGTGGATATCAAG |
| 15175 VH | 86 | CAGGTCCAGCTGGTGCAATCTGGGGCTGAGGTGAAGAAGCCTGGGGCCTCAGTGA<br>AGGTCTCCTGCAAGGCTGCTGGATACACCTTAACCGGCTACTATATGCACTGGGT<br>GCGACAGGCCCCTGGACAAGGCCTTGAGTGGATGGGACGGATCAACCCTAACAGT<br>GGTGGCTCAAACAATGCACAGAAGTTTCAGGGCAGGGTCACCATGACCAGGGACA<br>CGTCCATCAGCACAGCCTACATGGAGCTGAGCAGGCTGAGATCTGACGACACGGC<br>CGTGTATTACTGTGCGAGAGAGGGTCCCCTGTATAGCAGTGGCTGGTACGAGGGT<br>GCTTTTGATATCTGGGGCCAAGGGACAATGGTCACCGTCTCGAGT |
| 15175 VL | 87 | GAAATTGTGATGACGCAGTCTCCTTCCACCCTGTCTGCATCTGTAGGAGACAGAG<br>TCACCATCACTTGCCGGGCCAGTCAGAGTATTAGTAGTTGGTTGGCCTGGTATCA<br>GCAGAAACCAGGGAAAGCCCCTAAGCTCCTGATCTATAAGGCGTCTAGTTTAGAA<br>AGTGGGGTCCCATCAAGGTTCAGCGGCAGTGGATCTGGGACAGAATTCACTCTCA<br>CCATCAGCAGCCTGCAGCCTGATGATTTTGCAACTTATTACTGCCAACAGTATAA<br>TAGTTATTCTCCGGGGCTCACTTTCGGCGGAGGGACCAAGGTGGAGATCAAG |
| 15260 VH | 96 | CAGATGCAGCTACAGCAGTCAGGTCCAGGACTGGTGAAGCCCTCGCAGACCCTCT<br>CACTCACCTGTGCCATCTCCGGGGACAGTGTCTCTAGCAACAGTGCTGCTTGGAA<br>CTGGATCAGGCAGTCCCCATCGAGAGGCCTTGAGTGGCTGGGAAGGACATACTAC<br>AGGTCCAAGTGGTATTCTGCTTTTGCAGTATCTGTGAAAAGTCGAATAACCATCA<br>ACCCAGACACATCCAAGAACCAGTTCTCCCTGCAGCTGAACTCTGTGACTCCCGA<br>GGACACGGCTGTGTATTACTGTGCAAGAGAGGGTAGCAGTGGCTGGTACGGATAC<br>GTCCACCACTGGGGCCAGGGCACCCTGGTCACCGTCTCGAGT |
| 15260 VL | 97 | GAAATTGTGTTGACGCAGTCTCCAGCTTCCCTGTCTGTATCTCTGGGAGAAACTG<br>TCACCATCGAATGTCGAGCAAGTGAGGACATTTACAATGGTTTAGCATGGTATCA<br>GCAGAAGCCAGGGAAATCTCCTCAGCTCCTGATCTATAATGCAAATAGCTTGCAT<br>ACTGGGGTCCCATCACGGTTCAGTGGCAGTGGATCTGGTACACAGTATTCTCTCA<br>AGATAAACAGCCTGCAATCTGAAGATGTCGCAAGTTATTTCTGTCAACAGTATTA<br>CGATTATCCTCCGACGTTCGGCCAAGGGACCAAGGTGGAAATCAAA |
| 15284 VH | 106 | CAGGTGCAGCTGCAGGAGTCGGGCCCAGGACTGGTGAAGCCTTCGGAGACCCTGT<br>CCCTCACCTGCACTGTCTCTGGTGGCTCCTTCAGCAGTAGTAGTTACTACTGGGG<br>CTGGATCCGCCAGCCCCCTGGGAAGGGGCTGGAGTGGATTGGGATCTTCTATTAT<br>AGTGGGACCACCTACTACAACCCGTCCCTCAAGAGTCGAGTCACCATATCCGCAC<br>ACACGTCCAAGAGCCAGTTCTCCCTGAAGCTGAGCTCTGTGACCGCCGCAGACAC<br>GGCTGTGTATTACTGTGCGAGAGGGGGAGAATATTTTGACCGGTTACTCCCCTTT<br>GACTACTGGGGCCAGGGAACCCTGGTCACCGTCTCGAGT |
| 15284 VL | 107 | GAAATTGTGATGACGCAGTCTCCATCCTTCCTGTCTGCATCTGTAGGAGACAGAG<br>TCACCATCACTTGCCGGGCCAGTCAGGGCATTAGCAGTTATTTAGCCTGGTATCA<br>GCAAAAACCAGGGAAAGCCCCTAAGCTCCTGATCTATGCTGCATCCACTTTGGAA<br>AGTGGGGTCCCATCAAGGTTCAGCGGCAGTGGATCTGGGACAGAATTCACTCTCA<br>CAATCAGCAGCCTGCAGCCTGAAGATTTTGCAACTTATTACTGTCAACAGCTTAA<br>TAGTTACCCATTCACTTTCGGCCCTGGGACCAAAGTGGATATCAAG |
| 15299 VH | 116 | CAGGTGCAGCTGGTGGAGTCTGGGGGAGGCTTGGTACAGCCGGGGGGGTCCCTGA<br>GACTCTCCTGTACAGCCTCTGGATTCACCTTTAGCAGCTATGCCATGAGCTGGGT<br>CCGCCAGGCTCCAGGGAAGGGGCTGGAGTGGGTCTCAGCTATTGGTGGTAGTGGT<br>GGTAGCACATACTACGCAGACTCCGTGAAGGGCCGGTTCACCATCTCCAGAGACA<br>ATTCCAAGAACACGCTGTATCTGCAAATGAACAGCCTGAGAGCCGAGGACACGGC<br>CGTATATTACTGTGTGAAAGATGGGGCAGGAGGCTTTGACTACTGGGGCCAGGGA<br>ACCCTGGTCACCGTCTCGAGT |
| 15299 VL | 117 | GATATTGTGATGACGCAGTCTTCATCCTCCCTGTCTGCATCTGTAGGAGACAGAG<br>TCACCATCACTTGCCGGGCAAGTCAGGGCATTATAAATCATTTAGGCTGGTATCA<br>GCATAAACCAGGGAAAGCCCCTAATCGCCTAATCTATGCTGCATCCAGTTTGCAA<br>AGTGGGGTCCCATCAAGGTTCAGCGGCAGTGGATCTGGGACAGAATTCACTCTCA<br>CAATCAGCAGCCTGCAGCCTGAAGATTTTGCAACTTATTACTGTCTACGGCATAA<br>TAGTTACCCTCCGACGTTCGGCCAAGGGACCAAGGTGGAAATCAAG |
| 15353 VH | 126 | CAGGTGCAGCTACAGCAGTCGGGCCCAGGACTGGTGAAGCCTTCACAGACCCTGT<br>CCCTCACCTGCACTGTCTCTGGTGGCTCCATCAACAGTGGTGGTCACTACTGGAG<br>CTGGATCCGCCAGCACCCAGGGAGGGGCCTGGAGTGGATTGGGTACATCTATTAC<br>AGTGGGAGCATCTACTACAACCCGTCCCTCAAGAGTCGACTTACCATATCAGTAG<br>ACACGTCTAAGAACCAGTTCTCCCTGAAGCTGAGCTCTGTGACTGCCGCGGACAC<br>GGCCGTGTATTACTGTGCGAGTTATTACTATGCCAGTAGTGGTGATGCTTTTGAT<br>ATCTGGGGCCAAGGGACAATGGTCACCGTCTCGAGT |
| 15353 VL | 127 | GAAACGACACTCACGCAGTCTCCAGCCACCCTGTCTTTGTCTCCAGGGGAAAGAG<br>CCACCCTCTCCTGCAGGGCCAGTCAGAGTGTTAGCAGCTACTTAGCCTGGTACCA |

TABLE 9-continued

| | | |
|---|---|---|
| DNA sequences of variable domains of anti-TIM-3 binning antibodies | | |

| Ab | SEQ ID NO: | Sequence (5' to 3') |
|---|---|---|
| | | ACAGAAACCTGGCCAGGCTCCCAGGCTCCTCATCTATGATGCATCCAACAGGGCC<br>ACTGGCATCCCAGCCAGGTTCAGTGGCAGTGGGTCTGGGACAGACTTCACTCTCA<br>CCATCAGCAGCCTAGAGCCTGAAGATTTTGCAGTTTATTACTGTCAGCAGCGTAG<br>CAACTGGCCTCCGACGTTCGGCCAAGGGACCAAGGTGGAAATCAAA |
| 15354 VH | 136 | CAGGTGCAGCTGCAGGAGTCTGGGGGAGGCTTGGTACAGCCGGGGGGGTCCCTGA<br>GACTCTCCTGTACAGCCTCTGGATTCACCTTTAGTAATTATGCCATGAGCTGGGT<br>CCGCCAGGCTCCAGGGAAGGGGCTGGAGTGGGTCTCAGCTATTAGTGGTCGTGGT<br>GGTAGCACATTCTTCGCAGACTCCGTGAAGGGCCGGTTCACCATCTCCAGAGACA<br>ATTCCAAGAGCACGCTGTATCTGCAAACGAACAGCCTGAGAGCCGAGGACACGGC<br>CGTATATTACTGTGCGAAAGGGGGCCCGTTGTATAACTGGAACGACGGTGATGGT<br>TTTGATATCTGGGGCCAAGGGACCACGGTCACAGTCTCGAGT |
| 15354 VL | 137 | GAAATTGTGTTGACGCAGTCTCCAGCCACCCTGTCTGTGTCTCCAGGGGAAAGAG<br>CCACCCTCTCCTGCAGGGCCAGTCAGAGTGTTAGCAGCAACTTAGCCTGGTACCA<br>GCAGAAACCTGGCCAGGCTCCCAGGCTCCTCATCTATGGTGCATCCACCAGGGCC<br>ACTGGTATCCCAGCCAGGTTCAGTGGCACTGGGTCTGGGACAGAGTTCACTCTCA<br>CCATCAGCAGCCTGCAGTCTGAAGATTTTGCACTTTATTACTGTCAGCAGTATGA<br>TAACTGGCCTCCGTGGACGTTCGGCCAAGGGACCAAGGTGGAAATCAAA |
| 17244 VH | 146 | CAGGTGCAGCTGCAGGAGTCTGGGGGAGGCTTGGTCAAGCCTGGAGGGTCCCTGA<br>GACTCTCCTGTGCAGCCTCTGGATTCACCTTCAGTGACTACTACATGACCTGGAT<br>CCGCCAGGCTCCAGGGAAGGGGCTGGAGTGGATTTCATACATTAGTGGTGGTGGT<br>GGTTCCATATACTACGCAGACTCTGTGAAGGGCCGATTCACCATCTCCAGGGACA<br>ACGCCAAGAACTCACTGTATCTGCAAATGAACAGCCTGAGAGCCGAGGACACGGC<br>CGTTTATTTCTGTGCGAGAGGGAACTGGGGATCGGCGGCTCTTGATATCTGGGGC<br>CAAGGGACAATGGTCACGGTCTCGAGT |
| 17244 VL | 147 | GAAATTGTGTTGACGCAGTCTCCATCCTCACTGTCTGCATCTGTAGGAGACAGAG<br>TCACCATCACTTGTCGGGCGAGTCAGGGCATTAACAATTATTTAGCCTGGTTTCA<br>GCAGAAACCAGGGAGAGCCCCTAAGTCCCTGATCTATGCTGCATCCAGTTTGCAA<br>AGTGGGGTCCCATCGAAGTTCAGCGGCAGTGGATCTGGGACAGATTTCACTCTCA<br>CCATCAGCAGCCTGCAGCCTGAAGATTTTGCAACTTATTACTGCCAACAGTATAA<br>TAGTTACCCTCCAACTCTCGGCCCTGGGACCAACGTGGATATCAAA |
| 17245 VH | 156 | CAGGTGCAGCTGGTGGAGTCTGGGGGAGGCTTGGTACAGCCGGGGGGGTCCCTGA<br>GACTCTCCTGTACAGCCTCTGGATTCACCTTTAGCAGCTATGCCATGAGCTGGGT<br>CCGCCAGGCTCCAGGGAAGGGGCTGGAGTGGGTCTCAGCTATTGGTGGTAGTGGT<br>GGTAGCGCATACTACGCAGACTCCGTGAAGGGCCGGTTCACCATCTCCAGAGACA<br>ATTCCAAGAACACGCTGTATCTGCAAATGAACAGCCTGAGAGCCGAGGACACGGC<br>CGTATATTACTGTGTGAAAGATGGGGCAGGAGGCTTTGACTACTGGGGCCAGGGC<br>ACCCTGGTCACCGTCTCGAGT |
| 17245 VL | 157 | GACATCCAGTTGACCCAGTCCCCATCCTCCCTGTCTGCATCTGTAGGAGACAGAG<br>TCACCATCACTTGCCGGGCAAGTCAGGGCATTAGAAATCATTTAGGCTGGTATCA<br>GCAGAAACCAGGGAAAGCCCCTAAGCGCCTAATCTATGCTGCATCCAGTTTGCAA<br>AGTGGGGTCCCATCAAGGTTCAGCGGCAGTGGATCTGGGACAGAATTCACTCTCA<br>CAATCAGCAGCCTGCAGCCTGAAGATTTTGCAACTTATTACTGTCTACAGCATAA<br>TAGTTACCCTCCGACGTTCGGCCAAGGGACCAAGGTGGAAATCAAG |

Table 10 shows the deduced heavy and light chain variable domain protein sequences of anti-TIM-3 antibodies 50 used for epitope binning. CDRs are shown bolded and italicized.

TABLE 10

| | | |
|---|---|---|
| Protein sequences of variable domains of anti-TIM-3 binning antibodies | | |

| Ab | SEQ ID NO: | Sequence (N-terminal to C-terminal) |
|---|---|---|
| 20131 VH | 28 | QVQLQQSGGGLVQPGGSLRLSCAAS*GFTLSSYA*MSWVRQAPGKGLEWVSG*ISGS<br>GGST*YNADSVKGRFTISRDNSKNTLFLQMNSLRAEDTAVYY*CAKIFGSYYFDYW*<br>GQGTLVTVSS |
| 20131 VL | 29 | EIVMTQSPDSLAVSLGERATINCKSS*QSVLYSSNNKNY*LAWYQQKPGQPPKLLI<br>Y*WTS*TRESGVPNRFSGSGSGTDFTLTISSLQAEDVAVYYC*QQYYSGPPTF*FGQGT<br>KVEIK |

TABLE 10-continued

| Protein sequences of variable domains of anti-TIM-3 binning antibodies |

| Ab | SEQ ID NO: | Sequence (N-terminal to C-terminal) |
| --- | --- | --- |
| 20293 VH | 38 | QVQLQESGPGLVKPSQTLSLTCTVSGGSISSGGYYWSWIRQHPGKGLEWIGYIY<br>YSGSIYYNPSLKSRVTISVDTSKNQFYLKLSSVTAADTAVYYCASLMVWGVMGD<br>YWGQGTLVTVSS |
| 20293 VL | 39 | EIVLTQSPATLSLSPGERATLSCRASQSVSSYLAWYQQKPGQAPRLLIYDASNR<br>ATGIPARFSGSGSGTDFTLTISSLEPEDFAVYYCQQRSDWPPTFGQGTKVEIK |
| 15105 VH | 48 | QVTLKEWGAGLLRPSETLSLTCAVYGGSFSGYYWSWIRQPPGKGLEWIGEINHS<br>GSTNYNPSLKSRVTISVDATKKQFSLKLTSVTAADTAVYYCARYWELPDYWGQG<br>TLVTVSS |
| 15105 VL | 49 | DIQLTQSPSSLSASVGDRVTITCRASQGIRNDLGWYQQKPGKAPKRLIYAASSL<br>QSGVPSRFSGSGSGTEFTLTISSLQPEDFATYYCLQHNSYPPTFGQGTKVEIK |
| 15107 VH | 58 | QMQLVQWGAGLLKPSETLSLTCAVYGGSFSGYYWSWIRQPPGKGLEWIGEINHS<br>GSTNYNPSLKSRVTMSVDTSKHQFSLKLSSVTAADTAVYYCARWWELPDYWGQG<br>TLVTVSS |
| 15107 VL | 59 | EIVLTQSPSSLSASVGDRVTITCRASQGIRNDLGWYQQKPGKAPKRLIYAASSL<br>QSGVPSRFSGSGSGTEFTLTISSLQPEDFATYYCLQHNSYPWTFGQGTKVEIK |
| 15109 VH | 68 | QMQLVQWGAGLLKPSETLSLTCAVYGGSFSGYYWSWIRQPPGKGLEWIGEINHS<br>GSTNYNPSLKSRVTISVDTSKNQFSLKLSSVTAADTAVYYCARFYYAPNFDYWG<br>QGTLVTVSS |
| 15109 VL | 69 | EIVLTQSPTLSASVGDRVTITCRASQSISSWLAWYQQKPGTAPKLLIYKASSL<br>ESGVPSRFSGSGSGTEFTLTISSLQPDDFATYYCQQYNSYSTFGGGTKVEIK |
| 15174 VH | 78 | QVQLQQSGPGLVKPSETLSLTCTVSGGSISSSNYYWGWIRQPPGKGLEWIGSIY<br>YSGNTYYNPSLKSRVTISVDTSKNQFSLKLSSVTAADTAVYYCARQTVAGPLFD<br>YWGQGTLVTVSS |
| 15174 VL | 79 | EIVMTQSPTLSASVGDRVTITCRASQSISSWLAWYQQKPGKAPKVLIYKASSL<br>ESGVPSRFSGSGSGTELTLTISSLQPDDFATYYCQQYNSYSFTFGPGTKVDIK |
| 15175 VH | 88 | QVQLVQSGAEVKKPGASVKVSCKAAGYTLTGYYMHWVRQAPGQGLEWMGRINPN<br>SGGSNNAQKFQGRVTMTRDTSISTAYMELSRLRSDDTAVYYCAREGPLYSSGWY<br>EGAFDIWGQGTMVTVSS |
| 15175 VL | 89 | EIVMTQSPTLSASVGDRVTITCRASQSISSWLAWYQQKPGKAPKLLIYKASSL<br>ESGVPSRFSGSGSGTEFTLTISSLQPDDFATYYCQQYNSYSPGLTFGGGTKVEI<br>K |
| 15260 VH | 98 | QMQLQQSGPGLVKPSQTLSLTCAISGDSVSSNSAAWNWIRQSPSRGLEWLGRTY<br>YRSKWYSAFAVSVKSRITINPDTSKNQFSLQLNSVTPEDTAVYYCAREGSSGWY<br>GYVHHWGQGTLVTVSS |
| 15260 VL | 99 | EIVLTQSPASLSVSLGETVTIECRASEDIYNGLAWYQQKPGKSPQLLIYNANSL<br>HTGVPSRFSGSGSGTQYSLKINSLQSEDVASYFCQQYYDYPPTFGQGTKVEIK |
| 15284 VH | 108 | QVQLQESGPGLVKPSETLSLTCTVSGGSFSSSSYYWGWIRQPPGKGLEWIGIFY<br>YSGTTYYNPSLKSRVTISAHTSKSQFSLKLSSVTAADTAVYYCARGGEYFDRLL<br>PFDYWGQGTLVTVSS |
| 15284 VL | 109 | EIVMTQSPSFLSASVGDRVTITCRASQGISSYLAWYQQKPGKAPKLLIYAASTL<br>ESGVPSRFSGSGSGTEFTLTISSLQPEDFATYYCQQLNSYPFTFGPGTKVDIK |
| 15299 VH | 118 | QVQLVESGGGLVQPGGSLRLSCTASGFTFSSYAMSWVRQAPGKGLEWVSAIGGS<br>GGSTYYADSVKGRFTISRDNSKNTLYLQMNSLRAEDTAVYYCVKDGAGGFDYWG<br>QGTLVTVSS |
| 15299 VL | 119 | DIVMTQSSSSLSASVGDRVTITCRASQGIINHLGWYQHKPGKAPNRLIYAASSL<br>QSGVPSRFSGSGSGTEFTLTISSLQPEDFATYYCLRHNSYPPTFGQGTKVEIK |
| 15353 VH | 128 | QVQLQQSGPGLVKPSQTLSLTCTVSGGSINSGGHYWSWIRQHPGRGLEWIGYIY<br>YSGSIYYNPSLKSRLTISVDTSKNQFSLKLSSVTAADTAVYYCASYYYASSGDA<br>FDIWGQGTMVTVSS |
| 15353 VL | 129 | ETTLTQSPATLSLSPGERATLSCRASQSVSSYLAWYQQKPGQAPRLLIYDASNR<br>ATGIPARFSGSGSGTDFTLTISSLEPEDFAVYYCQQRSNWPPTFGQGTKVEIK |
| 15354 VH | 138 | QVQLQESGGGLVQPGGSLRLSCTASGFTFSNYAMSWVRQAPGKGLEWVSAISGR<br>GGSTFFADSVKGRFTISRDNSKSTLYLQTNSLRAEDTAVYYCAKGGPLYNWNDG<br>DGFDIWGQGTTVTVSS |

TABLE 10-continued

Protein sequences of variable domains of anti-TIM-3 binning antibodies

| Ab | SEQ ID NO: | Sequence (N-terminal to C-terminal) |
|---|---|---|
| 15354 VL | 139 | EIVLTQSPATLSVSPGERATLSCRAS*QSVSSN*LAWYQQKPGQAPRLLIY*GAS*TR ATGIPARFSGTGSGTEFTLTISSLQSEDFALYY*CQQYDNWPPWTF*GQGTKVEIK |
| 17244 VH | 148 | QVQLQESGGGLVKPGGSLRLSCAAS*GFTFSDYY*MTWIRQAPGKGLEW*ISYISGG GGSI*YYADSVKGRFTISRDNAKNSLYLQMNSLRAEDTAVYF*CARGNWGSAALDI W*GQGTMVTVSS |
| 17244 VL | 149 | EIVLTQSPSSLSASVGDRVTITCRAS*QGINNY*LAWFQQKPGRAPKSLIY*AAS*SL QSGVPSKFSGSGSGTDFTLTISSLQPEDFATYY*CQQYNSYPPTL*GPTNVDIK |
| 17245 VH | 158 | QVQLVESGGGLVQPGGSLRLSCTAS*GFTFSSYA*MSWVRQAPGKGLEWVSA*IGGS GGSA*YYADSVKGRFTISRDNSKNTLYLQMNSLRAEDTAVYY*CVKDGAGGFDYW*G QGTLVTVSS |
| 17245 VL | 159 | DIQLTQSPSSLSASVGDRVTITCRAS*QGIRNH*LGWYQQKPGKAPKRLIY*AAS*SL QSGVPSRFSGSGSGTEFTLTISSLQPEDFATYY*CLQHNSYPPTF*GQGTKVEIK |

Table 11 shows the CDRs of anti-TIM-3 binning antibodies. SEQ ID NOs for the CDRs are shown under each sequence. The CDR sequences herein were determined according to the IMGT® definitions for CDR1 and CDR2. For heavy and light chain CDR3, the definitions herein include one extra amino acid residue upstream of the IMGT-CDR3 (Cys) and one extra amino acid residue downstream (Trp for VH CDR3, Phe for VL CDR3).

TABLE 11

Protein sequences of CDRs of anti-TIM-3 binning antibodies

| Antibody | HCDR1 | HCDR2 | HCDR3 | LCDR1 | LCDR2 | LCDR3 |
|---|---|---|---|---|---|---|
| 20131 | GFTLSSYA 30 | ISGSGGST 31 | CAKIFGSYYFD YW 32 | QSVLYSSNNKNY 33 | WTS 34 | CQQYYSGPPTF 35 |
| 20293 | GGSISSGGYY 40 | IYYSGSI 41 | CASLMVWGVMG DYW 42 | QSVSSY 43 | DAS 44 | CQQRSDWPPTF 45 |
| 15105 | GGSFSGYY 50 | INHSGST 51 | CARYWELPDYW 52 | QGIRND 53 | AAS 54 | CLQHNSYPPTF 55 |
| 15107 | GGSFSGYY 60 | INHSGST 61 | CARWWELPDYW 62 | QGIRND 63 | AAS 64 | CLQHNSYPWTF 65 |
| 15109 | GGSFSGYY 70 | INHSGST 71 | CARFYYAPNFD YW 72 | QSISSW 73 | KAS 74 | CQQYNSYSTF 75 |
| 15174 | GGSISSSNYY 80 | IYYSGNT 81 | CARQTVAGPLF DYW 82 | QSISSW 83 | KAS 84 | CQQYNSYSFTF 85 |
| 15175 | GYTLTGYY 90 | INPNSGGS 91 | CAREGPLYSSG WYEGAFDIW 92 | QSISSW 93 | KAS 94 | CQQYNSYSPGL TF 95 |
| 15260 | GDSVSSNSAA 100 | TYYRSKWYS 101 | CAREGSSGWYG YVHHW 102 | EDIYNG 103 | NAN 104 | CQQYYDYPPTF 105 |
| 15284 | GGSFSSSSYY 110 | FYYSGTT 111 | CARGGEYFDRL LPFDYW 112 | QGISSY 113 | AAS 114 | CQQLNSYPFTF 115 |
| 15299 | GFTFSSYA 120 | IGGSGGST 121 | CVKDGAGGFDY W 122 | QGIINH 123 | AAS 124 | CLRHNSYPPTF 125 |
| 15353 | GGSINSGGHY 130 | IYYSGSI 131 | CASYYYASSGD AFDIW 132 | QSVSSY 133 | DAS 134 | CQQRSNWPPTF 135 |

TABLE 11-continued

| Protein sequences of CDRs of anti-TIM-3 binning antibodies | | | | | |
|---|---|---|---|---|---|
| Antibody | HCDR1 | HCDR2 | HCDR3 | LCDR1 | LCDR2 | LCDR3 |
| 15354 | GFTFSNYA 140 | ISGRGGST 141 | CAKGGPLYNWN DGDGFDIW 142 | QSVSSN 143 | GAS 144 | CQQYDNWPPWT F 145 |
| 17244 | GFTFSDYY 150 | ISGGGGSI 151 | CARGNWGSAAL DIW 152 | QGINNY 153 | AAS 154 | CQQYNSYPPTL 155 |
| 17245 | GFTFSSYA 160 | IGGSGGSA 161 | CVKDGAGGFDY W 162 | QGIRNH 163 | AAS 164 | CLQHNSYPPTF 165 |

Table 12 shows the DNA sequences encoding the heavy and light chain variable domains of additional anti-TIM-3 antibodies identified as functional antibodies. The sequences for functional antibodies 20131 and 20293 are shown in Table 9 above.

TABLE 12

| DNA sequences of variable domains of additional functional anti-TIM-3 antibodies | | |
|---|---|---|
| Ab | SEQ ID NO: | Sequence (5' to 3') |
| 19324 VH | 166 | CAGATGCAGCTACAGCAGTCTGGGGGAGGCTTGGTACAGCCGGGGGGGTCCCTG AGACTCTCCTGTGCAGCCTCTGGATTCACCGTTAGCAGCTATGCCATGAGCTGG GTCCGCCAGGCTCTAGGGAAGGGGCTGGAGTGGGTCTCAGGTATTAGTGGTAGT GGTGGTAGCACATACTACGCAGACTCCGTGAAGGGCCGGTTCACCATCTCCAGA GACAATTCCAAGAATACGCTGTATCTGCAAATGAACAGCCTGAGAGCCGAGGAC ACGGCCGTATATTACTGTGCGAAGATAGTGGGAGCTACCCACTTTGACTACTGG GGCCAGGGAACCCTGGTCACGGTCTCGAGT |
| 19324 VL | 167 | GAAATTGTGATGACACAGTCTCCAGACTCCCTGGCTGTGTCTCTGGGCGAGAGG GCCACCATCAACTGCAAGTCCAGCCAGAGTGTTTTATACAGCTCCAACAATAAG AACTACTTAGCTTGGTACCAGCAGAAACCAGGACAGCCTCCTAAGCTGCTCATT TACTGGGCATCTACCCGGGAATCCGGGGTCCCTGACCGATTCAGTGGCAGCGGG TCTGGGACAGATTTCACTCTCACCATCAGCAGCCTGCAGGCTGAAGATGTGGCA GTTTATTACTGTCAGCAATATTATAGTGGTCCGATCACCTTCGGCCAAGGGACA CGACTGGAGATTAAG |
| 19416 VH | 176 | CAGGTGCAGCTGGTGGAGTCGGGCCCAGGACTGGTGAAGCCTTCACAGACCCTG TCCCTCACCTGCACTGTCTCTGGTGGCTCCATCAACAGTGGTGGTTACTACTGG AGCTGGATCCGCCAGCACCCAGGGAAGGGCCTGGAGTGGATTGGGTACATCTAT TACAGTGGGAGCATCTACTACAACCCGTCCCTCAGGAGTCGACTTACCATATCA GTAGACACGTCTAAGAACCAGTTCTCCCTGAAGCTGAGCTCTGTGACTGCCGCG GACACGGCCGTTTATTACTGTGCGACTCCTTATTACTATGGTTCGGGGAGTTAT GGGGACTACTGGGGCCAGGGCACCCTGGTCACTGTCTCGAGT |
| 19416 VL | 177 | GACATCCAGATGACCCAGTCTCCAGCCACCCTGTCTTTGTCTCCAGGGGAAAGA GCCACCCTCTCCTGCAGGGCCAGTCAGAGTGTTAACAACTACTTAGCCTGGTAC CAACAGAAACCTGGCCAGGCTCCCAGGCTCCTCATCTATGATGCATCCAACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAG CGTAGCAACTGGCCCATCACCTTCGGCCAAGGGACACGACTGGAGATTAAA |
| 19568 VH | 186 | CAGATGCAGCTGCAGGAGTCGGGCCCAGGACTGGTGAAGCCTTCTCAGACCCTG TCCCTCACCTGCACTGTGTCTGGTGGCTCCATCAGCAGTGTTGGTTACTACTGG AACTGGATCCGCCAGCACCCAGGGAAGGGCCTGGAGTTCATTGGGTACATCTAT TACAGTGGGAGCATCTACTACAATCCGTCCCTCAAGAGTCGAGTTACCATATCC GTAGACACGTCTAAGAACCAGTTCTCCCTGAAGCTGAGCTCTGTGACTGCCGCG GACACGGCCCTATATTACTGTGCGAGCGTCGGTATAGTGGGAGCCTCCTACTTT GAGTACTGGGGCCAGGGAACCCTGGTCACAGTCTCGAGT |
| 19568 VL | 187 | GAAATTGTGATGACACAGTCTCCAGCCACCCTGTCTTTGTCTCCAGGGGAAAGA GCCACCCTCTCCTGCAGGGCCAGTCAGAGTGTTAGCAGCTACTTAGCCTGGTAC CAACAGAAACCTGGCCAGGCTCCCAGGCTCCTCATCTATGATGCATCCAACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAG CGTAGCAACTGGCCTATCACCTTCGGCCAAGGGACACGACTGGAGATCAAG |

TABLE 12-continued

DNA sequences of variable domains of additional functional anti-TIM-3 antibodies

| Ab | SEQ ID NO: | Sequence (5' to 3') |
|---|---|---|
| 20185 VH | 196 | CAGGTGCAGCTGGTGGAGTCTGGGGGAGGCTTGGTTCGGCCTGGGGGGTCCCTG AGACTCTCCTGTGCAGTCTCTGGATTCACCTTTAGCAGCTATGCCATGAGCTGG GTCCGCCAGGCTCCAGGGAAGGGGCTGGAGTGGGTCTCAGGTATTAGTGGTAGT GGTGGTAGCACATACAACGCAGACTCCGTGAAGGGCCGGTTCACCATCTCCAGA GACAATTCCAAGAACACGCTGTATCTTCAAATGAACAGCCTGAGAGCCGAGGAC ACGGCCGTATATTACTGTGCGAAAATTTTTGGGTCCTACTACTTTGACTACTGG GGCCAGGGAACCCTGGTCACCGTCTCGAGT |
| 20185 VL | 197 | GAAATTGTGATGACACAGTCTCCAGACTCCCTGGCTGTGTCTCTGGGCGAGAGG GCCACCATCAACTGCAAGTCCAGCCAGAGTGTTTTATACAGCTCCAATAATAAG AACTACTTAGCTTGGTACCAGCAGAAATCAGGACAGCCTCCTAAGCTGCTCATT TACTGGGCATCTACCCGGGAATCCGGGGTCCCTGACCGATTCAGTGGCAGCGGG TCTGGGACAGATTTCACTCTCACCATCAGCAGCCTGCAGGCTGAAGATGTGGCA GTTTATTACTGTCAGCAATATTATAGTGGTCCACCGACGTTCGGCCAAGGGACC AAGGTGGAAATCAAA |
| 20300 VH | 206 | CAGGTCCAGCTACAGCAGTCTGGGGGAGGCTTGGTTCATCCTGGGGGGTCCCTA AGACTCTCCTGTGCAGCCTCTGGATTCACCGTTGACACCTATGCCATGACCTGG GTCCGCCAGGCTCCAGGGAAGGGGCTGGAGTGGGTCTCAGGTATTAGCGGTAGT GGTGGTAGCACATACTACGCAGACTCCGTGAAGGGCCGGTTCACCATCTCCAGA GACAACTCCAAGAACACGCTGTATCTGCAAATGAACAGCCTGAGAGACGAGGAC ACGGCCGTATATTACTGTGCGAAGATAGTGGGAGTTACCCACTTTGACTACTGG GGCCAGGGCACCCTGGTCACGGTCTCGAGT |
| 20300 VL | 207 | GAAATTGTGATGACGCAGTCTCCAGACTCCCTGGCTGTGTCTCTGGGCGAGAGG GCCACCATCAACTGCAAGTCCAGCCAGAGTGTTTTATACAGGTCCAACAATAAG AACTATTTAGCTTGGTACCAGCAGAAACCAGGACAGCCTCCTAAGCTGCTCATT TACTGGGCATCTACCCGGGAATCCGGGGTCCCTGACCGATTCAGTGGCAGCGGG TCTGGGACAGATTTCACTCTCACCATCAGCAGCCTGCAGGCTGAAGATGTGGCA GTTTATTACTGTCAGCAATATTATAGTGGTCCGATCACCTTCGGCCAAGGGACA CGACTGGAGATTAAG |
| 20362 VH | 216 | CAGGTCACCTTGAAGGAGTCGGGCCCAGGACTGGTGAAGCCTTCACAGACCCTG TCCCTCACCTGCACTGTCTCTGGTGGCTCCATCAGCAGTGGTGGTCATTACTGG AGCTGGATCCGCCAGCACCCAGGGAAGGGCCTGGAGTGGATTGGGTACATCTCT TACAGTGGGAGCACCTACTACAACCCGTCCCTCAAGAGTCGACTTACCATATCA GTAGACACGTCTAAGAACCAGTTCTCCCTGAAGCTGAGCTCTGTGACTGCCGCG GACACGGCCGTGTATTACTGTGCGACCGCGTATTACGATATTTTTGACTGGTTAC CCTTTTGACTACTGGGGCCAGGGAACCCTGGTCACGGTCTCGAGT |
| 20362 VL | 217 | GAAATTGTGATGACACAGTCTCCAGCCACCCTGTCTTTGTCTCCAGGGGAAAGA GCCACCCTCTCCTGCAGGGCCAGTCAGAGTGTTAGCAGCTACTTAGCCTGGTAC CAACAGAAACCTGGCCAGGCTCCCAGGCTCCTCATCTATGATGCATCCGACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAG CGTAGCAACTGGCCGATCACCTTCGGCCAAGGGACACGACTGGAGATCAAG |
| 20621 VH | 226 | CAGGTGCAGCTACAGCAGTCGGGCCCAGGACTGGTGAAGCCTTCACAGACCCTG TCCCTCACCTGCACTGTCTCTGGTGGCTCCATCAGCAGTGGTGGTTACTACTGG AGCTGGATCCGCCAGCACCCAGGGAAGGGCCTGGAGTGGATTGGGTACATCTCT TATAGTGGGAGTATCTACTACAACCCGTCCCTCAAGAGTCGAGTTACCATATCA GTAGACACGTCTAAGAACCAGTTCTCCCTGAAGCTGAGCTCTGTGACTGCCACG GACACGGCCGTGTATTACTGTGCGACCGCGTATTACGATCTTTTTGACTGGTTAC CCTTTTGACTACTGGGGCCAGGGAACCCTGGTCACGGTCTCGAGT |
| 20621 VL | 227 | GAAATTGTGATGACGCAGTCTCCAGCCACCCTGTCTTTGTCTCCAGGGGAAAGA GCCACCCTCTCCTGCAGGGCCAGTCAGAGTGTTAGCAGCTACTTAGCCTGGTAC CAACAGAAACCTGGCCAGGCTCCCAGGCTCCTCATCTATGATGCATCCAACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAG CGTAGCAACTGGCCGATCACCTTCGGCCAAGGGACACGACTGGAGATTAAG |

Table 13 shows the deduced protein sequences of the heavy and light chain variable domains of additional anti-TIM-3 antibodies identified as functional antibodies. CDRs are shown in bolded and italicized. The sequences for functional antibodies 20131 and 20293 are shown in Table 10 above.

TABLE 13

| Protein sequences of variable domains of additional functional anti-TIM-3 antibodies | | |
|---|---|---|
| Ab | SEQ ID NO: | Sequence (N-terminal to C-terminal) |
| 19324 VH | 168 | QMQLQQSGGGLVQPGGSLRLSCAASGFTVSSYAMSWVRQALGKGLEWVSGISGS GGSTYYADSVKGRFTISRDNSKNTLYLQMNSLRAEDTAVYYCAKIVGATHFDYW GQGTLVTVSS |
| 19324 VL | 169 | EIVMTQSPDSLAVSLGERATINCKSSQSVLYSSNNKNYLAWYQQKPGQPPKLLI YWASTRESGVPDRFSGSGSGTDFTLTISSLQAEDVAVYYCQQYYSGPITFGQGT RLEIK |
| 19416 VH | 178 | QVQLVESGPGLVKPSQTLSLTCTVSGGSINSGGYYWSWIRQHPGKGLEWIGYIY YSGSIYYNPSLRSRLTISVDTSKNQFSLKLSSVTAADTAVYYCATPYYYGSGSY GDYWGQGTLVTVSS |
| 19416 VL | 179 | DIQMTQSPATLSLSPGERATLSCRASQSVNNYLAWYQQKPGQAPRLLIYDASNR ATGIPARFSGSGSGTDFTLTISSLEPEDFAVYYCQQRSNWPITFGQGTRLEIK |
| 19568 VH | 188 | QMQLQESGPGLVKPSQTLSLTCTVSGGSISSVGYYWNWIRQHPGKGLEFIGYIY YSGSIYYNPSLKSRVTISVDTSKNQFSLKLSSVTAADTALYYCASVGIVGASYF EYWGQGTLVTVSS |
| 19568 VL | 189 | EIVMTQSPATLSLSPGERATLSCRASQSVSSYLAWYQQKPGQAPRLLIYDASNR ATGIPARFSGSGSGTDFTLTISSLEPEDFAVYYCQQRSNWPITFGQGTRLEIK |
| 20185 VH | 198 | QVQLVESGGGLVRPGGSLRLSCAVSGFTFSSYAMSWVRQAPGKGLEWVSGISGS GGSTYNADSVKGRFTISRDNSKNTLYLQMNSLRAEDTAVYYCAKIFGSYYFDYW GQGTLVTVSS |
| 20185 VL | 199 | EIVMTQSPDSLAVSLGERATINCKSSQSVLYSSNNKNYLAWYQQKSGQPPKLLI YWASTRESGVPDRFSGSGSGTDFTLTISSLQAEDVAVYYCQQYYSGPPTFGQGT KVEIK |
| 20300 VH | 208 | QVQLQQSGGGLVHPGGSLRLSCAASGFTVDTYAMTWVRQAPGKGLEWVSGISGS GGSTYYADSVKGRFTISRDNSKNTLYLQMNSLRDEDTAVYYCAKIVGVTHFDYW GQGTLVTVSS |
| 20300 VL | 209 | EIVMTQSPDSLAVSLGERATINCKSSQSVLYRSNNKNYLAWYQQKPGQPPKLLI YWASTRESGVPDRFSGSGSGTDFTLTISSLQAEDVAVYYCQQYYSGPITFGQGT RLEIK |
| 20362 VH | 218 | QVTLKESGPGLVKPSQTLSLTCTVSGGSISSGGHYWSWIRQHPGKGLEWIGYIS YSGSTYYNPSLKSRLTISVDTSKNQFSLKLSSVTAADTAVYYCATAYYDILTGY PFDYWGQGTLVTVSS |
| 20362 VL | 219 | EIVMTQSPATLSLSPGERATLSCRASQSVSSYLAWYQQKPGQAPRLLIYDASDR ATGIPARFSGSGSGTDFTLTISSLEPEDFAVYYCQQRSNWPITFGQGTRLEIK |
| 20621 VH | 228 | QVQLQQSGPGLVKPSQTLSLTCTVSGGSISSGGYYWSWIRQHPGKGLEWIGYIS YSGSIYYNPSLKSRVTISVDTSKNQFSLKLSSVTATDTAVYYCATAYYDILTGY PFDYWWGQGTLVTVSS |
| 20621_VL | 229 | EIVMTQSPATLSLSPGERATLSCRASQSVSSYLAWYQQKPGQAPRLLIYDASNR ATGIPARFSGSGSGTDFTLTISSLEPEDFAVYYCCQQRSNWPITFGQGTRLEIK |

Table 14 shows the CDRs of additional functional anti-TIM-3 antibodies. SEQ ID NOs for the CDRs are shown under each sequence. The CDR sequences herein were determined according to the IMGT® definitions for CDR1 and CDR2. For heavy and light chain CDR3, the definitions herein include one extra amino acid residue upstream of the IMGT-CDR3 (Cys) and one extra amino acid residue downstream (Trp for VH CDR3, Phe for VL CDR3). The sequences for functional antibodies 20131 and 20293 are shown in Table 11 above.

TABLE 14

| Protein sequences of CDRs of additional functional anti-TIM-3 antibodies | | | | | | |
|---|---|---|---|---|---|---|
| Ab | HCDR1 | HCDR2 | HCDR3 | LCDR1 | LCDR2 | LCDR3 |
| 19324 | GFTVSSYA 170 | ISGSGGST 171 | CAKIVGATHFDYW 172 | QSVLYSSNNKNY 173 | WAS 174 | CQQYYSGPITF 175 |
| 19416 | GGSINSGGYY 180 | IYYSGSI 181 | CATPYYYGSGSYGDY W 182 | QSVNNY 183 | DAS 184 | CQQRSNWPITF 185 |

TABLE 14-continued

Protein sequences of CDRs of additional functional anti-TIM-3 antibodies

| Ab | HCDR1 | HCDR2 | HCDR3 | LCDR1 | LCDR2 | LCDR3 |
|---|---|---|---|---|---|---|
| 19568 | GGSISSVGYY 190 | IYYSGSI 191 | CASVGIVGASYFEYW 192 | QSVSSY 193 | DAS 194 | CQQRSNWPITF 195 |
| 20185 | GFTFSSYA 200 | ISGSGGST 201 | CAKIFGSYYFDYW 202 | QSVLYSSNNKNY 203 | WAS 204 | CQQYYSGPPTF 205 |
| 20300 | GFTVDTYA 210 | ISGSGGST 211 | CAKIVGVTHFDYW 212 | QSVLYRSNNKNY 213 | WAS 214 | CQQYYSGPITF 215 |
| 20362 | GGSISSGGHY 220 | ISYSGST 221 | CATAYYDILTGYPFD YW 222 | QSVSSY 223 | DAS 224 | CQQRSNWPITF 225 |
| 20621 | GGSISSGGYY 230 | ISYSGSI 231 | CATAYYDLLTGYPFD YW 232 | QSVSSY 233 | DAS 234 | CQQRSNWPITF 235 |

Example 2: Kinetic Binding Analysis of Antibodies 15086.15086, 15086.16837, 15086.17145, and 15086.17144

This example demonstrates that the binding affinity of antibodies 15086.15086 (IgG1), 15086.16837 (IgG1 LALA), 15086.17145 (IgG2), and 15086.17144 (IgG4 (S228P)) showed very similar binding affinities with $K_D$ values around 19-23 nM. "IgG1 LALA" refers to the presence of the "LALA" mutations in the heavy chain (L234A/L235A, numbered according to the Eu numbering scheme (Edelman et al., *Proc. Natl. Acad. USA* 63:78-85 (1969)) that are known to reduce effector function of the Fc region of IgG1 antibodies (Armour et al., *Eur J Immunol.* 29(8):2613-24 (1999); Hezareh et al., *J Virol.* 75(24):12161-68 (2001); and Hessel et al., *Nature* 449(7158):101-104 (2007)).

Materials and Methods

The kinetic binding analysis was performed by Surface Plasmon Resonance (SPR), using a Continuous Flow Microspotter (CFM, Wasatch Microfluidics, Salt Lake City, US) combined with an Ibis MX96 SPR instrument (IBIS Technologies, The Netherlands). Surface Plasmon Resonance imaging analysis was performed on G-a-hu-IgG Fc SensEye® SPR sensors (Ssens BV, The Netherlands). Anti-TIM-3 antibodies 15086.15086, 15086.16837, 15086.17145, and 15086.17144 were diluted to 0.15 µg/ml in PBS-T (1×PBS with 0.05% Tween 20, pH 7.4). Antibodies were spotted onto a G-a-hu-IgG Fc SensEye® for 15 minutes using a Continuous Flow Microspotter. After spotting, the SensEye® was positioned in the IBIS MX96 biosensor, and kinetic analysis was performed by applying a so-called kinetic titration series (Karlsson et al., *Anal Biochem.* 349(1):136-47 (2006)), where monomeric human TIM-3 ECD antigen (Acro Biosystems) was injected in increasing concentrations from 2 nM to 100 nM without application of surface regeneration steps after each antigen injection. Antigen association was performed for 5 minutes and antigen dissociation was performed for 45 minutes. The recorded binding responses were fitted to a simple Langmuir 1:1 binding model with Scrubber 2 software for calculation of the on-rate (kon or ka), off-rate (koff or kd) and affinity (KD) constants.

Results

The kinetic measurements performed on the IBIS system showed that antibodies 15086.15086, 15086.16837, 15086.17145, and 15086.17144, in four different isotype formats, all had very similar binding kinetics with KD values in the range of 19-23 nM (Table 15).

TABLE 15

Binding kinetics of antibodies 15086.15086, 15086.16837, 15086.17145, and 15086.1714 to human TIM-3 ECD as measured by Surface Plasmon Resonance (SPR)

| Format/ Subclass | kon (M−1 s−1) | | kon Error | koff s−1) | | koff Error | KD (nM) | | KD Error |
|---|---|---|---|---|---|---|---|---|---|
| 15086. 15086 | 5.06E+05 | ± | 6.E+02 | 1.17E−02 | ± | 8.E−06 | 23 | ± | 3.0E−11 |
| 15086. 16837 | 5.83E+05 | ± | 4.E+02 | 1.11E−02 | ± | 4.E−06 | 19 | ± | 1.0E−11 |
| 15086. 17145 | 5.56E+05 | ± | 4.E+02 | 1.03E−02 | ± | 4.E−06 | 19 | ± | 1.0E−11 |
| 15086. 17144 | 4.96E+05 | ± | 3.E+02 | 9.85E−03 | ± | 4.E−06 | 20 | ± | 2.0E−11 |

Example 3: In Vitro Functional Evaluation of Anti-TIM-3 Antibody

A panel of unique mAbs in the IgG1 subclass were cloned as described above (Example 1) and screened for functional activity at a single concentration (25 ug/ml) in the one-way mixed lymphocyte reaction (MLR) assay. The most functional anti-TIM-3 antibody (15086.15086) was reformatted into the IgG1 LALA (15086.16837), IgG2 (15086.17145) and IgG4 (15086.17144) subclasses.

This example demonstrates in vitro functional activity of the various IgG subclasses of the anti-TIM-3 antibody by inducing dose-dependent cytokine secretion in a one-way MLR assay.

Materials and Methods

In the one-way MLR assay, dendritic cells (DCs) and CD4-positive (CD4+) T-cells isolated from two different healthy donors are co-cultured to induce an alloantigen specific reaction, resulting in cytokine production and T-cell activation/proliferation. Dendritic cells were differentiated from CD14+ monocytes by 6 days of culture with 20 ng/ml granulocyte-macrophage colony-stimulating factor (GM-CSF) and 20 ng/ml interleukin-4 (IL-4) and mixed in a 1:10 ratio with CD4+ T-cells isolated from peripheral blood mononuclear cells (PBMCs) from healthy donor material. After 5 days of culture, supernatants were harvested, and IFN-γ and TNF-α levels were determined using the Meso Scale electrochemiluminescence cytokine assay. This assay uses electrochemiluminescent labels (SULFO-TAG) that are conjugated to detection antibodies. When current is applied to the plate electrodes, light is emitted by the SULFO-TAG label, and light intensity is measured to quantify cytokines in the samples.

Results

Figure 2:
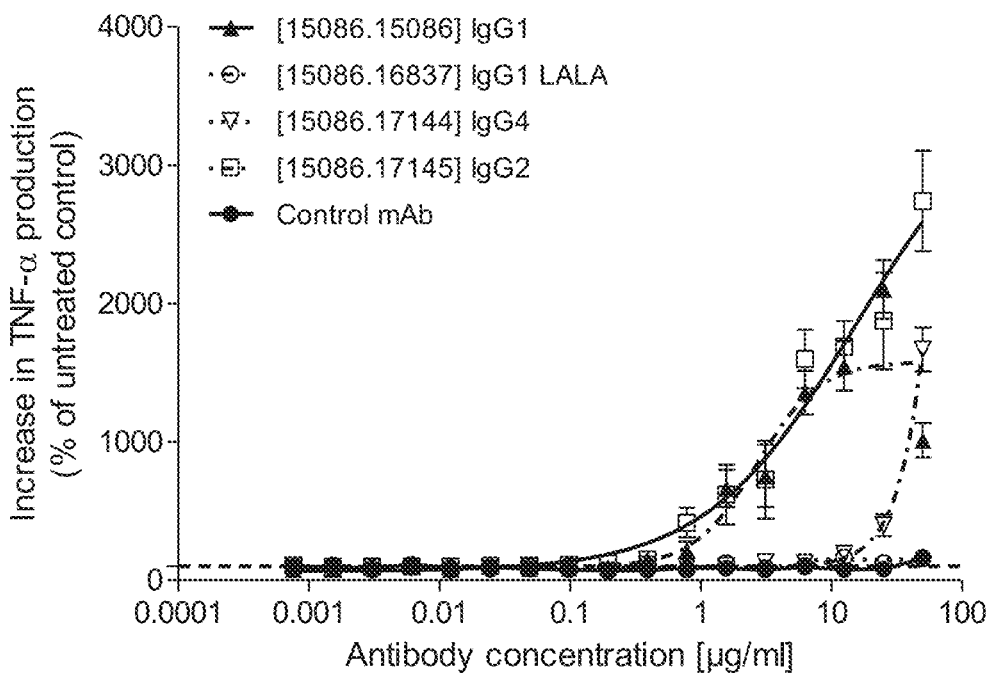
FIG. 2 shows dose-response curves of antibodies 15086.15086, 15086.16837, 15086.17145, and 15086.17144 for TNF-α production in a one-way MLR assay.

Dose-response curves in the one-way MLR assay of antibodies 15086.15086, 15086.16837, 15086.17145, and 15086.17144 are shown in FIGS. 1 and 2. The dose-response curves were generated by a two-fold titration of the antibodies with a starting concentration of 50 ug/ml. Each point on the graph represents the average of three replicates, with the error bars representing the SEM.

Antibodies 15086.15086 and 15086.17145 (IgG1 and IgG2 variants) showed similar functionality and induced a dose-dependent increase in both IFN-γ and TNF-α in the one-way MLR assay. Antibody 15086.17144 (IgG4 variant) only induced a response at the two highest concentrations, whereas no functionality was observed of antibody 15086.16837 (IgG1 LALA variant).

Example 4: Effect of Anti-TIM-3 Antibody on Purified Cell Subsets

TIM-3 was first reported to be selectively expressed by IFN-γ producing CD4+T helper cells and CD8+(CD8-positive) T cytotoxic cells, and was demonstrated to be a negative regulator of T-cell response. Subsequently, it was discovered that TIM-3 is highly expressed endogenously on dendritic cells, monocytes and natural killer (NK) cells (Freeman et al., *Immunol Rev* 235:172-89 (2010); Kuchroo et al., *Nat Rev Immunol* 8:577-580 (2008); Anderson et al., *Science* 318:1141-1143 (2007); and Da Silva et al., *Cancer Immunol Res* 2:410-422 (2014)). This example shows how ligation of TIM-3 by anti-TIM-3 antibodies has a direct effect on dendritic cells leading to an increase in TNF-α secretion.

Materials and Methods

PBMCs, naive CD4+ T-cells and naive CD8+ cells were isolated from healthy donor material. Dendritic cells from three individual healthy donors were generated as described previously in Example 3. The isolated cell subsets were incubated for 5 days with 10 ug/ml of the indicated antibodies, and TNF-α levels were determined using the Meso Scale electrochemiluminescence cytokine assay.

Results

Figure 3:
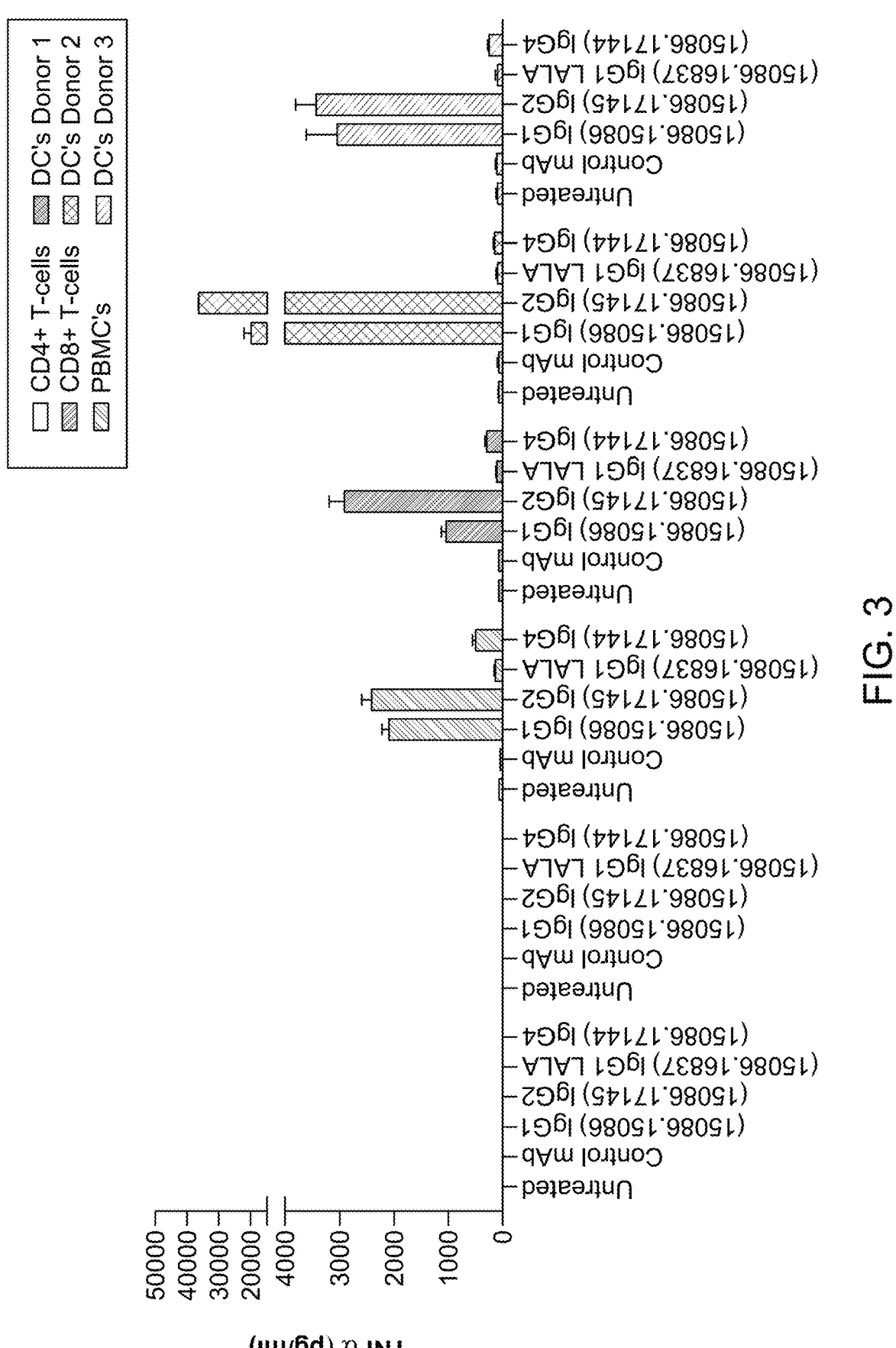
FIG. 3 shows the effect on purified dendritic cell subsets of antibodies 15086.15086, 15086.16837, 15086.17145, and 15086.17144, measured as TNF-α levels using the Meso Scale electrochemiluminescence cytokine assay.

The direct effect on purified cell subsets of antibodies 15086.15086, 15086.16837, 15086.17145, and 15086.17144 is displayed in FIG. 3, where each bar represents the average of five replicates and the error bars represent the SEM. The results demonstrate that the presence of the IgG1 (15086.15086) or IgG2 (15086.17145) variant of the anti-TIM-3 antibody resulted in an increase in TNF-α secretion from dendritic cells from all three donors. A similar effect was observed in the PBMC population containing multiple TIM-3 expressing cell subsets (e.g. monocytes and NK-cells). The IgG1 LALA (15086.16837) and IgG4 (15086.17144) variants had only a minimal effect on TNF-α secretion. None of the tested antibodies had an effect on naive CD4+ T-cells or naive CD8+ T-cells.

Example 5: Flow Cytometric Analysis of Anti-TIM-3 Antibodies for Phosphatidylserine Blocking Activity This example illustrates how an anti-TIM-3 antibody of the invention [15086.17145] was tested for phosphatidyl-serine (PtdS) blocking activity by performing a flow cyto-metric competition assay using surface-phosphatidylserine-positive apoptotic cells and fluorochrome-labeled soluble TIM-3.

Materials and Methods

Phosphatidylserine blocking activity was investigated in a cell-based assay, in which Jurkat T cells are induced to undergo apoptosis by Staurosporine (from *Streptomyces* sp., Sigma-Aldrich, USA) treatment. During apoptosis, PtdS is translocated from the cytoplasmic face of the plasma membrane to the cell surface and allows binding of R-PE-labeled human TIM-3-Fc chimera protein to be analyzed by flow cytometry. Commercially available recombinant TIM-3-Fc chimera protein (R&D Systems, USA) was conjugated to R-PE using the Lightning-Link® R-Phycoerythrin Conjugation Kit (Innova Biosciences, UK). For each antibody concentration to be tested, 25 µl TIM-3-PE dilution (corresponding to approx. 0.33 µg TIM-3-Fc) was mixed with 25 µl antibody (starting at 20 µg/ml final) in Annexin V binding buffer (BD Pharmingen™, USA) and incubated at room temperature (RT) for 20 minutes before addition to cells. Jurkat T cells were cultured in the presence of 1 µM Staurosporine for 2 h, washed once in RT binding buffer, and for each test, $2 \times 10^5$ cells in 50 µl binding buffer were combined with the antibody/TIM-3-PE mix. After 15 mins incubation at RT, 100 µl binding buffer was added, cells were spun-down by centrifugation, and pellets were re-suspended in 100 µl binding buffer for acquisition. Binding of TIM-3-PE to apoptotic cells was quantified by flow cytometry detecting PE fluorescence (MFI). In parallel, surface-exposure of PtdS on Staurosporine-treated cells was confirmed by Annexin V-PE staining (PE Annexin V Apoptosis Detection Kit I, BD Pharmingen™). Anti-PD-1 antibody Keytruda® (pembrolizumab; Merck & Co., Inc.) was used as negative control for TIM-3-binding/PtdS-blocking, 228 (EU numbering) was substituted with proline (Angal et al., *Mol. Immunol.* 30:105-108 (1993)). CHO cells were transfected with the resulting expression plasmids using a standard protein expression system. After antibody expression, the corresponding antibody supernatants were purified using standard protein A purification column chromatography.

TABLE 16

| Gene-synthesized antibody analogues and the corresponding antibody format | | | | |
|---|---|---|---|---|
| Antibody | Analogue name | Reference patent document | Sequence numbers in reference patent document | Different human isotype formats produced |
| ABTIM3 | 18564 ABTIM3 | WO 2015 117002 (A1) | SEQ ID NOs: 1 (VH) and 2 (VL) | IgG1, IgG1-LALA, IgG2, and IgG4 |
| 18571.18571 | Humanized ABTIM3 | WO 2015 117002 (A1) | SEQ ID NOs: 131 (VH) and 132 (VL) | IgG1, IgG1-LALA, IgG2, and IgG4 |
| mAb15 | 21563 mAb15 | WO 2016 111947 (A2) | SEQ ID NOs: 12 (VH) and 14 (VL) | IgG1, IgG1-LALA, IgG2, and IgG4 | and an anti-TIM-3 reference antibody ABTIM3 [18571.18571] (WO 2015/117002 A1 Novartis AG) was used as a positive control for TIM-3 binding/PtdS-blocking. In addition, a different anti-TIM-3 antibody [15338.15338], which was previously identified as a non-blocking antibody, was also used as negative control for PtdS blocking.

Results

Figure 4:
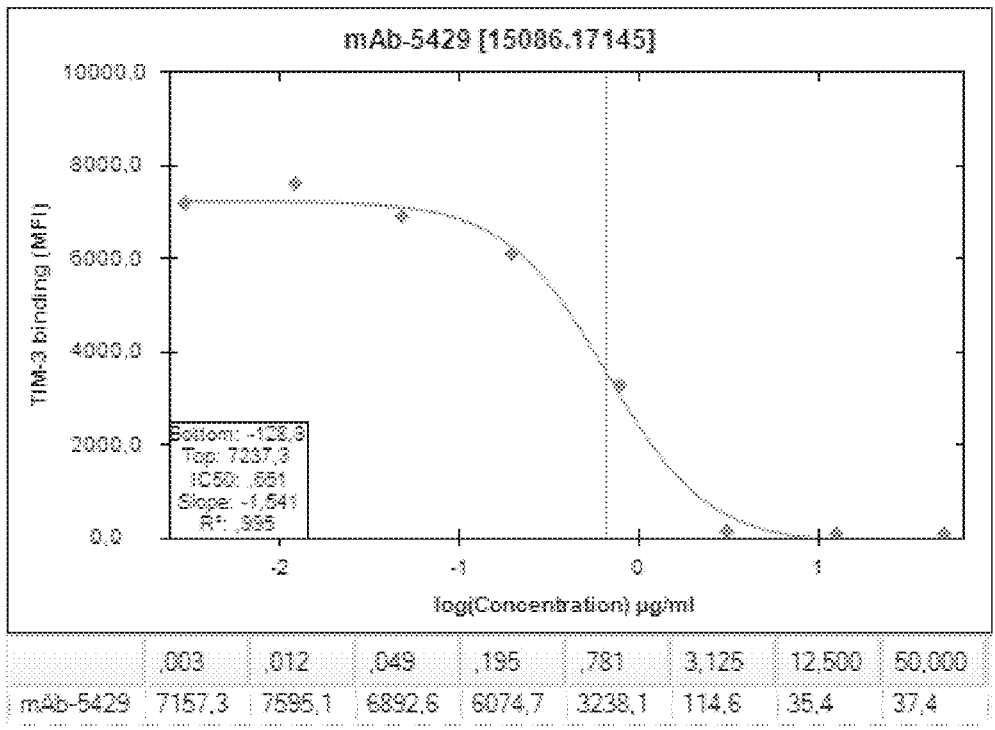
FIG. 4 shows TIM-3-Fc binding to phosphatidylserine (PtdS) positive (apoptotic) cells in the presence of an anti-TIM-3 antibody of the invention as well as a positive control anti-TIM-3 antibody and two negative control antibodies. A: Anti-TIM-3 antibody of the invention [15086.17145]; B: negative control non-blocking anti-TIM-3 antibody [15338.15338]; C: reference anti-TIM-3 antibody [18571.18571]; D: negative control anti-PD-1 antibody Keytruda® (pembrolizumab).
Figure 4:
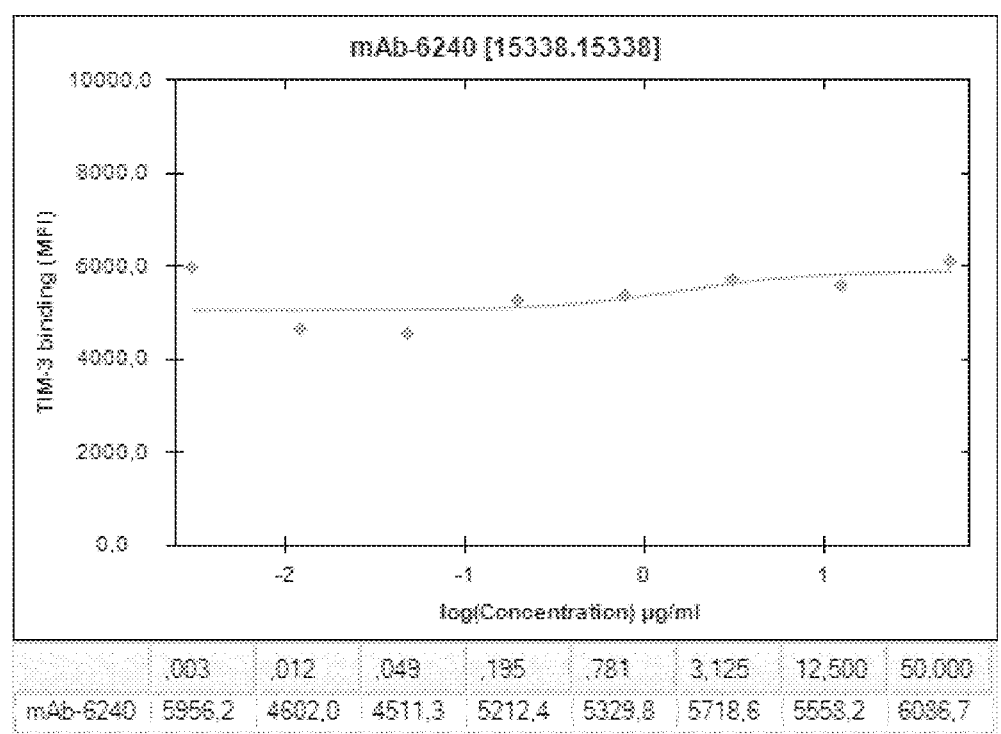
Figure 4:
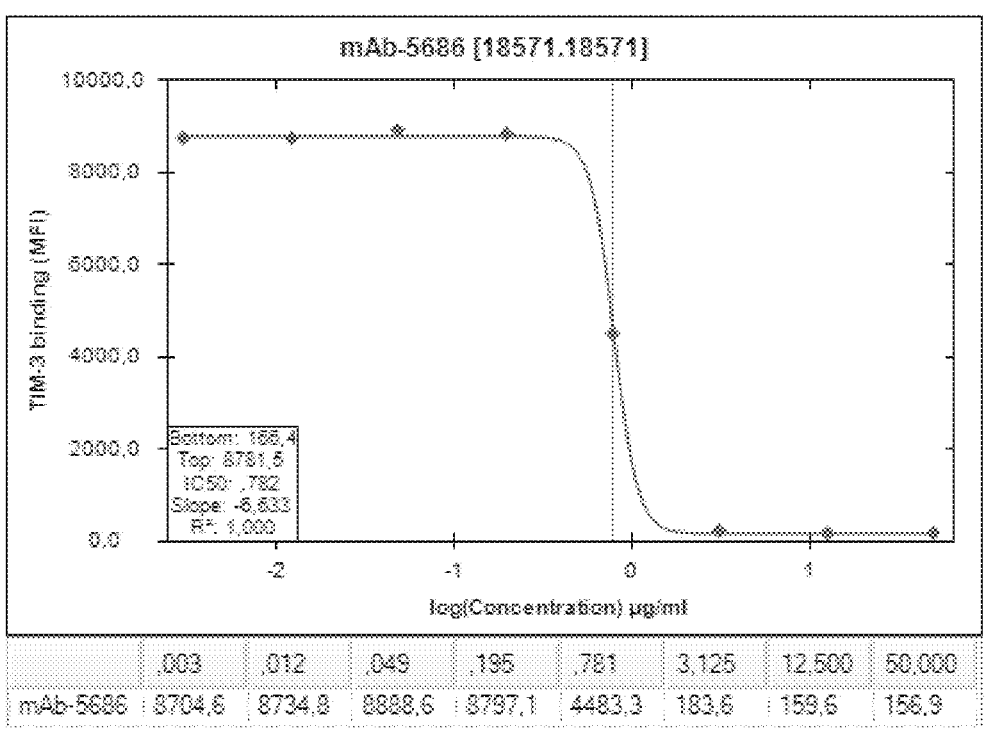
Figure 4:
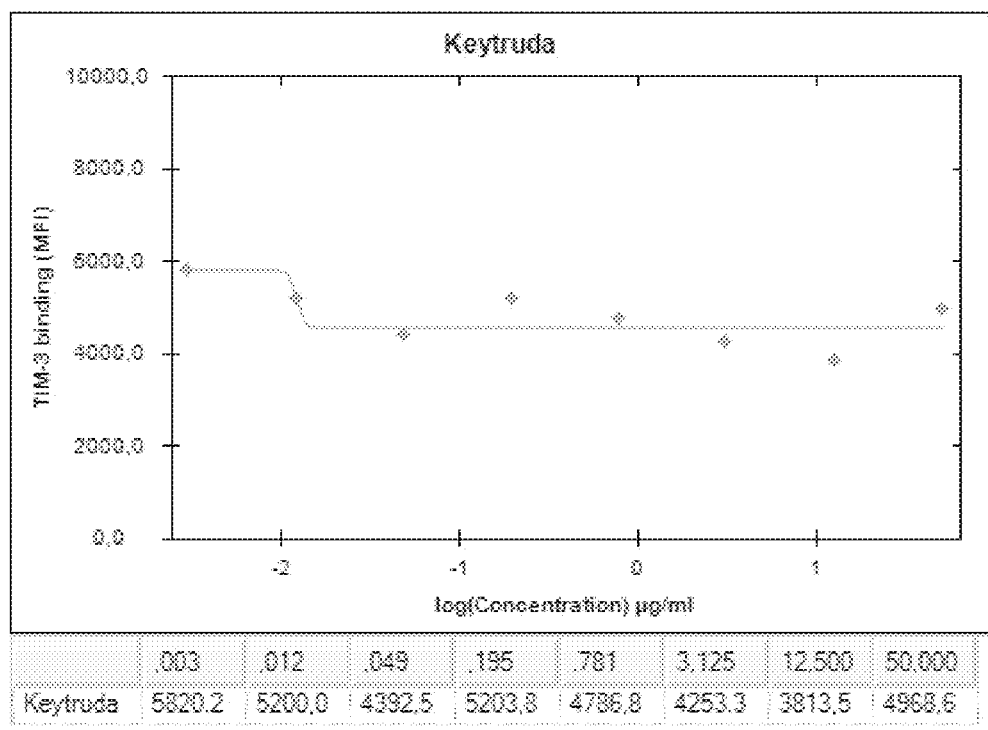

The results of the competition experiment are presented in FIG. 4. The anti-TIM-3 antibody [15086.17145] is able to inhibit the interaction of soluble TIM-3-Fc with cell-displayed PtdS in a dose-dependent manner (FIG. 4A). At 3.125 µg/ml, it blocks binding of TIM-3-Fc to PtdS-positive cells down to 2% of the binding detected in the presence of a non-blocking anti-TIM-3 antibody [15338.15338] (FIG. 4B). The reference anti-TIM-3 antibody [18571.18571] was able to block binding down to 3.2% at the same concentration (FIG. 4C). The results for the negative control anti-PD-1 antibody Keytruda® are shown in FIG. 4D.

Example 6: Cloning of Anti-TIM-3 Reference Antibody Analogues

Reference analogues of the anti-TIM-3 antibodies ABTIM3 and mAb15 are used in several of the examples herein. The reference analogues were generated as described below.

The heavy and light chain variable domain amino acid sequences of ABTIM3 and mAb15 were obtained from the patent applications shown in Table 16 below. The amino acid sequences of variable heavy chain (VH) and variable light chain (VL) fragments were reverse translated to DNA sequences with human codon usage. The corresponding DNA fragments were then synthesized and cloned into expression vectors containing constant human heavy chain constant regions (any one of four different isotype formats: IgG1, IgG1-LALA, IgG2, or IgG4) or human kappa light chain constant regions, resulting in full-length antibody heavy and light chain sequences. To prevent Fab arm exchange in the $IgG_4$ variant, the serine residue at position

Example 7: In Vitro Functional Evaluation of Additional Anti-TIM-3 Antibodies in a One-Way MLR Assay This example demonstrates in vitro functional activity of nine additional anti-TIM-3 antibodies by inducing dose-dependent secretion of IFN-γ in a one-way mixed lymphocyte reaction (MLR) assay.

Materials and Methods

The one-way MLR assay was set up as described above in Example 3. In brief, dendritic cells (DCs) and CD4+ T-cells were co-cultured for 5 days in the presence of the indicated antibodies. After 5 days of culture, supernatants were harvested and IFN-γ levels were determined using the Meso Scale electrochemiluminescence IFN-γ assay.

Results

Figure 5:
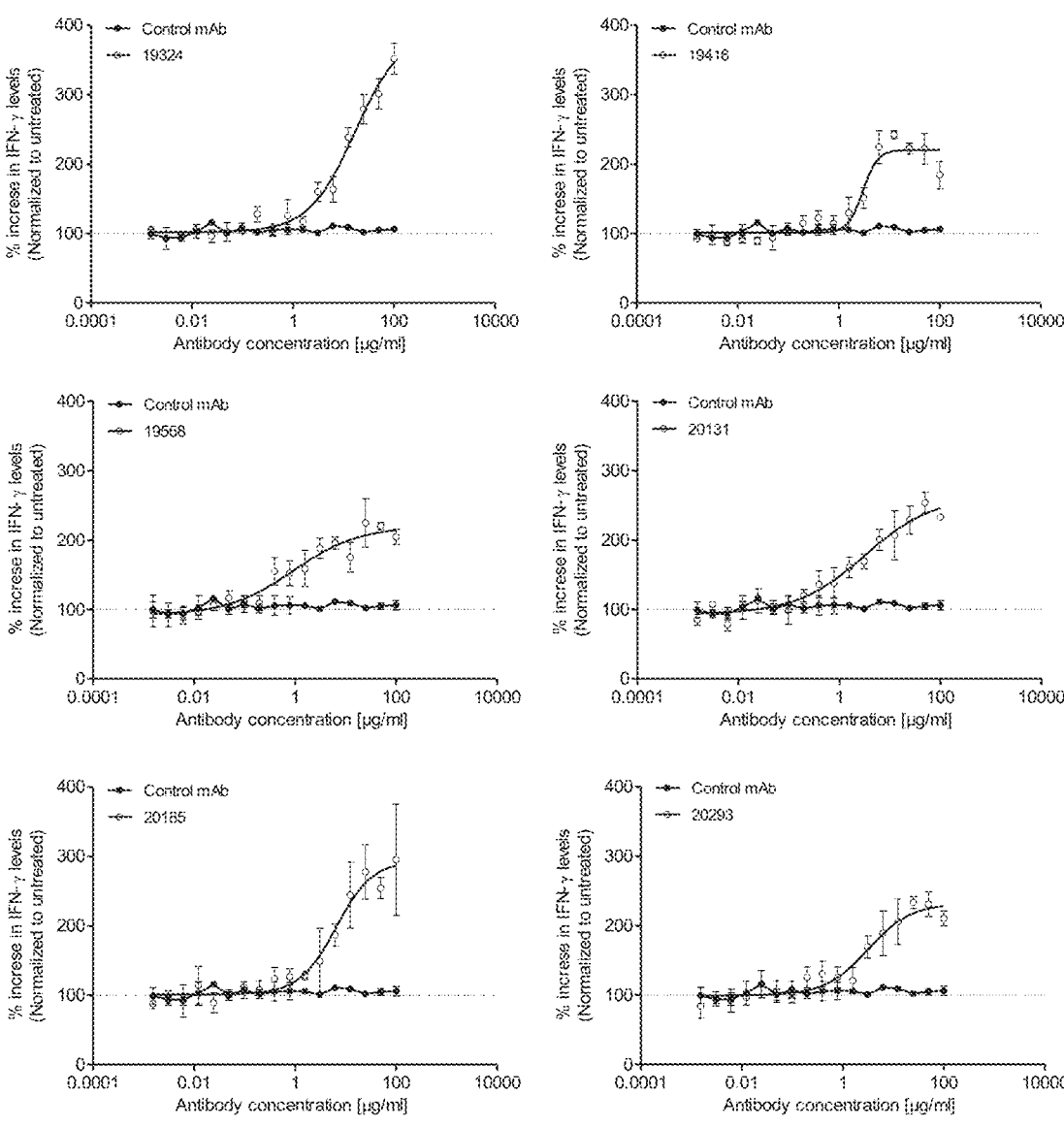
FIG. 5 shows dose-response curves of nine anti-TIM-3 antibodies for IFN-γ production in a one-way MLR assay.
Figure 5:
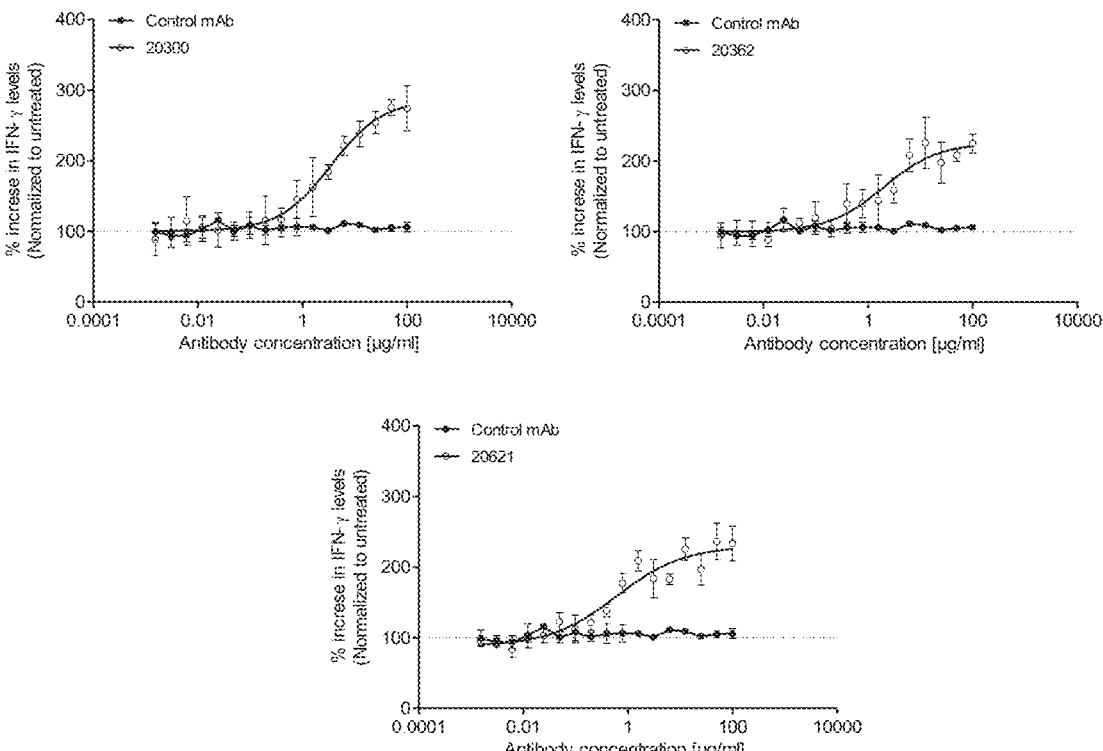

Dose-response curves for the nine additional anti-TIM-3 antibodies are shown in FIG. 5. All of the nine antibodies induced a dose-dependent increase in IFN-γ levels in this assay. Of note, no effect was observed of the reference antibodies ABTIM3 and mAb15. The dose-response curves were generated by a two-fold titration of the antibodies with a starting concentration of 100 µg/ml. Each point in the graph represents the average of three replicates and the error bars represent SEM.

Example 8: In Vitro Functional Evaluation of Additional Anti-TIM-3 Antibodies in a Two-Way MLR Assay This example demonstrates in vitro functional activity of ten anti-TIM-3 antibodies by inducing dose-dependent secretion of IFN-γ in a two-way mixed-lymphocyte reaction (MLR) assay.

Materials and Methods

In the two-way MLR assay, peripheral blood mononuclear cells (PBMCs) from two different healthy donors were co-cultured to induce an alloantigen specific reaction resulting in cytokine production and T-cell activation/proliferation. The PBMCs from the two different donors were mixed in a 1:1 ratio. After 5 days of culture, supernatants were harvested and IFN-γ levels were determined using the Meso Scale electrochemiluminescence cytokine assay.

Results

Figure 6:
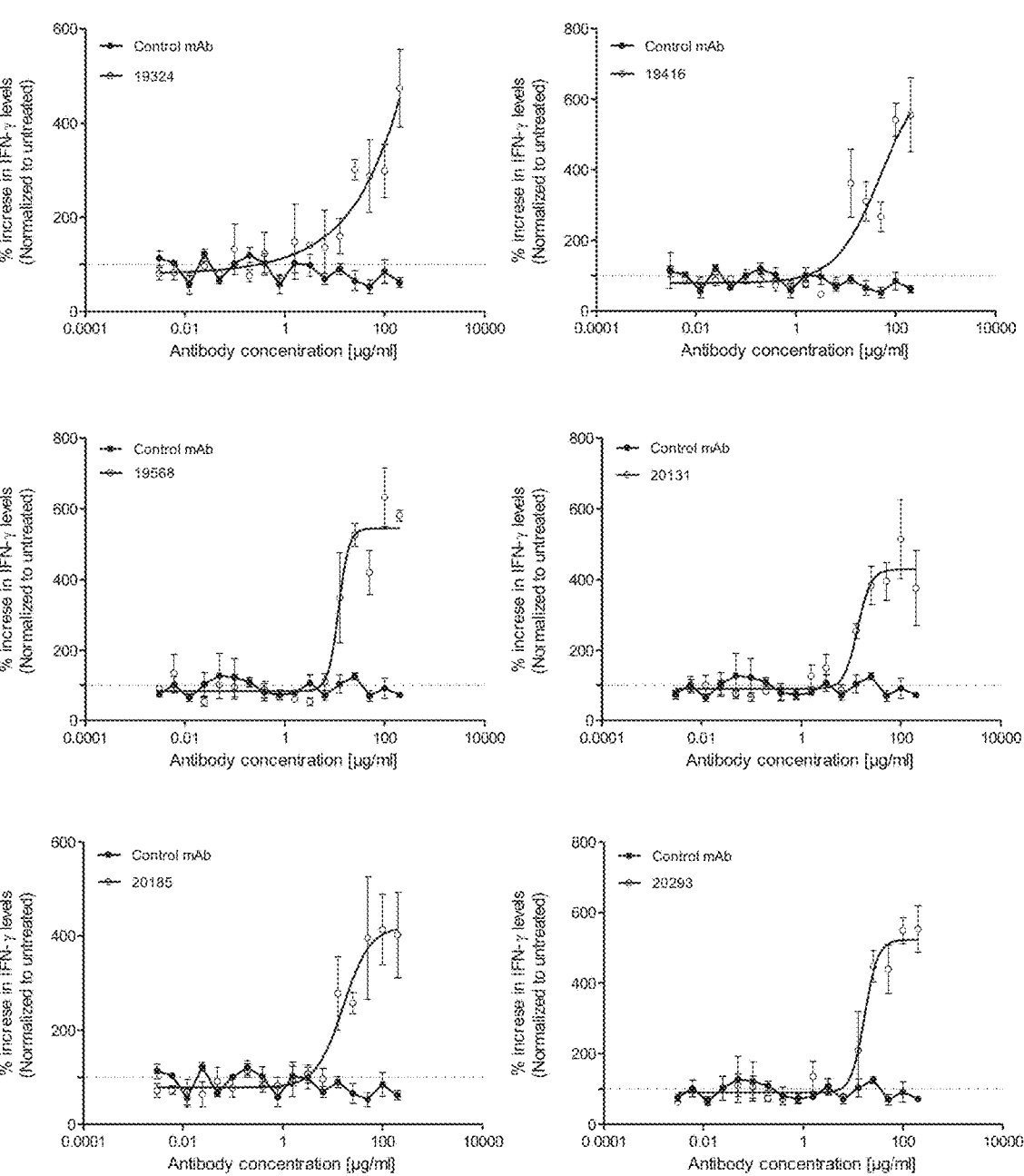
FIG. 6 shows dose-response curves of ten anti-TIM-3 antibodies for IFN-γ production in a two-way MLR assay. Antibody 15086.17145 is shown as "15086."
Figure 6:
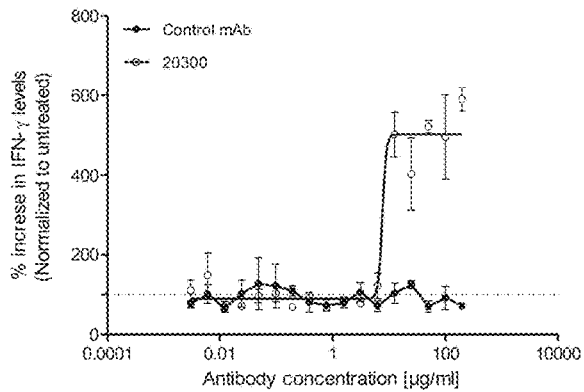
Figure 6:
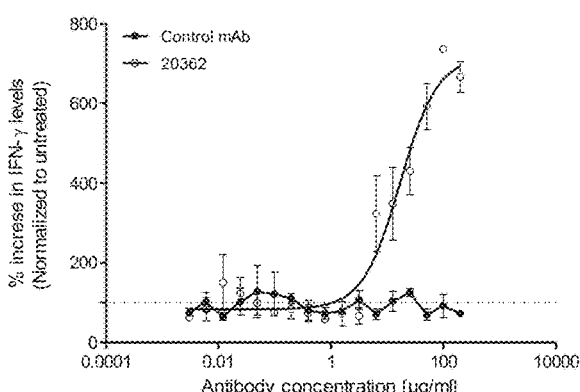
Figure 6:
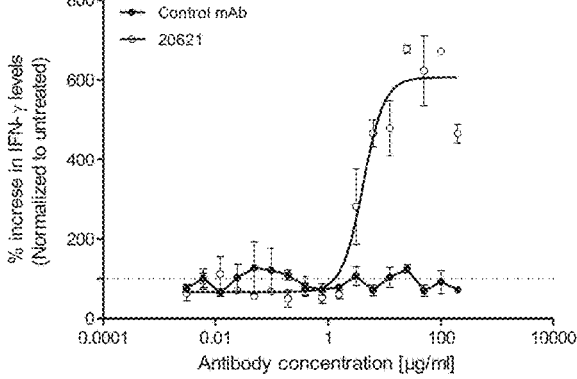
Figure 6:
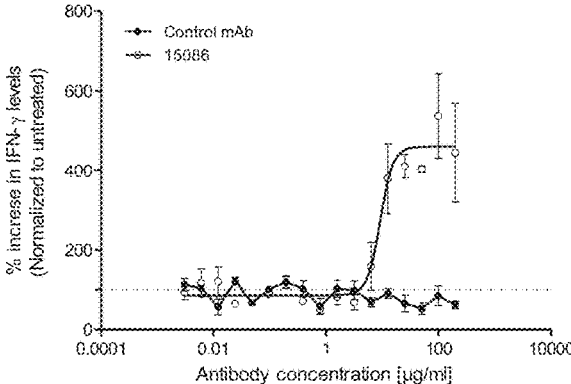

Dose-response curves for the ten anti-TIM-3 antibodies are shown in FIG. 6 for one donor pair. All of the anti-TIM-3 antibodies induced a dose-dependent increase in IFN-γ levels in this assay. Of note, no effect was observed of the reference antibodies ABTIM3 and mAb15. The dose-response curves were generated by a two-fold titration of the antibodies with a starting concentration of 100 µg/ml. Each point in the graph represents the average of three replicates and the error bars represent SEM.

Example 9: In Vitro Functional Evaluation of Additional Anti-TIM-3 Antibodies in a Dendritic Cell Assay This example demonstrates in vitro functional activity of nine anti-TIM-3 antibodies by inducing dose-dependent secretion of TNF-α from monocyte derived dendritic cells.

Materials and Methods

CD14+ monocytes were isolated from peripheral blood mononuclear cells (PBMCs) from healthy donor material. Dendritic cells (DCs) were differentiated from CD14+ monocytes by 6 days of culture with 20 ng/ml granulocyte-macrophage colony-stimulating factor (GM-CSF) and 20 ng/ml interleukin-4 (IL-4). The monocyte-derived dendritic cells were harvested and cultured for 5 days in the presence of the indicated antibodies. After 5 days of culture, supernatants were harvested and TNF-α levels were determined using the Meso Scale electrochemiluminescence TNF-α assay.

Results

Figure 7:
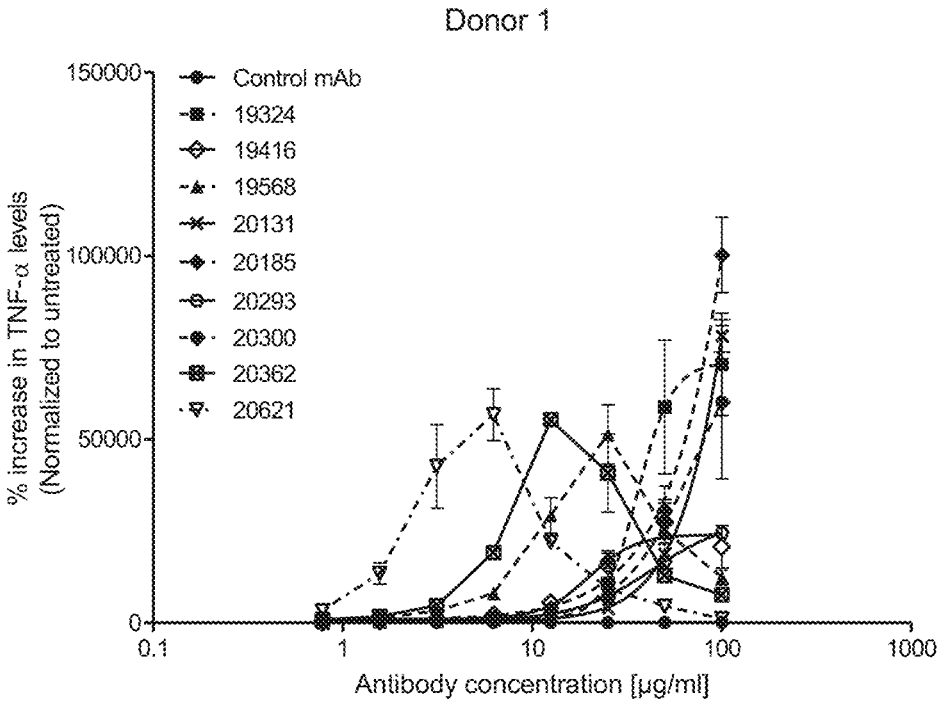
FIG. 7 shows dose-response curves of nine anti-TIM-3 antibodies for TNF-α production in monocyte-derived dendritic cells from two independent donors.
Figure 7:
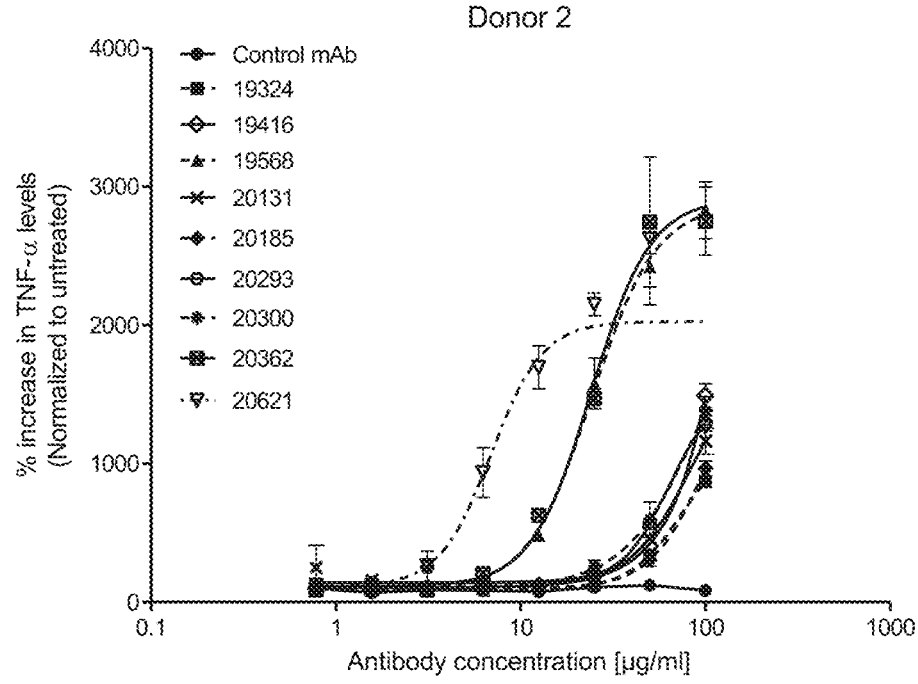

Dose-response curves for the nine additional anti-TIM-3 antibodies are shown in FIG. 7. All of the nine anti-TIM-3 antibodies induced a dose-dependent increase in TNF-α levels from monocyte-derived dendritic cells in two independent donors. Of note, no effect was observed of the reference antibodies ABTIM3 and mAb15. The dose-response curves were generated by a two-fold titration of the antibodies with a starting concentration of 100 µg/ml. Each point in the graph represents the average of three replicates and the error bars represent SEM.

Example 10: Measurement of Antibody Affinities for Human and Cynomolgus TIM-3

This example demonstrates the binding affinities of anti-TIM-3 Fab fragments for human and cynomolgus TIM-3 extracellular domains as measured by Surface Plasmon Resonance (SPR).

Materials and Methods

The kinetic binding analysis was performed by Surface Plasmon Resonance (SPR), using a Continuous Flow Microspotter (CFM, Wasatch Microfluidics, Salt Lake City, US) combined with an IBIS MX96 SPR instrument (IBIS Technologies, The Netherlands).

Anti-TIM-3 Fab fragments were generated from the corrected sequence variants of selected antibodies in IgG1 LALA format using standard enzymatic cleavage kits (Genovis, Sweden). Fab fragments are labeled as Fab [antibody number]. The heavy chain variable domain amino acid sequence used for Fab 15086 is the corrected sequence shown in SEQ ID NO: 7. The TIM-3 cDNA coding for the extracellular domain of human and cynomolgus TIM-3 was synthesized and cloned into a vector containing a CMV promoter and a human IgG1 Fc sequence (AA P101-K330), resulting in C-terminal fusion of IgG1 Fc to the cloned TIM-3 ECD. The TIM-3 Fc fusion constructs were generated by standard PCR and engineering techniques and the protein was expressed transiently in 2 ml culture using an ExpiCHO™ expression system. The human TIM-3 Fc fusion constructs were harvested after 9 days and supernatants were tested for binding affinity to anti-TIM-3 Fab fragments by SPR. Antigens were purified using standard procedures and captured onto a G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye® was positioned in the IBIS MX96 biosensor, remaining capture sites were blocked, and captured proteins were fixed to the surface using FixIT kit (Ssens BV, The Netherlands). Kinetic analysis was performed by applying a so called kinetic titration series (Karlsson R. 2006), where monomeric Fab fragments of the antibodies of the invention were injected in increasing concentrations from 1 nM to 100 nM without application of surface regeneration steps after each Fab injection. Fab association was performed for 15 minutes and antigen dissociation was performed for 15 minutes. The recorded binding responses were fitted to a simple Langmuir 1:1 binding model with Scrubber 2 software for calculation of the on-rate (kon or ka), off-rate (koff or kd), and affinity (KD) constants.

Results

The results of the affinity measurement demonstrate that Fab 15086, Fab 20293, and Fab 20131 and the two reference antibodies bind human and cynomolgus TIM-3 with different affinities. The detailed binding kinetics are shown in Table 17 below.

TABLE 17

Binding kinetics of anti-TIM-3 Fab fragments to human or cynomolgus TIM-3 ECD as measured by SPR.

| Fab Fragment | TIM-3 ECD | $k_{on}$ (M-1 S-1) | $k_{off}$ (s-1) | $K_D$ (nM) |
|---|---|---|---|---|
| 15086 | Human | 2.3E+05 | 5.0E−03 | 22 |
| 15086 | Cynomolgus | 1.3E+04 | 2.8E−02 | 2200 |
| 20293 | Human | 2.9E+05 | 3.6E−03 | 13 |
| 20293 | Cynomolgus | 1.7E+06 | 3.5E−03 | 21 |
| 20131 | Human | 7.6E+04 | 4.1E−04 | 5.5 |
| 20131 | Cynomolgus | 4.8E+06 | 3.9E−04 | 22 |
| 18564 ABTIM3 | Human | 2.7E+05 | 2.1E−04 | 0.77 |
| 18564 ABTIM3 | Cynomolgus | 1.5E+05 | 3.9E−03 | 25 |
| 21563 mAb15 | Human | 7.9E+05 | 6.3E−04 | 0.80 |
| 21563 mAb15 | Cynomolgus | ND | ND | ND |

ND: Not determined

Example 11: ELISA Determination of Antibody
Binding to Human and Cynomolgus TIM-3 ECD This example demonstrates the binding avidities of anti-TIM-3 antibodies for human and cynomolgus TIM-3 ECD as measured by ELISA.

Materials and Methods

Antibody-antigen binding was measured by ELISA with coated TIM-3 Fc fusion antigens at 1 μg/ml. Human and cynomolgus antigens were obtained from Sino Biologicals. Anti-TIM-3 antibodies were incubated with the coated antigens at different concentrations beginning from 150 μg/ml (1000 nM) in 2-fold serial titrations. After wash, bound antibodies were detected by HRP (horse radish peroxidase)-conjugated secondary antibodies.

Results

The ELISA demonstrated that all of the evaluated antibodies are capable of binding to both human and cynomolgus TIM-3 ECD. The concentration of anti-TIM-3 antibodies yielding half maximum binding (EC50) is reported. All tested antibodies bound human TIM-3 with EC50 values around 1 nM or lower, while much more variation was observed in the binding to cynomolgus TIM-3 (Table 18). Some antibodies such as 20131, 20185, 20293 and ABTIM3 showed identical binding to both human and cynomolgus TIM-3. Other antibodies such as 19324, 19416, 19568, and 20300 showed intermediate binding to cynomolgus TIM-3, while antibodies 20362, 20621 and 15086.17145 showed weak cross-reactivity to cynomolgus TIM-3 (more than 100-fold EC50 reduction). The binding curves for the antibodies that exhibited the lowest cynomolgus TIM-3 cross-reactivity clearly showed saturated binding to the antigen when tested at highest concentration in the ELISA evaluation.

TABLE 18

Binding avidities (EC50) of anti-TIM-3 antibodies to human
or cynomolgus TIM-3 as measured by ELISA

| | EC50 (nM) | | Ratio |
| Antibody | Human TIM-3 | Cynomolgus TIM-3 | Cynomolgus/Human EC50 |
| --- | --- | --- | --- |
| 19324 | 0.73 | 18.38 | 25 |
| 19416 | 0.20 | 9.42 | 47 |
| 19568 | 0.38 | 30.20 | 79 |
| 20131 | 0.13 | 0.13 | 1 |
| 20185 | 0.17 | 0.15 | 1 |
| 20293 | 0.31 | 0.32 | 1 |
| 20300 | 1.13 | 45.30 | 40 |
| 20362 | 0.26 | 124.80 | 481 |
| 20621 | 0.22 | 29.70 | 135 |
| 15086.17145 | 0.125 | 17.50 | 134 |
| 18564 ABTIM3 | 0.07 | 0.07 | 1 |

Example 12: Epitope Binning of Anti-TIM-3
Antibodies

This example illustrates how anti-TIM-3 antibodies of the invention can be grouped into epitope bins based on paired competition patterns. Antibodies belonging to different epitope bins recognize different epitopes on the TIM-3 extracellular domain (ECD).

Materials and Methods

Investigation of paired antibody competition was performed by Surface Plasmon Resonance (SPR) analysis using a Continuous Flow Microspotter (CFM) (Wasatch Microfluidics, US) combined with an IBIS MX96 SPR instrument (IBIS Technologies, The Netherlands). Surface Plasmon Resonance imaging analysis was performed on a G-a-hu-IgG Fc SensEye® SPR sensor (Ssens BV, The Netherlands). A total of sixteen human anti-TIM-3 IgG2 antibodies and two IgG4 reference antibodies (ABTIM3 and mAb15) were diluted to 15 μg/ml in PBS buffer containing 0.05% Tween 20 (PBS-T), pH 7.0. Antibodies were captured onto the anti-Fc sensor surface by spotting for 15 minutes using a Continuous Flow Microspotter. After spotting, the SensEye® was positioned in the IBIS MX96 biosensor and residual anti-Fc sites blocked by injection of 30 μg/ml non-specific human IgG1. Captured antibodies were conjugated to the surface using a FixIt kit (Ssens BV, The Netherlands). After sensor preparation, antibody competition analysis was performed using a classical sandwich assay where immobilized antibodies bound 200 nM soluble monovalent TIM-3 antigen (Acro Biosystems, China), followed by probing for binding with another anti-TIM-3 antibody. Next, individual injections of each of the eighteen anti-TIM-3 antibodies diluted to 15 μg/ml in PBS-T buffer were performed to establish antibody competition patterns. After each competition cycle, the sensor surface was regenerated with 100 mM H3PO4 buffer, pH 3.0.

Results

Figure 8:
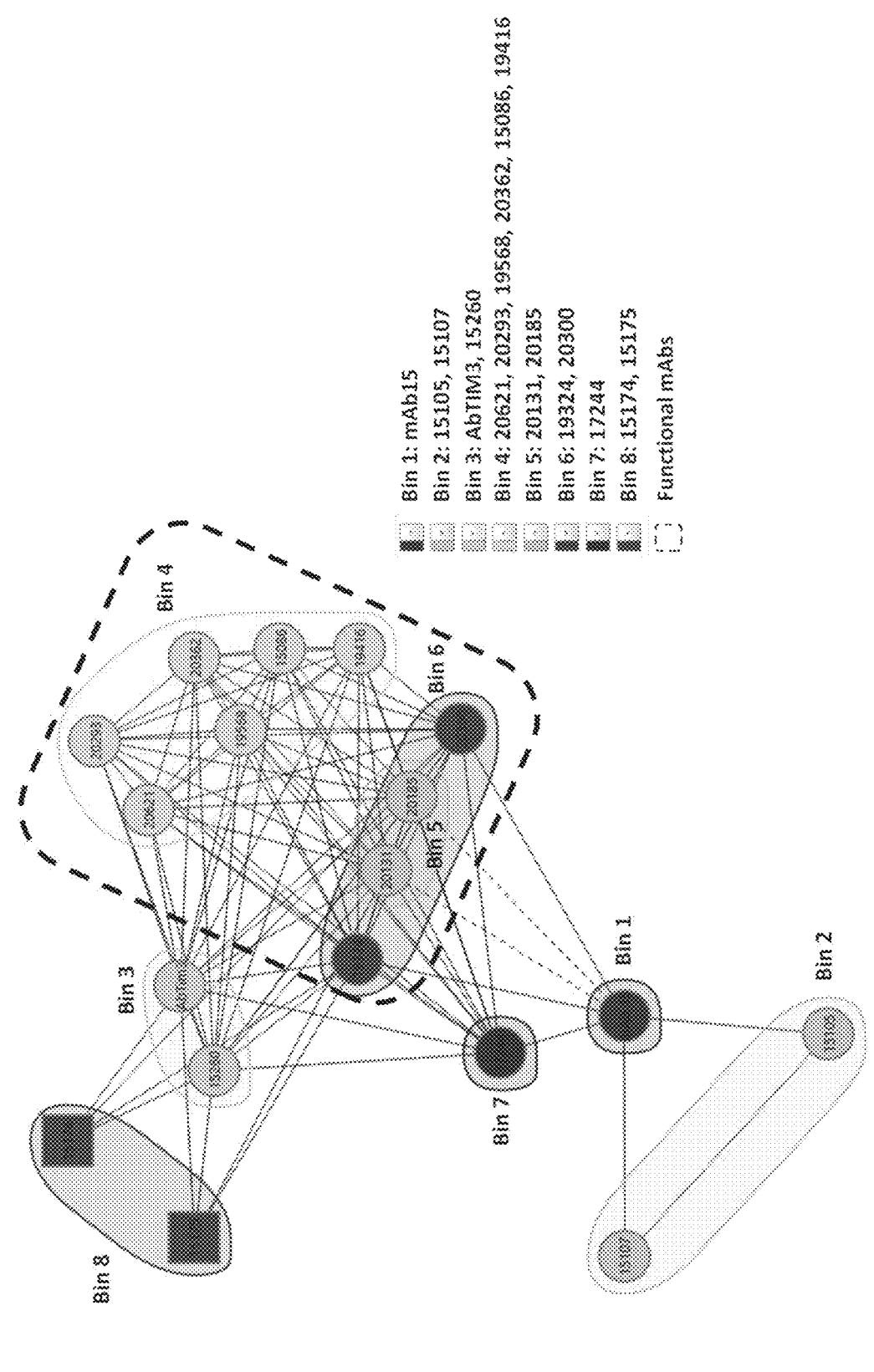
FIG. 8 shows an overview of the epitope groups (epitope bins) identified by binding competition analysis of a panel of eighteen anti-TIM-3 antibodies. Circled antibodies connected by black lines indicate cross blocking activity in both orientations. Squared antibodies indicate unidirectional blocking when the antibody is tested in solution only. Dashed lines indicate unidirectional blocking when antibodies are immobilized only. Antibodies are grouped according to competition patterns with other anti-TIM-3 antibodies. Antibody 15086.17145 is shown as "15086."

The competition pattern of eighteen anti-TIM-3 antibodies is presented in FIG. 8. Antibodies mAb15 (bin1), 15105 and 15107 (bin 2), 15260 and ABTIM3 (bin 3), 17244 (bin 7), and 15174 and 15175 (bin 8) did not show functional activity in the cell-based MLR assays described herein, but were included because they recognized distinct epitopes. Bin 8 antibodies were only tested in solution, since TIM-3 binding was significantly reduced when these antibodies were captured on the sensor surface (unidirectional blocking). Hence these antibodies are represented by squares. Functional anti-TIM-3 antibodies were found to bind three cross-competing epitope bins (bins 4, 5 and 6). Functional antibodies belonging to epitope bin 4 included antibodies 20621, 20293, 19568, 20362, 15086.17145, and 19416. These antibodies cross-blocked each other and antibodies from epitope bins 3, 5, 6 and 7. Functional antibodies belonging to epitope bin 5 included antibodies 20131 and 20185. These antibodies cross-blocked each other and antibodies from epitope bins 3, 4, 6 and 7. Additionally, 20131 and 20185 also prevented mAb15 from binding when they were captured on the sensor surface only (unidirectional blocking, dashed lines). Finally, functional antibodies belonging to epitope bin 6 included antibodies 19324 and 20300. These antibodies cross-blocked each other and all other antibodies except antibodies from bin 2.

It can be deduced from the results presented above that functional antibodies from epitope bins 4, 5 and 6 are binding epitopes that are distinct from the reference antibodies ABTIM3 (bin 3) and mAb15 (bin 1) (FIG. 1), since each binning group has unique competition patterns compared to the other anti-TIM-3 antibodies in the panel.

Example 13: Epitope Mapping of Anti-TIM-3
Antibodies by TIM-3 Mutagenesis

Antibody epitopes can generally be characterized as linear epitopes (also termed continuous epitopes) or conformational epitopes (also termed discontinuous epitopes). While linear epitopes are defined based on a single continuous amino acid sequence, conformational epitopes may consist of many smaller discontinuous linear sequences or single contact residues. A collection of contact residues that cluster at the intermolecular protein interface between the antibody and the antigen is also termed a hot spot (Moreira et. al., Proteins 68(4):803-12 (2007)). It is now widely acknowledged that most B-cell epitopes are discontinuous in nature (Sivalingam and Shepherd, *Mol Immunol.* 51(3-4):304-9 (2012)), Kringelum et al., *Mol Immunol.* 53(1-2):24-34 (2013)) with the average epitope spanning 15-22 amino acid residues of which 2-5 amino acids contribute most of the binding (Sivalingam and Shepherd, supra).

By ranking binding affinity to 129 different TIM-3 mutants, this example illustrates how the binding epitopes of Fab 15086, Fab 20293, and Fab 20131 can be divided into linear epitopes and hotspots that are distinct from the epitopes recognized by reference antibodies ABTIM3 and mAb15.

Materials and Methods

The human TIM-3 receptor consists of an extracellular domain (ECD) of 181 amino acids (residues 22-202) followed by a transmembrane domain (residues 203-223) and a cytoplasmic domain (residues 224-301). TIM-3 belongs to the immunoglobulin super family and the ECD is composed of two domains—a mucin domain and an IgV domain. The IgV domain contain a two layer β-sandwich made from interactions of 7 anti-parallel β-strands arranged into two β-sheets with GFCC' β-strands on one side and BED β-strands on the opposing side. The two β-sheets are stabilized by a disulphide bond between resides C54-C123. A crystal structure is available for the human TIM-3 IgV (PDB 5F71). The TIM-3 IgV domain does not have an A strand like other IgV domains, but possesses two additional disulfide bonds (C58-C63 and C52-C110) that position the CC' and FG loops in close proximity, forming a unique cleft for phosphatidylserine (PS) ligand binding. A crystal structure of the murine TIM-3 in complex with the PS ligand exists (3KAA), demonstrating ligand binding contacts to the CC' and FG loops.

Several ligands and/or co-receptors for TIM-3 have been identified, including HMGB-1, galectin-9, CEACAM-1, and phosphatidylserine (Chiba et al., *Nat. Immunology* 13(9): 832-42 (2012), Li et al., *Hepatology* 56(4):1342-51 (2012), DeKruyff et al., *J Immunology* 184(4): 1918-30 (2010), Das et al., *Immunol Rev.* 276(1):97-111 (2017)).

The protein sequences of human TIM-3 and orthologues were downloaded from UniProt; human (Q8TDQ0, SEQ ID NO: 236), cynomolgus monkey (*Macaca fascicularis*, G7P6Q7; SEQ ID NO: 237), mouse (*Mus musculus*, Q8VIM0, SEQ ID NO: 238) and rat (*Rattus norvegicus*, P0C0K5, SEQ ID NO: 239). These sequences are shown in Table 23. The sequence identity between the different extracellular TIM-3 amino acid sequences is shown in Table 19 below.

TABLE 19

| Amino acid differences from and sequence identity to human TIM-3 extracellular domain. | | |
| --- | --- | --- |
| | Amino Acid Differences | % Sequence Identity |
| Cynomolgus TIM-3 ECD | 22 | 85.3 |
| Rat TIM-3 ECD | 54 | 64.0 |
| Mouse TIM-3 ECD | 59 | 60.7 |

From the crystal structures and amino acid sequences, surface exposed amino acid residues were identified and 82 individual alanine substitutions were designed on human TIM-3 ECD (Alanine scanning).

To map linear epitopes in the context of the native human TIM-3 structure, 47 chimeric proteins were generated where 10 amino acids in the human TIM-3 ECD sequence were sequentially exchanged to mouse sequence in segments that overlapped by 5 amino acids, and supplemented with rat and cynomolgus versions in critical loops. The sequence exchanges were performed in the extracellular domain of human TIM-3 spanning amino acids 22-199.

The cDNA coding for the extracellular domain of human TIM-3 was synthesized and cloned into a vector containing the CMV promoter and the human IgG1 Fc sequence (AA P101-K330), resulting in C-terminal fusion of IgG1 Fc to the cloned TIM-3 ECD. Mutated human TIM-3 Fc fusion constructs were generated by standard PCR and engineering techniques and protein was expressed transiently in 2 ml culture using an ExpiCHO™ expression system. The human TIM-3 Fc fusion constructs were harvested, purified and tested for binding affinity to anti-TIM-3 Fab fragments by Surface Plasmon Resonance (SPR). The TIM-3 fusion proteins were immobilized onto a G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye® was positioned in an IBIS MX96 biosensor and captured proteins were fixed to the surface using FixIT kit (Ssens BV, The Netherlands). Kinetic analysis was performed by applying a so called kinetic titration series (Karlsson R. 2006), where monomeric Fab fragments of the antibodies of the invention were injected in increasing concentrations from 1 nM to 100 nM without application of surface regeneration steps after each Fab injection. Fab association was performed for 15 minutes and antigen dissociation was performed for 15 minutes. The recorded binding responses were fitted to a simple Langmuir 1:1 binding model with Scrubber 2 software for calculation of the on-rate (kon or ka), off-rate (koff or kd) and affinity (KD) constants.

Results

The binding affinity of anti-TIM-3 Fabs 15086, 20293, 20131 and reference analogs ABTIM3 and mAb15 were evaluated with respect to altered binding to TIM-3 mutant constructs.

The binding affinities of the Fab fragments for the mutated TIM-3 constructs were expressed as the ratio between KD mutant/KD wildtype (normalized binding affinity). Tables 20 and 21 show the chimeric proteins and alanine mutants that gave differentiating results. An at least 5-fold affinity reduction was employed as a cut-off criteria for detecting reduced binding affinity to mutated TIM-3 constructs. In some instances, no binding could be detected to specific Fabs. These constructs were listed as NB (Not Binding).

The analysis showed that the binding epitopes of anti-TIM-3 Fabs 15086, 20293 and 20131 were clearly distinct compared to reference antibodies ABTIM3 and mAb15. 15086 and 20293 did not bind the chimeric protein with mouse sequence inserted at positions 62-67, close to the ligand binding loops CC' and FG, whereas the reference ABTIM3 did bind (Table 20). The epitope of 15086 on TIM-3 extended beyond this amino acid stretch including P50, V60, F61, E62, G64, R69 and FG loop residues I117, M118, D120 as evidenced from alanine scanning (Table 21).

*Nat. Immunology* 13(9):832-42 (2012), Das et al., *Immunol Rev.* 276(1):97-111 (2017)), whereas the two reference antibodies have epitopes situated more on the middle part of the IgV domain (mAb15) and on the other side of the IgV domain (ABTIM3). The results are consistent with the epitope binning data, which shows that mAb15 and ABTIM3 can bind TIM-3 simultaneously (Example 12). Based on the epitope location of 15086, 20293, and 20131, each antibody is predicted to be able to block the binding of TIM3 ligands (phosphatidylserine, CEACAM-1 and HMGB-1.

TABLE 20

Summary of binding affinity analysis for Fab fragments binding mutated TMI-3-ECD constructs with inserted mouse, rat or cynomolgus sequence segments. Normalized binding expressed as KD mutant/KD wild type.

| Chimeric construct # | Scanned Region hu TIM-3 | Mutated Region hu TIM-3 | Introduced mutation from other species | 15086 | 20293 | 20131 | 18564 (ABTIM3) | mAb15 |
|---|---|---|---|---|---|---|---|---|
| 1 | 22-31 | AA 22-28 | S22L; V24N; R27V; A28F | 1.0 | 1.4 | 1.0 | *5.4* | ND |
| 2 | 62-71 | AA 62-67 | E62Q; G64T; V66E; V67L | NB | NB | 1.7 | 0.7 | NB |
| 3 | 72-81 | AA 74-80 | D74N; N76T; W78Q; T79K;79S80 | 0.6 | 1.3 | 1.0 | 1.9 | NB |
| 4 | 77-85 | AA 78-85 | W78Q; T79K; 79S80; W83Q; N85K | 1.0 | 1.4 | 1.0 | 2.0 | NB |
| 5 | 81-90 | AA 83-89 | W83Q; N85K; D87N; R89Y | 3.0 | 0.7 | 2.7 | 1.7 | *19.3* |
| 6 | 106-115 | AA 107-114 | I107T; I114F | 0.6 | 0.6 | 2.0 | *17.5* | 1.2 |
| 7 | 111-120 | AA 114-117 | I114F; I117L | 0.7 | 3.1 | *8.4* | 1.1 | 2.2 |
| 8 | 121-130 | AA 123-128 | F123H; L125V; 127V128 | 0.9 | 1.2 | 1.1 | *31.0* | 0.8 |

Figure 9:
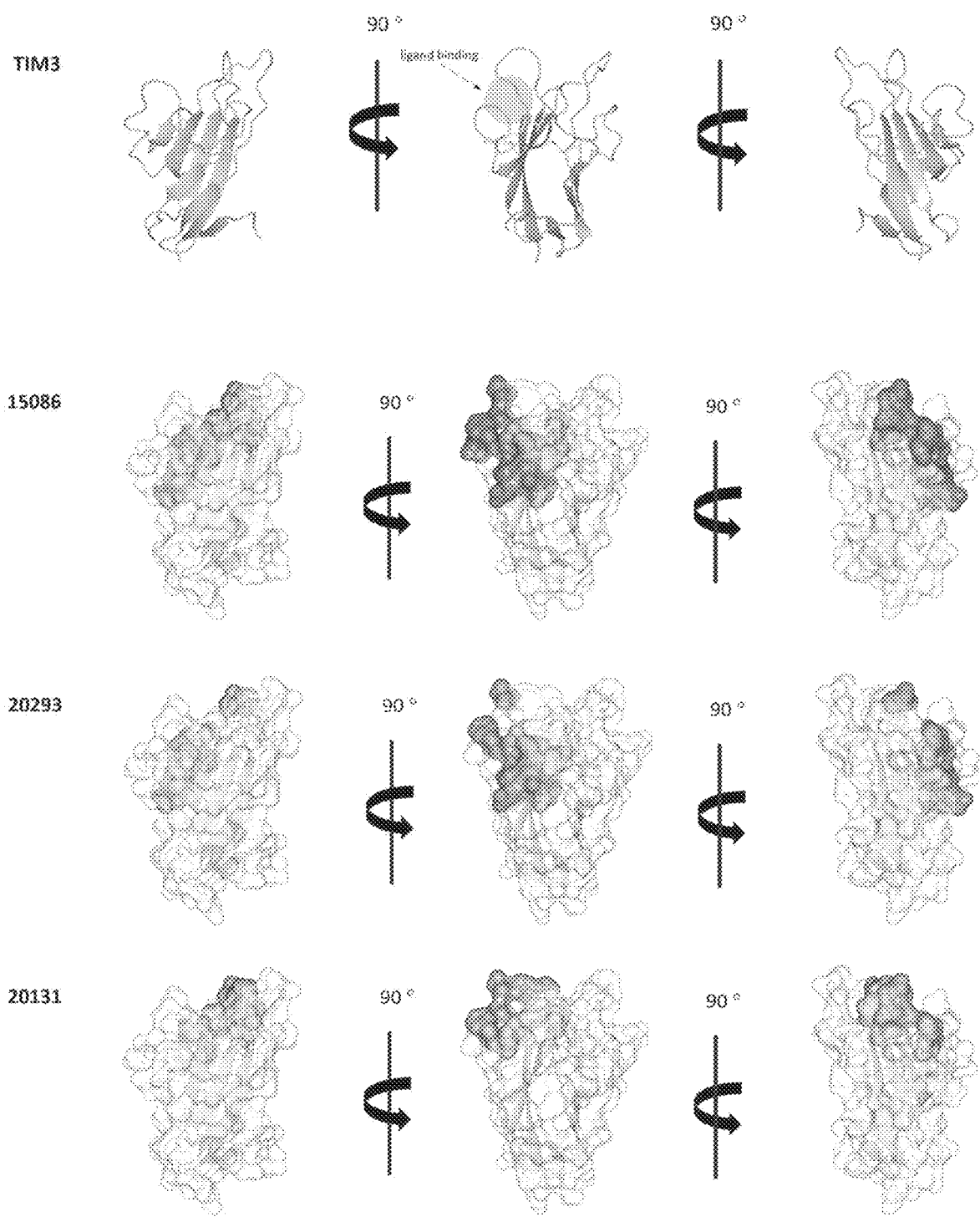
FIG. 9 shows the locations of antibody epitopes on the structure of the human TIM-3 IgV domain (PDB 5F71). A cartoon of the human TIM-3 IgV domain is shown in three different orientations and the location of the phosphatidyl-serine binding site is indicated. The locations of the mapped epitopes are presented in dark colors on a TIM-3 space filling model for each antibody. Fab fragment 15086 is shown as "15086" and Fab fragment 20293 is shown as "20293."
Figure 9:
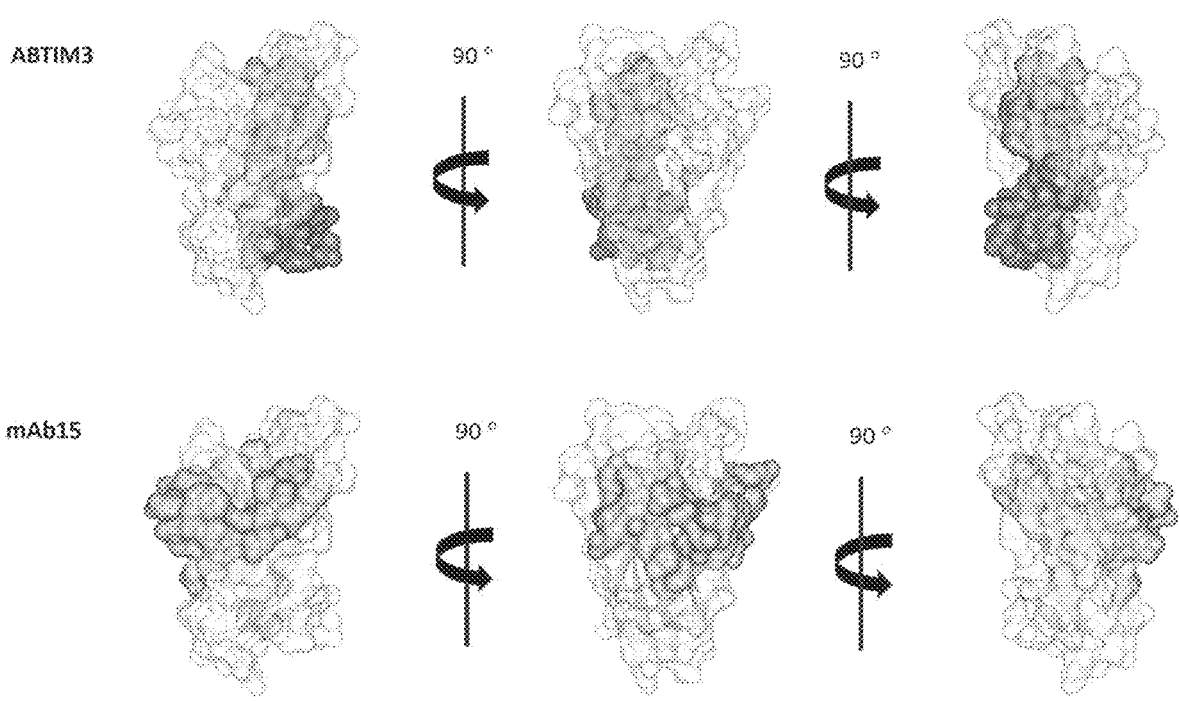

(non-italicized) <5-fold KD change Chimeric mutants
(Italicized) >5-fold KD change Chimeric mutants
NB No binding of Chimeric mutants
ND not determined Fab 20293 had a very similar epitope to 15086, except that residues M118 and D120 only affected binding to 15086 when mutated to alanine. Fab 20131 was found to bind a different epitope present in the FG loop at residues 114-117, and this was extended by alanine scanning to include residues 118, 120 and also the CC' residues F61 and E62. Common to 15086, 20293, and 20131 was sensitivity for an alanine mutation at position F61, to which neither of the two reference antibodies showed sensitivity. Although reference antibody mAb15 did not bind the mutated sequence at positions 62-67, analogous to 15086 and 20293, the epitope of mAb15 was clearly distinct since this antibody did not bind to two additional constructs where the sequence from position 74-85 was exchanged to mouse. Antibody ABTIM3 clearly exhibited a different epitope defined by the linear constructs mutated at positions 22-28, 107-144 and 123-128 as evidenced by the changed binding affinity to these proteins (Table 20). A summary of the epitope mapping findings is shown in Table 22 below and a molecular model of how the epitopes map on the surface of the TIM-3 IgV domain is presented in FIG. 9.

In summary, we have shown at a molecular level by analyzing the binding to a panel of 129 TIM-3 mutants that the three Fabs 15086, 20293, and 20131 recognize unique but partially overlapping epitopes at the top of the TIM-3 IgV domain. This finding is consistent with the epitope binning analysis (Example 12) showing that all three antibodies bind overlapping cross-competing epitopes that together constitute a functional surface on the TIM-3 IgV domain. These epitopes clearly overlap with the phosphatidylserine binding site, as well as amino acid E62 that is essential for HMGB-1 and CEACAM1 binding (Chiba et al.,

TABLE 21

Summary of binding affinity analysis for Fab antibodies binding alanine scanned human TIM-3 ECD mutants. Normalized binding expressed as KD mutant/KD wild type.

| Mutation | 15086 | 20293 | 20131 | 18564 (ABTIM3) | mAb15 |
|---|---|---|---|---|---|
| P50A | *82.7* | 4.9 | *53.5* | 4.2 | *308.8* |
| V60A | *11.3* | 1.7 | 1.0 | 1.6 | 1.4 |
| F61A | NB | NB | N.B. | 1.0 | 0.9 |
| E62A | *38.0* | 3.7 | *6.5* | 4.4 | 4.0 |
| G64A | *18.5* | 2.0 | 0.9 | 2.1 | 1.7 |
| R69A | NB | NB | 0.7 | NB | NB |
| I114A | 1.3 | 0.8 | 4.8 | 1.5 | 1.3 |
| I117A | *75.2* | *9.3* | NB | 0.9 | 1.2 |
| M118A | *14.4* | 0.4 | NB | 0.9 | 1.0 |
| D120A | *7.1* | 2.1 | *23.3* | 6.5 | 4.4 |
| E121A | 1.1 | 0.8 | 2.5 | *10.6* | 1.3 |

(non-italicized) <5 fold KD change Alanine mutants
(italicized) >5-fold KD change Alanine mutants
NB No binding of alanine mutants

TABLE 22

Summary of the binding epitopes identified for tested anti-TIM-3 antibodies

| Antibody | Ligand (PS) blocking | Epitope Bin | Linear epitope | Contact Residues |
|---|---|---|---|---|
| 15086 | Yes | 4 | 62-67 | P50, V60, F61, E62, G64, R69 I117, M118, D120 |

TABLE 22-continued

| Summary of the binding epitopes identified for tested anti-TIM-3 antibodies | | | | |
|---|---|---|---|---|
| Antibody | Ligand (PS) blocking | Epitope Bin | Linear epitope | Contact Residues |
| 20293 | Yes | 4 | 62-67 | F61, R69 I117 |
| 20131 | Yes | 5 | 114-117 | P50, F61, E62, I117, M118, D120 |
| 18654 | ND | 3 | 22-28 | R69, |

TABLE 22-continued

| Summary of the binding epitopes identified for tested anti-TIM-3 antibodies | | | | |
|---|---|---|---|---|
| Antibody | Ligand (PS) blocking | Epitope Bin | Linear epitope | Contact Residues |
| (ABTIM3) | | | 107-114 123-128 | D120, E121 |
| 21563 (mAb15) | ND | 1 | 62-67 74-80, 78-85 83-89 | P50, R69 |

TABLE 23

| TIM-3 Protein Sequences | |
|---|---|
| Protein | Amino Acid Sequence |
| Human TIM-3 UniProt Q8TDQ0 (SEQ ID NO: 236) | MFSHLPFDCVLLLLLLLLLTRSSEVEYRAEVGQNAYLPCFYTPAAPGNLVPVCWGKGACPV FECGNVVLRTDERDVNYWTSRYWLNGDFRKGDVSLTIENVTLADSGIYCCRIQIPGIMND EKFNLKLVIKPAKVTPAPTRQRDFTAAFPRMLTTRGHGPAETQTLGSLPDINLTQISTLA NELRDSRLANDLRDSGATIRIGIYIGAGICAGLALALIFGALIFKWYSHSKEKIQNLSLI SLANLPPSGLANAVAEGIRSEENIYTIEEENVYEVEEPNEYYCYVSSRQQPSQPLGCRFAM P |
| Cynomolgus TIM-3 UniProt G7P6Q7 (SEQ ID NO: 237) | MFSHLPFDCVLLLLLLLLLTRSSEVEYIAEVGQNAYLPCSYTPAPPGNLVPVCWGKGACPV FDCSNVVLRTDNRDVNDRTSGRYWLKGDFHKGDVSLTIENVTLADSGVYCCRIQIPGIMN DEKHNVKLVVIKPAKVTPAPTLQRDLTSAFPRMLTTGEHGPAETQTPGSLPDVNLTVSNF FCELQIFTLTNELRDSGATIRTAIYIAAGISAGLALALIFGALIFKWYSHSKEKTQNLSL ISLANIPPSGLANAVAEGIRSEENIYTIEEDVYEVEEPNEYYCYVSSGQQPSQPLGCRVA MP |
| Mouse TIM-3 UniProt Q8VIM0 SEQ ID NO: 238 | MFSGLTLNCVLLLLQLLLARSLENAYVFEVGKNAYLPCSYTLSTPGALVPMCWGKGFCPW SQCTNELLRTDERNVTYQKSSRYQLKGDLNKGDVSLIIKNVTLDDHGTYCCRIQFPGLMN DKKLELKLDIKAAKVTPAQTAHGDSTTASPRTLTTERNGSETQTLVTLHNNNGTKISTWA DEIKDSGETIRTAIHIGVGVSAGLTLALIIGVLILKWYSCKKKKLSSLSLITLANLPPGG LANAGAVRIRSEENIYTIEENVYEVENSNEYYCYVNSQQPS |
| Rat TIM-3 UniProt P0C0K5 SEQ ID NO: 239 | MFSWLPFSCALLLLQPLPARSLENAYTAEVGKNAYLPCSYTVPAPGTLVPICWGKGSCPL LQCASVVLRTDETNVTYRKSRRYQLKGNFYKGDMSLTIKNVTLADSGTYCCRIQFPGPMN DEKLELKLSITEPAKVIPAGTAHGDSTTASPRTLTTEGSGSETQTLVTLHDNNGTKISTW ADEIKDSGETIRTAVHIGVGVSAGLALALILGVLILKWYSSKKKKLQDLSLITLANSPPG GLVNAGAGRIRSEENIYTIEENIYEMENSNEYYCYVSSQQPS |

TABLE 24

| Anti-TIM-3 antibody sequences | | | | | | | | | |
|---|---|---|---|---|---|---|---|---|---|
| | DNA | | Protein | | | | | | |
| Ab | VH | VL | VH | VL | H-CDR1 | H-CDR2 | H-CDR3 | L-CDR1 | L-CDR2 | L-CDR3 |
| 15086.15086 | 1 | 2 | 3 | 4 | 7 | 8 | 9 | 10 | 11 | 12 |
| 15086.16837/ 15086.17145/ 15086.17144 | 13 | 14 | 15 | | | | | | | |
| 20131 | 26 | 27 | 28 | 29 | 30 | 31 | 32 | 33 | 34 | 35 |
| 20293 | 36 | 37 | 38 | 39 | 40 | 41 | 42 | 43 | 44 | 45 |
| 15105 | 46 | 47 | 48 | 49 | 50 | 51 | 52 | 53 | 54 | 55 |
| 15107 | 56 | 57 | 58 | 59 | 60 | 61 | 62 | 63 | 64 | 65 |
| 15109 | 66 | 67 | 68 | 69 | 70 | 71 | 72 | 73 | 74 | 75 |
| 15174 | 76 | 77 | 78 | 79 | 80 | 81 | 82 | 83 | 84 | 85 |
| 15175 | 86 | 87 | 88 | 89 | 90 | 91 | 92 | 93 | 94 | 95 |
| 15260 | 96 | 97 | 98 | 99 | 100 | 101 | 102 | 103 | 104 | 105 |
| 15284 | 106 | 107 | 108 | 109 | 110 | ill | 112 | 113 | 114 | 115 |
| 15299 | 116 | 117 | 118 | 119 | 120 | 121 | 122 | 123 | 124 | 125 |
| 15353 | 126 | 127 | 128 | 129 | 130 | 131 | 132 | 133 | 134 | 135 |
| 15354 | 136 | 137 | 138 | 139 | 140 | 141 | 142 | 143 | 144 | 145 |
| 17244 | 146 | 147 | 148 | 149 | 150 | 151 | 152 | 153 | 154 | 155 |
| 17245 | 156 | 157 | 158 | 159 | 160 | 161 | 162 | 163 | 164 | 165 |
| 19324 | 166 | 167 | 168 | 169 | 170 | 171 | 172 | 173 | 174 | 175 |
| 19416 | 176 | 177 | 178 | 179 | 180 | 181 | 182 | 183 | 184 | 185 |

TABLE 24-continued

Anti-TIM-3 antibody sequences

|     | DNA | | Protein | | | | | | | |
| --- | --- | --- | --- | --- | --- | --- | --- | --- | --- | --- |
| Ab | VH | VL | VH | VL | H-CDR1 | H-CDR2 | H-CDR3 | L-CDR1 | L-CDR2 | L-CDR3 |
| 19568 | 186 | 187 | 188 | 189 | 190 | 191 | 192 | 193 | 194 | 195 |
| 20185 | 196 | 197 | 198 | 199 | 200 | 201 | 202 | 203 | 204 | 205 |
| 20300 | 206 | 207 | 208 | 209 | 210 | 211 | 212 | 213 | 214 | 215 |
| 20362 | 216 | 217 | 218 | 219 | 220 | 221 | 222 | 223 | 224 | 225 |
| 20621 | 226 | 227 | 228 | 229 | 230 | 231 | 232 | 233 | 234 | 235 |

TABLE 25

Constant region and TIM-3 sequences

| SEQ ID NO | Sequence |
| --- | --- |
| 5 | IgG1 heavy chain constant region protein sequence |
| 6 | IgG1 Kappa light chain constant region protein sequence |
| 16 | IgG1-LALA heavy chain constant region DNA sequence excluding introns |
| 17 | IgG1-LALA heavy chain constant region DNA sequence including introns |
| 18 | IgG4 (S228P) heavy chain constant region DNA sequence excluding introns |
| 19 | IgG4 (S228P) heavy chain constant region DNA sequence including introns |
| 20 | IgG2 heavy chain constant region DNA sequence excluding introns |

TABLE 25-continued

Constant region and TIM-3 sequences

| SEQ ID NO | Sequence |
| --- | --- |
| 21 | IgG2 heavy chain constant region DNA sequence including introns |
| 22 | Kappa light chain constant region DNA sequence |
| 23 | IgG1-LALA heavy chain constant region protein sequence |
| 24 | IgG4 (S228P) heavy chain constant region protein sequence |
| 25 | IgG2 heavy chain constant region protein sequence |
| 236 | human TIM-3 |
| 237 | cynomolgus TIM-3 |
| 238 | mouse TIM-3 |
| 239 | rat TIM-3 |

The invention claimed is:

1. An anti-TIM-3 antibody or an antigen-binding portion thereof, wherein said antibody comprises the H-CDR1-3 and L-CDR1-3 amino acid sequences of SEQ ID NOs: 40-45, respectively.

2. The anti-TIM-3 antibody or antigen-binding portion of claim 1, wherein said antibody comprises a heavy chain (HC) and a light chain (LC) whose variable domains have the amino acid sequences of SEQ ID NOs: 38 and 39, respectively.

3. The anti-TIM-3 antibody of claim 2, wherein said HC and said LC further comprise the amino acid sequences of:
   a) SEQ ID NOs: 5 and 6, respectively;
   b) SEQ ID NOs: 25 and 6, respectively;
   c) SEQ ID NOs: 23 and 6, respectively; or
   d) SEQ ID NOs: 24 and 6, respectively.

4. An anti-TIM-3 antibody that comprises an HC comprising the amino acid sequences of SEQ ID NOs: 38 and 25 or SEQ ID NOs: 38 and 5 and an LC comprising the amino acid sequences of SEQ ID NOs: 39 and 6.

5. The anti-TIM-3 antibody of claim 1, wherein the antibody is a human IgG antibody that comprises at least one mutation in the Fc region.

6. The anti-TIM-3 antibody of claim 5, wherein
   a) the antibody is of isotype subclass $IgG_1$ and one or both of the amino acid residues at positions 234 and 235 (Eu numbering) are mutated to Ala, or
   b) the antibody is of isotype subclass $IgG_4$ and the amino acid residue at position 228 (Eu numbering) is mutated to Pro.

7. The anti-TIM-3 antibody or antigen-binding portion of claim 1, wherein the antibody or portion has at least one of the following properties:
   a) binds to human TIM-3 with a $K_D$ of 23 nM or less as measured by surface plasmon resonance;
   b) binds to cynomolgus TIM-3 with a $K_D$ of 22 nM or less as measured by surface plasmon resonance;
   c) binds to human TIM-3 with an $EC_{50}$ of 1.2 nM or less as measured by ELISA;
   d) binds to cynomolgus TIM-3 with an $EC_{50}$ of 46 nM or less as measured by ELISA;
   e) increases IFN-γ secretion in a one-way mixed lymphocyte reaction assay;
   f) increases IFN-γ secretion in a two-way mixed lymphocyte reaction assay; and
   g) increases TNF-α secretion from dendritic cells.

8. A pharmaceutical composition comprising the anti-TIM-3 antibody or antigen-binding portion of claim 1 and a pharmaceutically acceptable excipient.

9. Isolated nucleic acid molecule(s) comprising a nucleotide sequence that encodes the heavy chain amino acid sequence and a nucleotide sequence that encodes the light chain amino acid sequence of the anti-TIM-3 antibody or antigen-binding portion of claim 1.

10. Vector(s) comprising the isolated nucleic acid molecule(s) of claim 9, wherein said vector(s) further comprise an expression control sequence.

11. A host cell comprising a nucleotide sequence that encodes the heavy chain amino acid sequence and a nucleotide sequence that encodes the light chain amino acid sequence of the anti-TIM-3 antibody or antigen-binding portion of claim 1.

12. A method for producing an anti-TIM-3 antibody or an antigen-binding portion thereof, comprising providing the host cell according to claim 11, culturing said host cell under conditions suitable for expression of the antibody or portion, and isolating the resulting antibody or portion.

13. A bispecific binding molecule having an antigen-binding portion of the anti-TIM-3 antibody of claim 1 and an antigen-binding portion of another, distinct antibody.

14. A method for enhancing immunity in a patient in need thereof, comprising administering to said patient the anti-TIM-3 antibody or antigen-binding portion of claim 1.

15. The method of claim 14, further comprising administering to the patient a chemotherapeutic agent, an antineoplastic agent, an anti-angiogenic agent, a tyrosine kinase inhibitor, or a TIM-3 pathway inhibitor.

16. The method of claim 14, further comprising administering irinotecan to the patient.

17. A method for treating cancer in a patient, comprising administering to said patient the anti-TIM-3 antibody or antigen-binding portion of claim 1.

18. The method of claim 17, wherein the cancer originates in skin, lung, intestine, ovary, brain, prostate, kidney, soft tissues, hematopoietic system, head and neck, liver, bladder, breast, stomach, uterus, or pancreas.

19. The method of claim 17, wherein the cancer is leukemia, Hodgkin's lymphoma, non-Hodgkin's lymphoma, melanoma, esophageal cancer, gastroesophageal cancer, head and neck squamous cell carcinoma, non-small cell lung cancer, pancreatic cancer, biliary tract cancer, gastric cancer, colorectal cancer, renal cell carcinoma, or mesothelioma.

* * * * *